US010087151B2

(12) United States Patent
Tsvetkov et al.

(10) Patent No.: US 10,087,151 B2
(45) Date of Patent: Oct. 2, 2018

(54) SUBSTITUTED BENZOXAZINE AND RELATED COMPOUNDS

(71) Applicant: THE J. DAVID GLADSTONE INSTITUTES, A TESTAMENTARY TRUST ESTABLISHED UNDER THE WILL OF J. DAVID GLADSTONE, San Francisco, CA (US)

(72) Inventors: Andrey S. Tsvetkov, Houston, TX (US); Steven M. Finkbeiner, Corte Madera, CA (US); Michael A. Pleiss, Sunnyvale, CA (US); Robert Greenhouse, Santa Clara, CA (US)

(73) Assignee: THE J. DAVID GLADSTONE INSTITUTES, A TESTIMENTARY TRUST ESTABLISHED UNDER THE WILL OF J. DAVID GLADSTONE, San Francisco, CA (US)

( * ) Notice: Subject to any disclaimer, the term of this patent is extended or adjusted under 35 U.S.C. 154(b) by 0 days.

(21) Appl. No.: 15/110,082

(22) PCT Filed: Jan. 8, 2015

(86) PCT No.: PCT/US2015/010690
§ 371 (c)(1),
(2) Date: Jul. 6, 2016

(87) PCT Pub. No.: WO2015/106025
PCT Pub. Date: Jul. 16, 2015

(65) Prior Publication Data
US 2016/0326123 A1 Nov. 10, 2016

Related U.S. Application Data

(60) Provisional application No. 61/927,911, filed on Jan. 15, 2014, provisional application No. 61/925,619, filed on Jan. 9, 2014.

(51) Int. Cl.
| | | |
|---|---|---|
| *C07D 265/36* | (2006.01) | |
| *C07D 413/06* | (2006.01) | |
| *C07D 498/04* | (2006.01) | |
| *C07D 209/08* | (2006.01) | |
| *C07D 279/16* | (2006.01) | |
| *C07D 279/28* | (2006.01) | |
| *A61K 9/02* | (2006.01) | |
| *A61K 9/08* | (2006.01) | |
| *A61K 9/10* | (2006.01) | |
| *A61K 9/20* | (2006.01) | |
| *A61K 9/48* | (2006.01) | |

(52) U.S. Cl.
CPC .............. *C07D 265/36* (2013.01); *A61K 9/02* (2013.01); *A61K 9/08* (2013.01); *A61K 9/10* (2013.01); *A61K 9/2059* (2013.01); *A61K 9/4866* (2013.01); *C07D 209/08* (2013.01); *C07D 279/16* (2013.01); *C07D 279/28* (2013.01); *C07D 413/06* (2013.01); *C07D 498/04* (2013.01)

(58) Field of Classification Search
CPC .. C07D 265/36; C07D 279/16; C07D 498/04; C07D 209/08; C07D 279/28
USPC ........................................................ 544/105
See application file for complete search history.

(56) References Cited

U.S. PATENT DOCUMENTS

| | | | | |
|---|---|---|---|---|
| 3,547,915 A | * | 12/1970 | Bub ..................... | C07D 265/36 514/912 |
| 3,681,330 A | * | 8/1972 | Pesson ................. | C07D 265/18 250/396 R |
| 6,084,098 A | * | 7/2000 | Kover .................. | C07D 209/08 540/468 |
| 6,723,725 B1 | | 4/2004 | Bottcher et al. | |
| 7,790,726 B2 | | 9/2010 | Zhang et al. | |
| 2006/0106012 A1 | | 5/2006 | Sethofer et al. | |
| 2009/0163545 A1 | | 6/2009 | Goldfarb | |
| 2011/0280804 A1 | | 11/2011 | McCurdy et al. | |
| 2012/0040968 A1 | | 2/2012 | Shimada et al. | |
| 2012/0252780 A1 | | 10/2012 | Ng et al. | |
| 2013/0123251 A1 | | 5/2013 | Berger et al. | |

FOREIGN PATENT DOCUMENTS

| | | |
|---|---|---|
| GB | 1 137 796 | 12/1968 |
| WO | WO-03/097639 A1 | 11/2003 |
| WO | WO-2009/049242 A1 | 4/2009 |
| WO | WO-2010/128659 A1 | 11/2010 |
| WO | WO-2011/059839 A1 | 5/2011 |
| WO | WO-2011/150183 A1 | 12/2011 |
| WO | WO-2012/020567 A1 | 2/2012 |
| WO | WO-2012/080729 A3 | 6/2012 |
| WO | WO-2012/080729 A4 | 6/2012 |
| WO | WO-2013/114332 A1 | 8/2013 |

OTHER PUBLICATIONS

Dezi, C, Modeling of 5-HT2A and 5-HT2C Receptors and of Their Complexes with Actual and Potential Antipsychotic Drugs, PhD Thesis, Pompeu Fabra University, pp. 1-239. Barcelona, 2007.
PCT International Search Report & Written Opinion, PCT Application No. PCT/US215/010690, dated Apr. 13, 2015.
Tsvetkov ,AS et al., A small-molecule scaffold induces autophagy in primary neurons and protects against toxicity in a Huntington disease model, PNAS 107(39), pp. 16982-16987, 2010.
Abate, Carmen et al., "2-Aminopyridine Derivatives as Potential ** Receptor Antagonists", ChemMedChem 2012, 7, 1847-1857.
Extended Search Report for EP Patent Application No. 15735106.5 dated May 24, 2017, 10 pages.
Karlsson, Daniela et al., "The exploration of thienothiazines as selective butyrylcholinesterase inhibitors", European Journal of Pharmaceutical Sciences 47 (2012, 190-205.

* cited by examiner

*Primary Examiner* — Kahsay Habte
(74) *Attorney, Agent, or Firm* — Foley & Lardner LLP; Antoinette F. Konski; Alice Lee-Dutra

(57) ABSTRACT

The present invention relates to compounds including but not limited to of any one of formulas Ia, Ib, IIa, IIb, IIIa, IIIb, and IV to VI, VIIa, VIIb, VIIIa, VIIIb and VIIIc as described herein and their tautomers and/or pharmaceutically acceptable salts, compositions, and methods of uses thereof.

16 Claims, No Drawings

SUBSTITUTED BENZOXAZINE AND RELATED COMPOUNDS

CROSS-REFERENCE TO RELATED APPLICATION

This application is a U.S. national stage filing under 35 U.S.C. § 371 of International Application No. PCT/US2015/ 010690, filed Jan. 8, 2015 entitled "SUBSTITUTED BENZOXAZINE AND RELATED COMPOUNDS" which claims priority to Provisional Application Nos. 61/925,619 file on Jan. 9, 2014, and 61/927,911 filed Jan. 15, 2014 each of which is hereby incorporated by reference in its entirety.

GOVERNMENT LICENSE RIGHTS

This invention was made with government support under Grant Nos. NS081844-01, NS039074-15 and NS045191-10 awarded by the National Institutes of Health (NIH). The government has certain rights in the invention.

FIELD OF THE INVENTION

This invention relates to substituted benzoxazine and related compounds and derivatives thereof for use as stimulators of neuronal autophagy. In certain aspects, this invention relates to treating diseases such as Huntington's, Alzheimer's, amyotrophic lateral sclerosis (ALS), frontotemporal dementia, and Parkinson's disease by administering a pharmaceutical composition of said compound to a patient. In another aspect, this invention is generally applicable toward the treatment of neurodegenerative disorders. In still other aspects, this invention relates to treating certain bacterial and viral infections by administering a pharmaceutical composition of said compound to a patient.

BACKGROUND OF THE INVENTION

Genes and their associated enzymatic complexes govern the main pathways of autophagy. Macroautophagy is the pathway for removal of degraded or damaged proteins and organelles at a cellular level. Modulation of this highly specific process has been a general approach toward the treatment of diseases associated with cellular over-accumulation of some misfolded proteins. Whereas the other major protein clearance pathway, the ubiquitin proteasome pathway, is unable to degrade aggregated proteins (normal or misfolded), autophagy can engulf and clear protein aggregates as well as monomeric proteins. Misfolded proteins, as monomers or in aggregates, can cause neurodegeneration by using up critical components of the chaperone-protein folding processes and protein clearance pathways, leading to additional protein misfolding and the loss of function of a variety of essential proteins. Aggregates may also cause direct damage to organelles and interfere with an array of cellular functions such as transcription and axonal transport. Likewise, aberrant autophagy is implicated in various cancers. Thus, compositions and methods which stimulate the autophagic clearance of misfolded proteins and/or protein aggregates is of considerable interest.

An illustrative example of neurodegenerative disorders related to cellular over-accumulation of misfolded proteins is Huntington's disease. Huntington's disease is categorized as a trinucleotide repeat disorder and caused by expansion of a repeated section of the gene, HTT, that encodes the protein HUNTINGTIN. Normal HUNTINGTIN protein contains a region referred to as the "PolyQ region", which has a repeated sequence of the DNA triplet base cytosine-adenine-guanine (CAG), which codes for the amino acid glutamine (Q). A mutant HUNTINGTIN gene, mHTT, generates a mutant HUNTINGTIN protein with a PolyQ region containing greater than 36 glutamine residues. This mutant protein is misfolded and is also cleaved to produce numerous fragments. Both the misfolded protein and the fragments are contemplated to be particularly toxic. Accordingly, areas of the brain possessing cells with the mutant gene and correspondingly high likelihood and/or presence of misfolded protein are found to show a correspondingly higher incidence of adverse effects.

Another example of a misfolded-protein associated disorder is Parkinson's disease. In Parkinson's patients, over-expression of the protein, α-SYNUCLEIN, can result from duplication or triplication of the SNCA gene locus and occurs for unknown reasons in the vast majority of Parkinson's patients, who develop the disease without any identifiable mutation. In addition, A53T and A30P point mutations of the gene have been demonstrated to trigger the early onset of Parkinson's. Further, over-expression of the wild type protein in transgenic mice and flies has been shown to cause progressive neuronal defects. The accumulation of α-SYNUCLEIN in misfolded and aggregated forms, is strongly associated with neuronal dysfunction and death. Clearly, the homeostatic removal of misfolded proteins and/or protein aggregates is a prime therapeutic target for the treatment of Huntington's, Parkinson's, and other such related disorders.

Examples of other disorders and diseases categorized as proteopathies include, but are not limited to: Alzheimer's disease, frontotemporal dementia, amyotrophic lateral sclerosis (ALS), spinocerebellar ataxia of types 1, 2, 3, 6, 7 and 17, spinobullar muscular atrophy; dentatorubral-palli-doluysian atrophy, peripheral neuropathy, and dementia. Treatment of these types of diseases can be affected by the administration of an active pharmaceutical ingredient, which is capable of inducing autophagic removal of the particular toxic misfolded proteins and/or protein aggregates.

Some bacterial and viral infections are treatable by autophagic upregulation, as well. Pathogens can be engulfed by autophagosomes and further disposed of by lysosomes. *Streptococcus* (Group A) and Herpes virus (Type I) are important examples of pathogens, although not limiting, that are susceptible to this kind of capture.

There remains a need for compounds that are effective stimulants of autophagic removal of misfolded proteins and/or protein aggregates and such compounds can be used in treating neurodegenerative disorders. Compounds that induce neuronal autophagy and can be used to treat and prevent neurodegenerative disorders characterized by misfolded proteins and/or protein aggregates are provided herein.

SUMMARY OF THE INVENTION

This invention is directed to novel compounds, pharmaceutical compositions, and methods of their use to treat neurodegenerative disorders. This invention is also generally applicable toward the treatment of any cellular disorder associated with an over-accumulation of misfolded proteins and/or protein aggregates.

Autophagy is a natural protective mechanism that removes toxic, misfolded proteins, and their aggregates from neurons. However, many neurodegenerative disorders are characterized by a condition in which autophagy is impaired in neurons, microglia, or both. This natural clearance mechanism appears to be overwhelmed. In ALS, for example, motor neurons gradually degenerate, resulting in paralysis and muscle atrophy for patients.

Autophagy is an ideal approach for removing toxic, disease-causing proteins. It directs such proteins, which include misfolded proteins and/or protein aggregates, to lysosomes for degradation. Autophagy is essential for cell survival. There is a need for a new family of neuronal autophagy inducers that will enhance removal of such misfolded proteins and/or protein aggregates from neurons, with minimal toxicity.

Herein identified are a series of compounds that effectively induce autophagy in neurons and protect striatal neurons. In one embodiment, the compounds herein are shown to mitigate the neurodegenerative effects of the mutant form of mHTT protein, which contributes to Huntington's disease (HD). Such activity is indicative of induced autophagy and suggests the use of these compounds in other diseases arising from an over-accumulation of misfolded proteins and/or protein aggregates.

It is provided that these compounds are evaluated with comparable, in vitro, neuron models. Specifically, a primary neuron model for HD has been developed, using a robotic microscope (disclosed in U.S. Pat. No. 7,139,415, which is incorporated herein by reference in its entirety). This model has been utilized to screen a library of compounds and their derivatives in order to identify active compounds.

In one aspect, there are provided compounds of formula Ia, Ib, Ic, or Id:

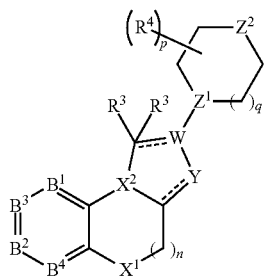
Ia

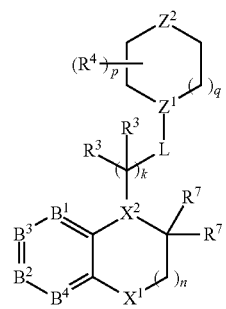
Ib

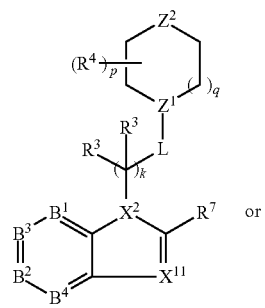
Ic or

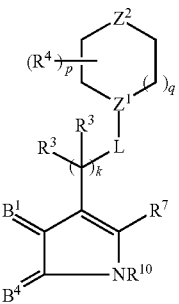
Id wherein:
$X^1$ is selected from the group consisting of $CH_2$, O, C(O), S, SO, $SO_2$, $CR^{10}R^{10}$, NH, and $NR^{10}$;

$X^{11}$ is selected from the group consisting of N or $CR^{10}$;

$R^{10}$ is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl, substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl;

$X^2$ and $Z^1$ independently are $CR^{10}$ or N;

$Z^2$ is $CR^{10}R^5$, $NR^5$, O, S, SO or $SO_2$;

$B^1$, $B^2$ and $B^4$ independently are selected from the group consisting of $CR^2$ and N, $B^3$ is selected from the group consisting of $CR^1$ and N, wherein no more than two of $B^1$, $B^2$, $B^3$, and $B^4$ are N;

Y is selected from the group consisting of CH, $CHR^{10}$, N, and $NR^{10}$;

L is selected from the group consisting of a covalent bond, $CR^6_2$, C(O)—$(CR^6_2)_m$, C(S)—$(CR^6_2)_m$, O—$(CR^6_2)_m$, S—$(CR^6_2)_m$, SO—$(CR^6_2)_m$, $SO_2$—$(CR^6_2)_m$, and $NR^6$—$(CR^6_2)_m$; or a —$CR^6_2CR^6_2$— present in —$(CR^3_2)_k$-L- is optionally replaced with —$CR^6$=$CR^6$— or —C≡C—;

the variables k, m, n, p, q independently are 0, 1, 2, 3, 4, 5, 6, or 7;

$R^1$ and $R^2$ independently are selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or $R^1$ and either $B^1$ or $B^2$ join to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, aryl, substituted aryl, heteroaryl, and substituted heteroaryl;

each $R^3$ independently is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or two $R^3$ on the same carbon together with the carbon attached thereto form C=$CR^{10}_2$, C=O, C=$NR^{10}$, or C=S, or two $R^3$ join together to form a ring selected from the group consisting of $C_3$-$C_7$ cycloalkyl, substituted $C_3$-$C_7$ cycloalkyl, $C_3$-$C_7$ heterocycloalkyl, and substituted $C_3$-$C_7$ heterocycloalkyl;

each $R^4$ independently is selected from the group consisting of halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or two $R^4$ on the same carbon together with the carbon attached thereto form C=$CR^{10}_2$, C=O, C=$NR^{10}$, or C=S, or two $R^4$ join together to form a ring selected from the group consisting of $C_3$-$C_7$ cycloalkyl, substituted $C_3$-$C_7$ cycloalkyl, $C_3$-$C_7$ heterocycloalkyl, substituted $C_3$-$C_7$ heterocycloalkyl, heteroaryl, and substituted heteroaryl;

or $R^3$ and $R^4$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, heteroaryl, and substituted heteroaryl;

$R^5$ is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl;

each $R^6$ independently is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or two $R^6$ on the same carbon together with the carbon attached thereto form C=$CR^{10}_2$, C=O, C=$NR^{10}$, or C=S, or two $R^6$ join together to form a ring selected from the group consisting of $C_3$-$C_7$ cycloalkyl, substituted $C_3$-$C_7$ cycloalkyl, $C_3$-$C_7$ heterocycloalkyl, and substituted $C_3$-$C_7$ heterocycloalkyl;

each $R^7$ independently is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or two $R^7$ together with the carbon attached thereto form C=$CR^{10}_2$, C=O, C=$NR^{10}$, or C=S, or two $R^7$ join together to form a ring selected from the group consisting of $C_3$-$C_7$ cycloalkyl, substituted $C_3$-$C_7$ cycloalkyl, $C_3$-$C_7$ heterocycloalkyl, and substituted $C_3$-$C_7$ heterocycloalkyl;

═ represents a single or double bond;

or a tautomer and/or a pharmaceutically acceptable salt thereof.

When two substituents, such as two $R^3$, join together to form a ring, it is understood that the ring also includes the atom(s), such as one or more carbon atom(s), to which the substituent is attached, and that the two substituents may be attached to the same atom, or attached to two different atoms, and if attached to two different atoms, the two different atoms may be adjacent to each other or be separated by one or two other atoms, which may be independently carbon, nitrogen, oxygen or sulfur (provided that at least one of the other atoms is carbon).

In one aspect, there are provided compounds of formula IIa, IIb, IIc, or IId:

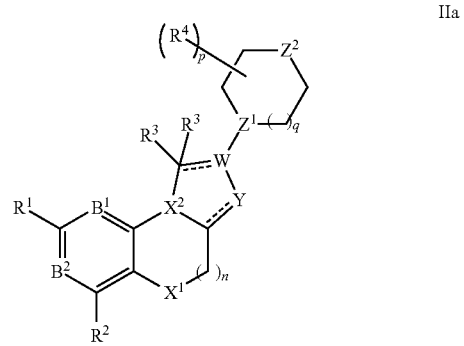

IIa

-continued

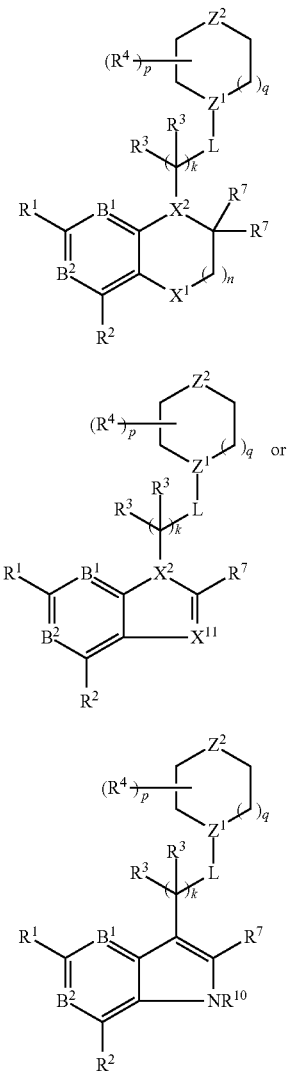

IIb

IIc

IId wherein:

X[1] is selected from the group consisting of CH$_2$, O, C(O), S, SO, SO$_2$, CR$^{10}$R$^{10}$, NH, and NR$^{10}$;

X[11] is selected from the group consisting of N or CR$^{10}$;

R$^{10}$ is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl, substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl;

X$^2$ and Z$^1$ independently are CR$^{10}$ or N;

Z$^2$ is CR$^{10}$R$^5$, NR$^5$, O, S, SO or SO$_2$;

B$^1$ and B$^2$ independently are selected from the group consisting of CR$^2$ and N;

W is selected from the group consisting of C, CH, and N;

Y is selected from the group consisting of CR$^{10}$, CHR$^{10}$, N, and NR$^{10}$;

L is selected from the group consisting of a covalent bond, CR$^6_2$, C(O)—(CR$^6_2$)$_m$, C(S)—(CR$^6_2$), O—(CR$^6_2$), S—(CR$^6_2$), SO—(CR$^6_2$), SO$_2$—(CR$^6_2$), and NR$^6$—(CR$^6_2$)$_m$; or a —CR$^6_2$CR$^6_2$— present in —(CR$^3_2$)$_k$-L- is optionally replaced with —CR$^6$=CR$^6$— or —C≡C—;

the variables k, m, n, p, q independently are 0, 1, 2, 3, 4, 5, 6, or 7;

R$^1$ and R$^2$ independently are selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or R$^1$ and either B$^1$ or B$^2$ join to form a ring selected from the group consisting of C$_5$-C$_7$ cycloalkyl, substituted C$_5$-C$_7$ cycloalkyl, C$_5$-C$_7$ heterocycloalkyl, substituted C$_5$-C$_7$ heterocycloalkyl, aryl, substituted aryl, heteroaryl, and substituted heteroaryl;

each R$^3$ independently is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or two R$^3$ on the same carbon together with the carbon attached thereto form C=CR$^{10}_2$, C=O, C=NR$^{10}$, or C=S, or two R$^3$ join together to form a ring selected from the group consisting of C$_3$-C$_7$ cycloalkyl, substituted C$_3$-C$_7$ cycloalkyl, C$_3$-C$_7$ heterocycloalkyl, and substituted C$_3$-C$_7$ heterocycloalkyl;

each R$^4$ independently is selected from the group consisting of halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or two R$^4$ on the same carbon together with the carbon attached thereto form C=CR$^{10}_2$, C=O, C=NR$^{10}$, or C=S, or two R$^4$ join together to form a ring selected from the group consisting of C$_3$-C$_7$ cycloalkyl, substituted C$_3$-C$_7$ cycloalkyl, C$_3$-C$_7$ heterocycloalkyl, substituted C$_3$-C$_7$ heterocycloalkyl, heteroaryl, and substituted heteroaryl;

or R$^3$ and R$^4$ join together to form a ring selected from the group consisting of C$_5$-C$_7$ cycloalkyl, substituted C$_5$-C$_7$ cycloalkyl, C$_5$-C$_7$ heterocycloalkyl, substituted C$_5$-C$_7$ heterocycloalkyl, heteroaryl, and substituted heteroaryl;

R$^5$ is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl;

each R$^6$ independently is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or two R$^6$ on the same carbon together with the carbon attached thereto form C=CR$^{10}_2$, C=O, C=NR$^{10}$, or C=S, or two R$^6$ join together to form a ring selected from the group consisting of C$_3$-C$_7$ cycloalkyl, substituted C$_3$-C$_7$ cycloalkyl, C$_3$-C$_7$ heterocycloalkyl, and substituted C$_3$-C$_7$ heterocycloalkyl;

each R$^7$ independently is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or two R$^7$ together with the carbon attached thereto form C=CR$^{10}_2$, C=O, C=NR$^{10}$, or C=S, or two R$^7$ join together to form a ring selected from the group consisting of C$_3$-C$_7$ cycloalkyl, substituted C$_3$-C$_7$ cycloalkyl, C$_3$-C$_7$ heterocycloalkyl, and substituted C$_3$-C$_7$ heterocycloalkyl;

═══ represents a single or double bond;

or a tautomer and/or a pharmaceutically acceptable salt thereof.

In one aspect, there are provided compounds of formula IIIa or IIIb:

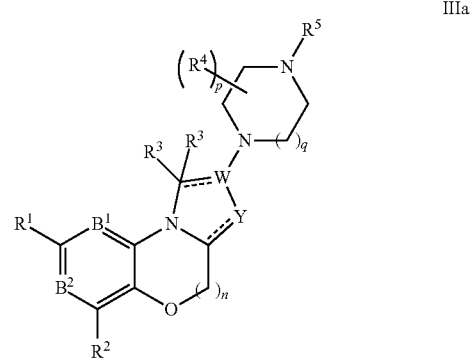

IIIa

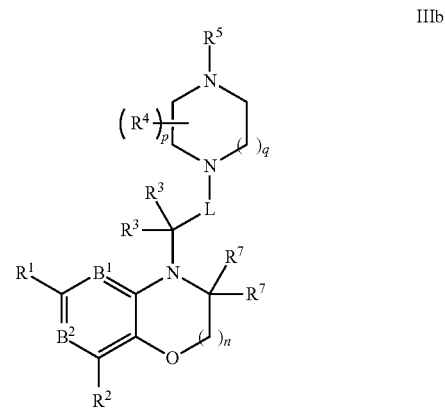

IIIb wherein:

B$^1$ and B$^2$ independently are selected from the group consisting of CR$^2$ and N;

L is selected from the group consisting of a covalent bond, CR$^6_2$, C(O)—(CR$^6_2$)$_m$, C(S)—(CR$^6_2$)$_m$, O—(CR$^6_2$)$_m$, S—(CR$^6_2$)$_m$, SO—(CR$^6_2$)$_m$, SO$_2$—(CR$^6_2$)$_m$, and NR$^6$—(CR$^6_2$)$_m$;

the variables m, n, p, q independently are 0, 1, 2, 3, 4, 5, 6, or 7;

R$^1$ and R$^2$ independently are selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, nitro, cyano, carboxyl ester, (carboxyl ester)amino, (carboxyl ester)oxy, hydroxyl, acyl, formyl, aminocarbonyl, substituted aminocarbonyl, and substituted aminothiocarbonyl, or R$^1$ and either B$^1$ or B$^2$ join together to form a ring selected from the group consisting of C$_5$-C$_7$ cycloalkyl, substituted C$_5$-C$_7$ cycloalkyl, C$_5$-C$_7$ heterocycloalkyl, substituted C$_5$-C$_7$ heterocycloalkyl, aryl, substituted aryl, heteroaryl, and substituted heteroaryl;

each R$^3$ independently is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, cyano, carboxyl ester, (carboxyl ester) amino, (carboxyl ester)oxy, hydroxyl, acyl, formyl, aminocarbonyl, substituted aminocarbonyl, and substituted aminothiocarbonyl, or two $R^3$ on the same carbon together with the carbon attached thereto form C=$CR^{10}_2$, C=O, C=$NR^{10}$, or C=S, or two $R^3$ join together to form a ring selected from the group consisting of $C_3$-$C_7$ cycloalkyl, substituted $C_3$-$C_7$ cycloalkyl, $C_3$-$C_7$ heterocycloalkyl, substituted $C_3$-$C_7$ heterocycloalkyl;

each $R^4$ independently is selected from the group consisting of halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or two $R^4$ on the same carbon together with the carbon attached thereto form C=$CR^{10}_2$, C=O, C=$NR^{10}$, or C=S, or two $R^4$ join together to form a ring selected from the group consisting of $C_3$-$C_7$ cycloalkyl, substituted $C_3$-$C_7$ cycloalkyl, $C_3$-$C_7$ heterocycloalkyl, substituted $C_3$-$C_7$ heterocycloalkyl, heteroaryl, and substituted heteroaryl;

or $R^3$ and $R^4$ join together to form a ring selected from the group consisting of $C_5$-$C_7$ cycloalkyl, substituted $C_5$-$C_7$ cycloalkyl, $C_5$-$C_7$ heterocycloalkyl, substituted $C_5$-$C_7$ heterocycloalkyl, heteroaryl, and substituted heteroaryl;

$R^5$ is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, cyano, carboxyl ester, (carboxyl ester)amino, (carboxyl ester)oxy, hydroxyl, acyl, formyl, aminocarbonyl, substituted aminocarbonyl, and substituted aminothiocarbonyl;

each $R^6$ independently is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, cyano, carboxyl ester, (carboxyl ester) amino, (carboxyl ester)oxy, hydroxyl, acyl, formyl, aminocarbonyl, substituted aminocarbonyl, and substituted aminothiocarbonyl, or two $R^6$ on the same carbon together with the carbon attached thereto form C=$CR^{10}_2$, C=O, C=$NR^{10}$, or C=S, or two $R^6$ join together to form a ring selected from the group consisting of $C_3$-$C_7$ cycloalkyl, substituted $C_3$-$C_7$ cycloalkyl, $C_3$-$C_7$ heterocycloalkyl, substituted $C_3$-$C_7$ heterocycloalkyl;

each $R^7$ independently is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, cyano, carboxyl ester, (carboxyl ester) amino, (carboxyl ester)oxy, hydroxyl, acyl, formyl, aminocarbonyl, substituted aminocarbonyl, and substituted aminothiocarbonyl, or two $R^7$ together with the carbon attached thereto form C=$CR^{10}_2$, C=O, C=$NR^{10}$, or C=S, or two $R^7$ join together to form a ring selected from the group consisting of $C_3$-$C_7$ cycloalkyl, substituted $C_3$-$C_7$ cycloalkyl, $C_3$-$C_7$ heterocycloalkyl, substituted $C_3$-$C_7$ heterocycloalkyl;

═══ represents a single or double bond;

or a tautomer and/or a pharmaceutically acceptable salt thereof.

The invention also provides pharmaceutical compositions comprising an effective amount of one or more compounds of Formula Ia, Ib, IIa, IIb, IIIa and/or IIIb described herein and a pharmaceutically acceptable excipient.

In one of its method aspects, this invention is directed to a method for inducing neuronal autophagy which comprises contacting cells (including, but not limited to, neurons, microglia, macrophages, and astrocytes) with an effective amount of one or more compounds of Formula Ia, Ib, IIa, IIb, IIIa and/or IIIb described herein under conditions where neuronal autophagy is induced.

In another of its method aspects, this invention is directed to a method for treating a disease mediated at least in part by an accumulation of misfolded proteins and/or protein aggregates, which method comprises administering to a patient an effective amount of one or more compounds of Formula Ia, Ib, IIa, IIb, IIIa and/or IIIb, or a pharmaceutical composition comprising a pharmaceutically acceptable excipient and an effective amount of one or more compounds of Formula Ia, Ib, IIa, IIb, IIIa and/or IIIb described herein.

Diseases mediated at least in part by the accumulation of misfolded proteins and/or protein aggregates include those selected from the group consisting of Huntington's disease and other polyglutamine disorders such as spinocerebellar ataxias, Alzheimer's disease, Parkinson's disease, amyotrophic lateral sclerosis (ALS), high-pressure neurological syndrome, dystonia, olivopontocerebellar atrophy, multiple sclerosis, frontotemporal dementia, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasitic, for example, poliomyelitis, Lyme disease (*Borrelia burgdorferi* infection) and malaria, cancers with cerebral localization, Tourette's syndrome, hepatic encephalopathy, systemic lupus, analgesia and opiate-withdrawal symptoms, feeding behaviour, schizophrenia, chronic anxiety, depressive disorders, disorders of the developing or aged brain, diseases of addiction, diabetes, and complications thereof. The compounds of this invention may influence synaptogenesis after brain injury and memory.

In another of its method aspects, this invention is directed to an article of manufacture for use to induce neuronal autophagy for treating a disease mediated at least in part by an accumulation of misfolded proteins and/or protein aggeregates comprising a composition comprising a compound of the Formula Ia, Ib, Ia, IIb, IIIa and/or IIIb as provided herein. The diseases mediated at least in part by an accumulation of misfolded proteins and/or protein aggregates are as provided herein. In one embodiment, the article of manufacture further comprises a label with instructions for using the composition to treat a disease mediated at least in part by an accumulation of misfolded proteins and/or protein aggregates.

These and other embodiments are described in details in the texts that follow.

DETAILED DESCRIPTION OF THE INVENTION

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

1. Definitions

As used herein, the following definitions shall apply unless otherwise indicated. Further, if any term or symbol used herein is not defined as set forth below, it shall have its ordinary meaning in the art.

"Comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of other ingredients and substantial method steps recited. Embodiments defined by each of these transition terms are within the scope of this invention.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$, n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$, n-pentyl ($CH_3CH_2CH_2CH_2CH_2$—), and neopentyl (($CH_3)_3CCH_2$—). $C_x$ alkyl refers to an alkyl group having x number of carbon atoms.

"Alkenyl" refers to straight or branched hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH). $C_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

Preferred substituted alkyl groups include halogenated alkyl groups and particularly halogenated methyl groups such as trifluoromethyl, difluoromethyl, fluoromethyl and the like.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxyl or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluoromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —$NR^{30}$C(O)alkyl, —$NR^{30}$C(O)substituted alkyl, —$NR^{30}$C(O)cycloalkyl, —$NR^{30}$C(O)substituted cycloalkyl, —$NR^{30}$C(O)alkenyl, —$NR^{30}$C(O)substituted alkenyl, alkoxy, substituted alkoxy-$NR^{30}$C(O)alkynyl, —$NR^{30}$C(O)substituted alkynyl, —$NR^{30}$C(O)aryl, —$NR^{30}$C(O)substituted aryl, —$NR^{30}$C(O)heteroaryl, —$NR^{30}$C(O)substituted heteroaryl, —$NR^{30}$C(O)heterocyclic, and —$NR^{30}$C(O)substituted heterocyclic wherein $R^{30}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{31}R^{32}$ where $R^{31}$ and $R^{32}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, and substituted sulfonyl and wherein $R^{31}$ and $R^{32}$ are optionally joined, together with the nitrogen bound thereto to form a heterocyclic or substituted heterocyclic group, provided that $R^{31}$ and $R^{32}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{31}$ is hydrogen and $R^{32}$ is alkyl, the substituted amino group is sometimes referred to herein as alkylamino. When $R^{31}$ and $R^{32}$ are alkyl, the substituted amino group is sometimes referred to herein as dialkylamino. When referring to a monosubstituted amino, it is meant that either $R^{31}$ or $R^{32}$ is hydrogen but not both. When referring to a disubstituted amino, it is meant that neither $R^{31}$ nor $R^{32}$ are hydrogen.

"Aminocarbonyl" refers to the group —C(O)$NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)$NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —$NR^{30}$C(O)$NR^{33}R^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{30}$C(S)NR$^{33}$R$^{34}$ where R$^{30}$ is hydrogen or alkyl and R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{30}$—SO$_2$NR$^{33}$R$^{34}$ where R$^{30}$ is hydrogen or alkyl and R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where R$^{33}$, R$^{34}$, and R$^{35}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O- substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to a saturated or unsaturated but nonaromatic cyclic alkyl groups of from 3 to 10 carbon atoms having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Guanidino" refers to the group —NHC(=NH)NH$_2$.

"Substituted guanidino" refers to —NR$^{36}$C(=NR$^{36}$)N(R$^{36}$)$_2$ where each R$^{36}$ is independently selected from the group consisting of hydrogen, alkyl, substituted alkyl, aryl, substituted aryl, heteroaryl, substituted heteroaryl, heterocyclic, and substituted heterocyclic and two R$^{36}$ groups attached to a common guanidino nitrogen atom are optionally joined together with the nitrogen bound thereto to form a heterocyclic or substituted heterocyclic group, provided that at least one R$^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. $C_x$ cycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, and tetrahydrofuranyl.

"Nitro" refers to the group —NO$_2$.

"Oxo" refers to the atom (=O) or (—O$^-$).

"Spiro ring systems" refers to bicyclic ring systems that have a single ring carbon atom common to both rings.

"Sulfinyl" refers to the divalent group —SO—.

"Sulfonyl" refers to the divalent group —S(O)$_2$—.

"Substituted sulfonyl" refers to the group —SO$_2$-alkyl, —SO$_2$-substituted alkyl, —SO$_2$—OH, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—. Preferred substituted alkyl groups on the substituted alkyl-SO$_2$-include halogenated alkyl groups and particularly halogenated methyl groups such as trifluoromethyl, difluoromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluoromethyl, fluoromethyl and the like.

"Sulfonyloxy" or "substituted sulfonyloxy" refers to the group —OSO$_2$-alkyl, —OSO$_2$-substituted alkyl, —OSO$_2$—OH, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluoromethyl, fluoromethyl and the like.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N-moiety such as pyrazoles, imidazoles, benzimidazoles, triazoles, and tetrazoles.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease "Patient" refers to mammals and includes humans and non-human mammals. Examples of patients include, but are not limited to mice, rats, hamsters, guinea pigs, pigs, rabbits, cats, dogs, goats, sheep, cows, and humans. In some embodiments, patient refers to a human.

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

"Misfolded proteins and/or protein aggregates" refers to cellular proteins which, due to mutations (resulting in amino acid substitutions), post-translational modifications or some form of cellular imbalance (including, but not limited to, changes in temperature, pH, increased protein production, decreased protein clearance) undergo conformational changes and accumulate abnormally within the cell, with resultant cellular toxicity. The misfolded proteins can exist as monomers or can polymerize into aggregates. These "misfolded proteins and/or protein aggregates" can be removed from the cell by the macroautophagy pathway.

"Proteopathy" refers to a disease state that is characterized by the abnormal accumulation of proteins and the subsequent toxicity resulting from said accumulation. Such proteins are most often misfolded and may agglomerate into aggregates with other proteins including misfolded proteins. As used herein, an "aggregate" is a non-functional and abnormal agglomeration of proteins. In one embodiment, at least one of the proteins in the aggregate is a misfolded protein. For the purposes of this application, examples of disorders and diseases categorized as a proteopathy include, but are not limited to: Huntington's disease, Parkinson's disease, Alzheimer's disease, frontotemporal dementia, amyotrophic lateral sclerosis (ALS), spinocerebellar ataxia of types 1, 2, 3, 6, 7 and 17, spinobullar muscular atrophy; dentatorubral-palli-doluysian atrophy, peripheral neuropathy, type 2 diabetes, and dementia.

It is understood that the above definitions are not intended to include impermissible substitution patterns (e.g., methyl substituted with 5 fluoro groups). Such impermissible substitution patterns are well known to the skilled artisan.

2. Compounds of the Invention

This invention is directed to compounds, compositions, and methods of using said compounds as inducing neuronal autophagy in order to treat disorders which are mediated at least in part by the accumulation of misfolded proteins and/or protein aggregates.

In one aspect, the present invention provides one or more compounds of Formula Ia, Ib, IIa, IIb, IIIa and/or IIIb described herein.

In certain embodiments, the compound is of Formula Ia or Ib wherein $B^1$ is $CR^2$, $B^2$ is $CR^2$, $B^3$ is $CR^1$, and $B^4$ is $CR^2$.

In certain embodiments, the compound is of Formula Ia or Ib wherein $B^1$ is $CR^2$, $B^2$ is $CR^2$, $B^3$ is $CR^1$, and $B^4$ is N.

In certain embodiments, the compound is of Formula Ia or Ib wherein $B^1$ is $CR^2$, $B^2$ is $CR^2$, $B^3$ is N, and $B^4$ is $CR^2$.

In certain embodiments, the compound is of Formula Ia or Ib wherein $B^1$ is $CR^2$, $B^2$ is N, $B^3$ is $CR^1$, and $B^4$ is $CR^2$.

In certain embodiments, the compound is of Formula Ia or Ib wherein $B^1$ is N, $B^2$ is $CR^2$, $B^3$ is $CR^1$, and $B^4$ is $CR^2$.

In certain embodiments, the compound is of Formula Ia or Ib wherein $B^1$ is N, $B^2$ is N, $B^3$ is $CR^1$, and $B^4$ is $CR^2$.

In certain embodiments, the compound is of Formula Ia or Ib wherein $B^1$ is N, $B^2$ is $CR^2$, $B^3$ is N, and $B^4$ is $CR^2$.

In certain embodiments, the compound is of Formula Ia or Ib wherein $B^1$ is N, $B^2$ is $CR^2$, $B^3$ is $CR^1$, and $B^4$ is N.

In certain embodiments, the compound is of Formula Ia or Ib wherein $B^1$ is $CR^2$, $B^2$ is N, $B^3$ is N, and $B^4$ is $CR^2$.

In certain embodiments, the compound is of Formula Ia or Ib wherein $B^1$ is $CR^2$, $B^2$ is N, $B^3$ is $CR^1$, and $B^4$ is N.

In certain embodiments, the compound is of Formula Ia or Ib wherein $B^1$ is $CR^2$, $B^2$ is $CR^2$, $B^3$ is N, and $B^4$ is N.

In certain embodiments, $R^1$ and $R^2$ are independently hydrogen, halo, nitro, cyano, $C_1$ to $C_6$ alkyl, hydroxyl, $C_1$ to $C_6$ alkoxy, $C_1$ to $C_6$ haloalkyl or $C_1$ to $C_6$ haloalkoxy.

In certain embodiments, the compound is of Formula Ia, Ib, IIa or IIb wherein $Z^2$ is $CR^{10}R^5$. In some embodiments, $Z^2$ is $NR^5$. In some embodiments, $Z^2$ is O. In some embodiments, $Z^2$ is S. In some embodiments, $Z^2$ is SO. In some embodiments, $Z^2$ is $SO_2$.

In certain embodiments, $R^{10}$ is hydrogen and $R^5$ is hydrogen, $C_1$ to $C_6$ alkyl, phenyl, or acyl, such as $C_1$ to $C_6$ alkylCO—, or $CH_3CO$—.

In certain embodiments, the compound is of Formula Ia, Ib, IIa or IIb wherein $X^1$ is $CH_2$. In certain embodiments, $X^1$ is $CR^{10}_2$. In certain embodiments, $X^1$ is $CHR^{10}$. In some embodiments, $R^{10}$ is $C_1$ to $C_6$ alkyl, such as $CH_3$.

In certain embodiments, the compound is of Formula Ia, Ib, or IIa wherein $X^1$ is NH.

In certain embodiments, the compound is of Formula Ia, Ib, or IIa wherein $X^1$ is $NR^{10}$. In some embodiments, $R^{10}$ is $C_1$ to $C_6$ alkyl, such as $CH_3$.

In certain embodiments, the compound is of Formula Ia, Ib, or IIa wherein $X^1$ is S.

In certain embodiments, the compound is of Formula Ia, Ib, or IIa wherein $X^1$ is SO.

In certain embodiments, the compound is of Formula Ia, Ib, or IIa wherein $X^1$ is $SO_2$.

In certain embodiments, the compound is of Formula Ia, Ib, or IIa wherein $X^1$ is O.

In certain embodiments, the compound is of Formula Ia, Ib, or IIa wherein $X^2$ is $CR^{10}$ such as CH.

In certain embodiments, the compound is of Formula Ia, Ib, or IIa wherein $X^2$ is N.

In certain embodiments, the compound is of Formula Ia, Ib, or IIa wherein $Z^1$ is CH.

In certain embodiments, the compound is of Formula Ia, Ib, or IIa wherein $Z^1$ is N.

In certain embodiments, the compound is of Formula Ia, Ib, or IIa wherein $Z^2$ is $CHR^5$.

In certain embodiments, the compound is of Formula Ia, Ib, or IIa wherein $Z^2$ is $NR^5$.

In certain embodiments, the compound is of Formula Ia, Ib, or IIa wherein $R^1$ is $C_1$ to $C_6$ alkyl, such as $CH_3$.

In certain embodiments, the compound is of Formula Ia, Ib, or IIa wherein $R^1$ is $C_1$ to $C_6$ alkyl, such as $CH_3$ and $B^2$ is CH.

In certain embodiments, the compound is of Formula Ia, Ib, or IIa wherein $R^2$ is hydrogen or $C_1$ to $C_6$ alkyl, such as $CH_3$.

In certain embodiments, the compound is of Formula Ia, Ib, or IIa wherein $R^2$ is hydrogen or $C_1$ to $C_6$ alkyl, such as $CH_3$ and $B^1$ is CH.

In certain embodiments, the compound is of Formula Ia, Ib, or IIa wherein $B^1$ is $CR^2$ and $R^2$ is $C_1$ to $C_6$ alkyl, such as $CH(CH_3)_2$ and $B^2$ is CH.

In certain embodiments, the compound is of Formula Ia, Ib, or IIa wherein $R^1$ is $C_1$ to $C_6$ haloalkyl, or $C_1$ to $C_4$ haloalkyl, such as $CF_3$.

In certain embodiments, the compound is of Formula Ia, Ib, or IIa wherein $R^2$ is $C_1$ to $C_6$ alkyl, such as $CH_3$.

In certain embodiments, the compound is of Formula Ia, Ib, or IIa wherein $R^2$ is $C_1$ to $C_6$ alkyl, such as $CH_3$ or $CH(CH_3)_2$ and $R^1$ is hydrogen.

In certain embodiments, the compound is of Formula Ia, Ib, or IIa wherein $R^1$ is $C_1$ to $C_6$ alkyl, such as $CH_3$ or $CH(CH_3)_2$ and $R^2$ is hydrogen.

In certain embodiments, the compound is of Formula Ia, Ib, or IIa wherein $R^2$ is $C_1$ to $C_6$ alkyl, such as $CH(CH_3)_2$ and $R^1$ is $CH_3$.

In certain embodiments, the compound is of Formula Ia, Ib, or IIa wherein $R^3$ is $C_1$ to $C_6$ alkyl, such as $CH_3$.

In certain embodiments, the compound is of Formula Ia, Ib, or IIa wherein $R^2$ is $C_1$ to $C_6$ haloalkyl, such as $CF_3$.

In certain embodiments, the compound is of Formula Ia, Ib, or IIa wherein $R^1$ is halo, such as F.

In certain embodiments, the compound is of Formula Ia, Ib, or IIa wherein $R^2$ is halo, such as F.

In certain embodiments, the compound is of Formula Ia, Ib, or IIa wherein one of $R^3$ is H or both $R^3$ are H.

In certain embodiments, the compound is of Formula Ia, Ib, or IIa wherein $R^3$ is $C_1$ to $C_6$ haloalkyl, such as $CF_3$.

In certain embodiments, the compound is of Formula Ia, Ib or IIa wherein $R^3$ is halo, such as F.

In certain embodiments, the compound is of Formula Ia, Ib, or IIa wherein one of $R^2$ is halo, such as Cl.

In certain embodiments, the compound is of Formula Ia, Ib, or IIa wherein $R^1$ is H.

In certain embodiments, the compound is of Formula Ia, Ib, or IIa wherein $R^1$ is $OSO_3H$.

In certain embodiments, the compound is of Formula Ia, Ib, or IIa wherein one of $R^2$ is $OSO_3H$.

In certain embodiments, the compound is of Formula Ia, Ib, or IIa wherein $B^2$ or $B^1$ independently is $C-OSO_3H$.

In certain embodiments, the compound is of Formula Ia, Ib, or IIa wherein $B^2$ or $B^1$ independently is $C-SO-(CR^6_3)_m$, such as m=1 and $R^6$ is alkyl or aryl.

In certain embodiments, the compound is of Formula Ia, Ib, or IIa wherein one of $R^2$ or $R^1$ independently is cyano.

In certain embodiments, the compound is of Formula Ia, Ib, or IIa wherein $R^1$ is sulfonyloxy, such as $OSO_2Ph$.

In certain embodiments, the compound is of Formula Ia, Ib, or IIa wherein $R^1$ is sulfonyloxy, such as $OSO_2CH_3$.

In certain embodiments, the compound is of Formula Ia, Ib, or IIa wherein $R^1$ is sulfonyloxy, such as $OSO_2CF_3$.

In certain embodiments, the compound is of Formula Ia, Ib, or IIa wherein one of $R^2$ is sulfonyloxy, such as $OSO_3H$.

In certain embodiments, the compound is of Formula Ia, Ib, or IIa wherein one of $R^2$ is sulfonyloxy, such as $OSO_2Ph$.

In certain embodiments, the compound is of Formula Ia, Ib, or IIa wherein one of $R^2$ is sulfonyloxy, such as $OSO_2CH_3$.

In certain embodiments, the compound is of Formula Ia, Ib, or IIa wherein one of $R^2$ is sulfonyloxy, such as $OSO_2CF_3$.

In certain embodiments, the compound is of Formula Ia, Ib, or IIa wherein one of $R^2$ is $CH(CH_3)_2$.

In certain embodiments, the compound is of Formula Ia, Ib, or IIa wherein $R^1$ is $CH(CH_3)_2$.

In certain embodiments, the compound is of Formula Ia or IIa wherein W is =C— and Y is =N—.

In certain embodiments, the compound is of Formula Ia or IIa wherein W is =N— and Y is =C—.

In certain embodiments, the compound is of Formula Ia or IIa wherein $X^1$ is O, $X^2$ and $Z^1$ are N, $Z^2$ is $NR^5$, W is =C—, Y is =C—, $R^1$ is $CH_3$, $R^2$, $R^3$, and $R^4$ are H, and $B^1$ and $B^2$ are CH.

In certain embodiments, the compound is of Formula Ia, or IIa wherein $X^1$ is O, $X^2$ and $Z^1$ are N, $Z^2$ is $NR^5$, W is =C—, Y is =C—, $R^1$ is $CH_3$, $R^2$, $R^3$, and $R^4$ are H, $B^1$ and $B^2$ are CH, and $R^5$ is (p-$OCH_3$)Ph.

In certain embodiments, the compound is of Formula Ia or IIa wherein $X^1$ is O, $X^2$ and $Z^1$ are N, $Z^2$ is $NR^5$, Y is =C—, $R^1$ is $CH_3$, $R^2$, $R^3$, and $R^4$ are H, $B^1$ and $B^2$ are CH, and $R^5$ is Ph.

In certain embodiments, the compound is of Formula Ia, or IIa wherein $X^1$ is O, $X^2$ and $Z^1$ are N, $Z^2$ is $NR^5$, W is =C—, Y is =C—, $R^1$ is $CH_3$, $R^2$, $R^3$, and $R^4$ are H, $B^1$ and $B^2$ are CH, and $R^5$ is (o-Cl)Ph.

In certain embodiments, the compound is of Formula Ia or IIa wherein $X^1$ is O, $X^2$ and $Z^1$ are N, $Z^2$ is $NR^5$, W is =C—, Y is =C—, $R^1$ is $CH_3$, $R^2$, $R^3$, and $R^4$ are H, $B^1$ and $B^2$ are CH, and $R^5$ is (m-$CO_2CH_3$)Ph.

In certain embodiments, the compound is of Formula Ia or IIa wherein $X^1$ is O, $X^2$ and $Z^1$ are N, $Z^2$ is $NR^5$, W is =C—, Y is =C—, $R^1$ is $CH_3$, $R^2$, $R^3$, and $R^4$ are H, $B^1$ and $B^2$ are CH, and $R^5$ is (m-$SO_3H$)Ph.

In certain embodiments, the compound is of Formula Ia or IIa wherein $X^1$ is O, $X^2$ and $Z^1$ are N, $Z^2$ is $NR^5$, W is =C—, Y is =C—, $R^1$ is $CH_3$, $R^2$, $R^3$, and $R^4$ are H, $B^1$ and $B^2$ are CH, and $R^5$ is $CH_3$.

In certain embodiments, the compound is of Formula Ia or IIa wherein $X^1$ is O, $X^2$ and $Z^1$ are N, $Z^2$ is $NR^5$, W is =C—, Y is =C—, $R^1$ is $CH_3$, and $R^3$ is $CF_3$, $R^2$ and $R^4$ are H, $B^1$ and $B^2$ are CH, and $R^5$ is $CH_3$.

In certain embodiments, the compound is of Formula Ia or IIa wherein $X^1$ is O, $X^2$ and $Z^1$ are N, $Z^2$ is $NR^5$, W is =C—, Y is =C—, $R^1$ is $CF_3$, $R^2$, $R^3$, and $R^4$ are H, $B^1$ and $B^2$ are CH, and $R^5$ is H.

In certain embodiments, the compound is of Formula Ib or IIb wherein $B^2$ is N and $B^1$ is CH.

In certain embodiments, the compound is of Formula Ib or IIb wherein $B^2$ is CH and $B^1$ is N.

In certain embodiments, the compound is of Formula Ib or IIb wherein $B^2$ is N and $B^1$ is N.

In certain embodiments, the compound is of Formula Ia, Ib, IIa or IIb wherein n is 1.

In certain embodiments, the compound is of Formula Ia, Ib, IIa or IIb wherein n is 2. In some embodiments, n is 0.

In certain embodiments, the compound is of Formula Ia, Ib, IIa or IIb wherein p is 2. In some embodiments, p is 3.

In certain embodiments, the compound is of Formula Ia, Ib, IIa or IIb wherein q is 0. In some embodiments, q is 1. In some embodiments, q is 2.

In certain embodiments, the compound is of Formula Ib or IIb wherein $R^1$ is a $C_1$ to $C_6$ alkyl, such as $CH_3$.

In certain embodiments, the compound is of Formula Ib or IIb wherein $R^1$ is a $C_1$ to $C_6$ haloalkyl, such as $CF_3$.

In certain embodiments, the compound is of Formula Ib or IIb wherein one of $R^2$ is a $C_1$ to $C_6$ alkyl, such as $CH_3$.

In certain embodiments, the compound is of Formula Ib or IIb wherein one of $R^2$ is a $C_1$ to $C_6$ haloalkyl, such as $CF_3$.

In certain embodiments, the compound is of Formula Ib or IIb wherein $R^1$ is a halogen, such as F.

In certain embodiments, the compound is of Formula Ib or IIb wherein one of $R^2$ is a halogen, such as F.

In certain embodiments, the compound is of Formula Ib or IIb wherein one of $R^3$ is H or both $R^3$ are H.

In certain embodiments, the compound is of Formula Ib or IIb wherein at least one of $R^3$ is a $C_1$ to $C_6$ alkyl, such as $CH_3$.

In certain embodiments, the compound is of Formula Ib or IIb wherein at least one of $R^3$ is a $C_1$ to $C_6$ haloalkyl, such as $CF_3$.

In certain embodiments, the compound is of Formula Ib or IIb wherein at least one of $R^3$ is a halogen, such as F.

In certain embodiments, the compound is of Formula Ib or IIb wherein at least one of $R^2$ is a halogen, such as Cl.

In certain embodiments, the compound is of Formula Ib or IIb wherein $R^1$ is H and $R^2$ is H.

In certain embodiments, the compound is of Formula Ib or IIb wherein $R^1$ is H and $R^2$ is a $C_1$ to $C_6$ alkyl, such as $CH_3$.

In certain embodiments, the compound is of Formula Ib or IIb wherein $R^1$ is $OSO_3H$.

In certain embodiments, the compound is of Formula Ib or IIb wherein one of $R^2$ is $OSO_3H$.

In certain embodiments, the compound is of Formula Ib or IIb wherein $R^1$ is a sulfonyloxy, such as $OSO_2Ph$.

In certain embodiments, the compound is of Formula Ib or IIb wherein $R^1$ is a sulfonyloxy, such as $OSO_2CH_3$.

In certain embodiments, the compound is of Formula Ib or IIb wherein $R^1$ is a sulfonyloxy, such as $OSO_2CF_3$.

In certain embodiments, the compound is of Formula Ib or IIb wherein one of $R^2$ is $OSO_3H$.

In certain embodiments, the compound is of Formula Ib or IIb wherein one of $R^2$ is a sulfonyloxy, such as $OSO_2Ph$.

In certain embodiments, the compound is of Formula Ib or IIb wherein one of $R^2$ is a sulfonyloxy, such as $OSO_2CH_3$.

In certain embodiments, the compound is of Formula Ib or IIb wherein one of $R^2$ is a sulfonyloxy, such as $OSO_2CF_3$.

In certain embodiments, the compound is of Formula Ib or IIb wherein at least one of $R^2$ is a $C_1$ to $C_6$ alkyl, such as $CH_3$ or $CH(CH_3)_2$.

In certain embodiments, the compound is of Formula Ib or IIb wherein $R^1$ is a $C_1$ to $C_6$ alkyl, such as $CH_3$ or $CH(CH_3)_2$.

In certain embodiments, the compound is of Formula Ib or IIb wherein L is C=O.

In some embodiments, the compound is of Formula Ib or IIb wherein L is —C≡C—. In some embodiments, the compound is of Formula Ib or IIb wherein L is —$CR^6$=$CR^6$—. In some embodiments, $R^6$ is H. In some embodiments, the compound is of Formula Ib or IIb wherein L is cyclopropyl.

In some embodiments, the compound is of Formula Ib or IIb wherein k is 0. In some embodiments, k is 1 and $CR^3{}_2$ is $CH_2$, C=O, $CHCH_3$ or $C(CH_3)_2$.

In certain embodiments, the compound is of Formula Ib or IIb wherein L is $CH_2$.

In certain embodiments, the compound is of Formula Ib or IIb wherein L is $CHR^6$, wherein is $R^6$ is a substituted $C_1$ to $C_6$ alkyl, such as $(CH_2)_2(CHOH)CH_3$.

In certain embodiments, the compound is of Formula Ib or IIb wherein one or both $R^7$ are H.

In certain embodiments, the compound is of Formula Ib or IIb wherein one of $R^7$ is $NH(CO)NH_2$.

In certain embodiments, the compound is of Formula Ib or IIb wherein one of $R^7$ is $NH(CS)NH_2$.

In certain embodiments, the compound is of Formula Ib or IIb wherein two $R^7$ together with the carbon attached thereto form C=NH.

In certain embodiments, the compound is of Formula Ib or IIb wherein two $R^7$ together with the carbon attached thereto form C=O.

In certain embodiments, the compound is of Formula Ib or IIb wherein two $R^7$ together with the carbon attached thereto form C=S.

In certain embodiments, the compound is of Formula Ib or IIb wherein one of $R^7$ is $NHR^{10}$.

In certain embodiments, the compound is of Formula Ib or IIb wherein one of $R^7$ is $SO_2R^6$, such as $SO_3CH_3$.

In certain embodiments, the compound is of Formula Ib or IIb wherein one of $R^7$ is $SO_2R^6$, such as $SO_3H$.

In certain embodiments, the compound is of Formula Ib or IIb wherein one of $R^7$ is $SR^{10}$.

In certain embodiments, the compound is of Formula Ib or IIb wherein one of $R^7$ is $C_1$ to $C_6$ haloalkyl, such as $CF_3$.

In certain embodiments, the compound is of Formula Ib or IIb wherein one of $R^7$ is sulfonyloxy, such as $OSO_2Ph$.

In certain embodiments, the compound is of Formula Ib or IIb wherein one of $R^7$ is sulfonyloxy, such as $OSO_2CH_3$.

In certain embodiments, the compound is of Formula Ib or IIb wherein one of $R^7$ is sulfonyloxy, such as $OSO_2CF_3$.

In certain embodiments, the compound is of Formula Ib or IIb wherein one of $R^7$ is $C_1$ to $C_6$ alkyl, such as $CH_3$, $CH_2CH_3$, or $CH(CH_3)_2$.

In certain embodiments, the compound is of Formula Ib or IIb wherein $X^2$ and $Z^1$ are N, $Z^2$ is $NR^5$, $B^1$ and $B^2$ are CH, L is $CH_2$—$CH_2$, $R^7$ is H, $R^5$ is $CH_3$, $R^1$ is $CH_3$, $R^2$ is H, $R^3$ is =O, $R^4$ is H, k is 1, q is 4, p is 1, m is 1, and n is 1.

In certain embodiments, the compound is of Formula Ib or IIb wherein $X^2$ and $Z^1$ are N, $Z^2$ is $NR^5$, $B^1$ and $B^2$ are CH, L is $CH_2$, $R^7$ is H, $R^5$ is $CH_3$, $R^1$ is $CH_3$, $R^2$ is H, two $R^3$ on the same carbon together with the carbon attached thereto form =O, $R^4$ is H, k is 1, q is 4, p is 1, m is 1, and n is 1.

In certain embodiments, the compound is of Formula Ib or IIb wherein $X^2$ and $Z^1$ are N, $Z^2$ is $NR^5$, $B^1$ and $B^2$ are CH, L is $CH_2$—$CH_2$, $R^7$ is H, $R^5$ is $CH_3$, $R^1$ is $CH_3$, $R^2$ is H, $R^3$ is H, $R^4$ is H, k is 1, q is 4, p is 1, m is 1, and n is 1.

In certain embodiments, the compound is of Formula Ib or IIb wherein $X^2$ and $Z^1$ are N, $Z^2$ is $NR^5$, $B^1$ and $B^2$ are CH, L is $CH_2$, $R^7$ is H, $R^5$ is $CH_3$, $R^1$ is $CH_3$, $R^2$ is H, $R^3$ is H, $R^4$ is H, k is 1, q is 4, p is 1, m is 1, and n is 1.

In certain embodiments, the compound is of Formula Ib or IIb wherein $X^2$ and $Z^1$ are N, $Z^2$ is $NR^5$, $B^1$ and $B^2$ are CH, L is CO, $R^7$ is H, $R^5$ is $CH_3$, $R^1$ is $CH_3$, $R^2$ is H, $R^3$ is H, $R^4$ is H, k is 1, q is 4, p is 1, m is 1, and n is 1.

In certain embodiments, the compound is of Formula Ib or IIb wherein $X^2$ and $Z^1$ are N, $Z^2$ is $NR^5$, $B^1$ and $B^2$ are CH, L is $CH_2$—CO, $R^7$ is H, $R^5$ is $CH_3$, $R^1$ is $CH_3$, $R^2$ is H, $R^3$ is —H, $R^4$ is H, k is 1, q is 4, p is 1, m is 1, and n is 1.

In certain embodiments, the compound is of Formula Ib or IIb wherein $X^2$ and $Z^1$ are N, $Z^2$ is $NR^5$, $B^1$ and $B^2$ are CH, L is $CH_2$, two $R^7$ together with the carbon attached thereto form C=O, $R^5$ is $CH_3$, $R^1$ is $CH_3$, $R^2$ is H, $R^3$ is H, $R^4$ is H, k is 1, q is 4, p is 1, m is 1, and n is 1.

In certain embodiments, the compound is of Formula Ib or IIb wherein $X^2$ and $Z^1$ are N, $Z^2$ is $NR^5$, $B^1$ and $B^2$ are CH, L is $CH_2$—$CH_2$, two $R^3$ on the same carbon together with the carbon attached thereto form C=O, $R^5$ is $CH_3$, $R^1$ is $CH_3$, $R^2$ is H, $R^3$ is H, $R^4$ is H, k is 1, q is 4, p is 1, m is 1, and n is 1.

In certain embodiments, the compound is of Formula Ib or IIb wherein $X^2$ and $Z^1$ are N, $Z^2$ is $NR^5$, $B^1$ and $B^2$ are CH, L is CO, two $R^7$ together with the carbon attached thereto form C=O, $R^5$ is $CH_3$, $R^1$ is $CH_3$, $R^2$ is H, $R^3$ is H, $R^4$ is H, k is 1, q is 4, p is 1, m is 1, and n is 1.

In certain embodiments, the compound is of Formula Ib or IIb wherein $X^2$ and $Z^1$ are N, $Z^2$ is $NR^5$, $B^1$ and $B^2$ are CH, L is $CH_2$—CO, two $R^7$ together with the carbon attached thereto form CO, $R^5$ is $CH_3$, $R^1$ is $CH_3$, $R^2$ is H, $R^3$ is H, $R^4$ is H, k is 1, q is 4, p is 1, m is 1, and n is 1.

In certain embodiments, the compound is of Formula IIIa or IIIb wherein $B^1$ is N and $B^2$ is N.

In certain embodiments, the compound is of Formula IIIa or IIIb wherein $B^1$ is CH and $B^2$ is N.

In certain embodiments, the compound is of Formula IIIa or IIIb wherein two $R^7$ together with the carbon attached thereto form $C=NR^{10}$, wherein $R^{10}$ is $-C(O)NH_2$, and $B^1$ is CH and $B^2$ is CH.

In certain embodiments the compound is of Formula IIIa or IIIb wherein, $R^1$ and $R^2$ independently are hydrogen or $C_1$ to $C_6$ alkyl, such as $CH_3$, $CH_2CH_3$, or $CH(CH_3)_2$. In some embodiments, $R^1$ is or $C_1$ to $C_6$ alkyl.

In certain embodiments the compound is of Formula IIIa or IIIb wherein, $R^1$ and $R^2$ independently are hydrogen or nitro.

In certain embodiments the compound is of Formula IIIa or IIIb wherein, $R^1$ and $R^2$ independently are hydrogen or alkoxy.

In certain embodiments the compound is of Formula IIIa or IIIb wherein, $R^5$ is carboxyl ester.

In certain embodiments the compound is of Formula IIIa or IIIb wherein, $R^5$ is $C_1$ to $C_6$ alkyl, such as $CH_3$, $CH_2CH_3$, or $CH(CH_3)_2$. In some embodiments, $R^5$ is phenyl. In some embodiments, $R^5$ is acyl, such as $C_1$ to $C_6$ alkylCO—, or $CH_3CO$—.

In certain embodiments the compound is of Formula IIIa or IIIb wherein, $R^3$ is $C_1$ to $C_6$ alkyl, such as $CH_3$, $CH_2CH_3$, or $CH(CH_3)_2$.

In certain embodiments the compound is of Formula IIIa or IIIb wherein, $R^4$ is hydrogen, alkyl, substituted alkyl, alkoxy, trifluoromethane, sulfonyl, sulfinyl, nitro, carboxyl, or carboxyl ester.

In some embodiments of formula Ia, Ib, IIa, IIb, IIIa or IIIb the variables m, n and q independently are 0, 1, 2 or 3 and p is 0, 1, 2, 3 or 4. In some embodiments, m, n and q independently are 0, 1 or 2.

In certain embodiments, the invention relates to compounds of Formula IV

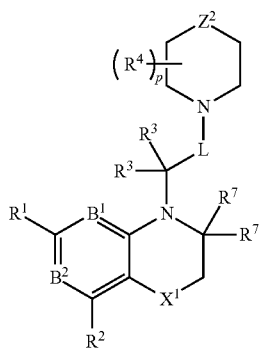

wherein:
$X^1$, L, p, $B^1$ and $B^2$ are as defined herein, such as in formula Ib, IIb, or IIIb;
$Z^2$ is $NR^5$, O, S, SO or $SO_2$;
$R^1$ and $R^2$ are independently hydrogen, $C_1$ to $C_6$ alkyl, $C_1$ to $C_6$ haloalkyl, $C_1$ to $C_6$ alkoxy, $C_1$ to $C_6$ haloalkoxy, halo, cyano, or nitro; and
$R^3$ are independently hydrogen or $C_1$ to $C_6$ alkyl; or two $R^3$ together with the carbon attached thereto form C=O;
$R^4$ are independently $C_1$ to $C_6$ alkyl; or two $R^4$ together with the carbon attached thereto form C=O;
$R^5$ is hydrogen, $C_1$ to $C_6$ alkyl, substituted $C_1$ to $C_6$ alkyl, aryl, or acyl; and
$R^7$ are independently hydrogen or $C_1$ to $C_6$ alkyl; or two $R^7$ together with the carbon attached thereto form C=O;

or a tautomer and/or a pharmaceutically acceptable salt thereof.

In certain embodiments, the compound is of Formula Ia, Ib, IIa, IIb, IIIa, IIIb, or IV wherein $Z^2$ is $CR^{10}R^5$. In some embodiments, $Z^2$ is $NR^5$. In some embodiments, $Z^2$ is O. In some embodiments, $Z^2$ is S. In some embodiments, $Z^2$ is SO. In some embodiments, $Z^2$ is $SO_2$.

In certain embodiments, the invention relates to compounds of Formula V or VI or a tautomer and/or a pharmaceutically acceptable salt thereof, wherein the variables are as defined in formula IV:

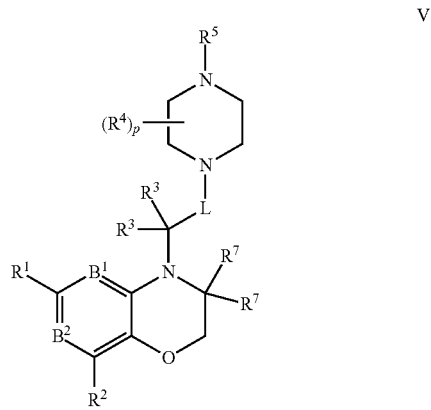

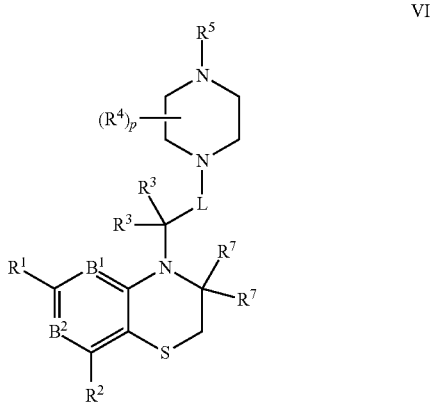

In some embodiments of formula IV, V or VI, p is 0. In some embodiments, m, n and q independently are 0, 1 or 2.

In some embodiments of formula IV, V or VI, $R^3$ are independently hydrogen or $C_1$ to $C_6$ alkyl. In some embodiments, L is $CH_2$. In some embodiments, L is $CH_2CH_2$.

In some embodiments of formula IV, V or VI, two $R^3$ together with the carbon attached thereto form C=O. In some embodiments, L is $CH_2$. In some embodiments, L is $CH_2CH_2$.

In some embodiments of formula IV, V or VI, $R^3$ are independently hydrogen or alkyl and L is C=O. In some embodiments, $R^3$ are independently hydrogen or alkyl and L is $CH_2C=O$.

In some embodiments of formula IV, V or VI, $R^5$ is $C_1$ to $C_6$ alkyl. In some embodiments, $R^5$ is methyl, ethyl, propyl, or isopropyl. In some embodiments, $R^5$ is substituted $C_1$ to $C_6$ alkyl. In some embodiments, $R^5$ is $C_1$ to $C_6$ alkyl substituted hydroxy. In some embodiments, $R^5$ is $C_1$ to $C_3$ alkyl substituted one hydroxy. In some embodiments, $R^5$ is alkyl-C(O)—. In some embodiments, $R^5$ is substituted alkyl-C(O)—. In some embodiments, $R^5$ is phenyl. In some embodiments of formula IV, V or VI, $R^{10}$ is hydrogen.

In one embodiment, provided herein is a compound of claim 1 of formula VIIb:

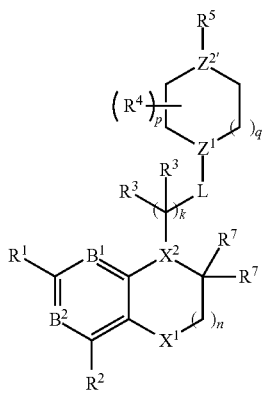

VIIb wherein, preferably, $R^1$ is selected from $C_1$-$C_6$ alkyl, $R^2$ is hydrogen, $Z_1$ and $Z_2$ are N, k, n, p. and q are 1, $R^5$ is $C_1$-$C_6$ alkyl optionally substituted with a hydroxy group, more preferably, methyl. isopropyl and 1-hydroxyethyl, and the remaining variables are as defined in any aspect or embodiment above.

In one embodiment, the compound of formula Ic or Id is selected from:

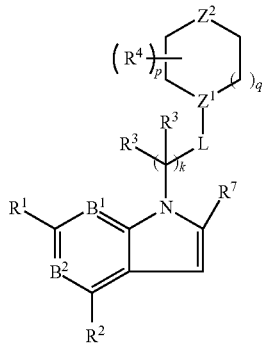

IIIc

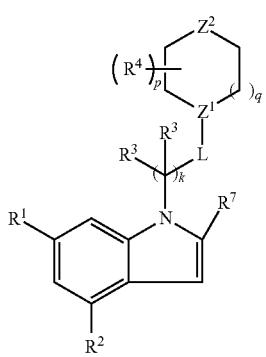

IVc

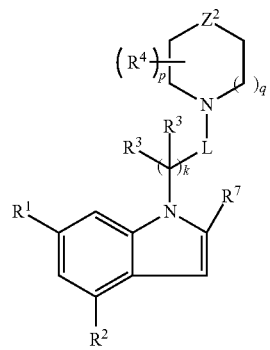

Vc

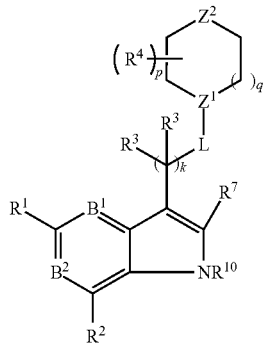

IIId

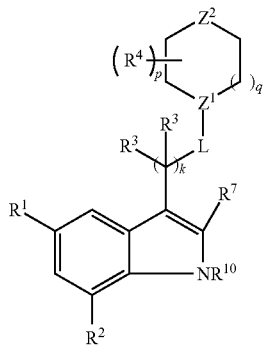

IVd

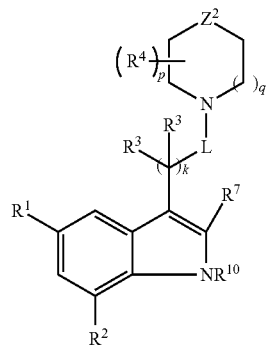

Vd wherein the variables are defined as in any aspect or embodiment herein.

Compounds of the include but are not limited to compounds of formula VIIa:

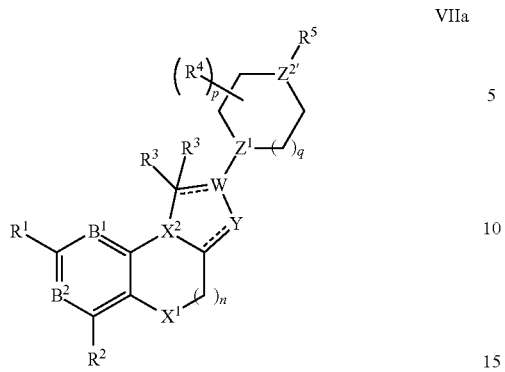
VIIa
selected from the group consisting of

| Compound No. | R¹ | R² | R³/R³' | R⁴ | R⁵ | X² | X¹ | B¹ | B² | Y | W | Z¹ | Z² | n | p | q |
|---|---|---|---|---|---|---|---|---|---|---|---|---|---|---|---|---|
| 1 | —CH₃ | —H | —H/—H | —H | —CH₃ | N | O | CH | CH | =CH— | =C— | N | N | 1 | 4 | 1 |
| 2 | —CH₃ | —H | —H/—H | —H | —CH₃ | N | O | CH | CH | =CH— | =CH— | N | N | 1 | 4 | 1 |
| 3 | —CH₃ | —H | —H/—H | —H | —CH₃ | N | O | CH | CH | —CH₂— | —CH— | N | N | 1 | 4 | 1 |
| 4 | —CH₃ | —H | —H/—H | —H | —CH₃ | N | O | CH | CH | =N— | =C— | N | N | 1 | 4 | 1 |
| 5 | —CF₃ | —H | —H/—H | —H | —CH₃ | N | O | CH | CH | =CH— | =CH— | N | N | 1 | 4 | 1 |
| 6 | —CF₃ | —H | —H/—CF₃ | —H | —CH₃ | N | O | CH | CH | =CH— | =CH— | N | N | 1 | 4 | 1 |
| 7 | —CH₃ | —H | —H/—H | —CF₃ | —CH₃ | N | O | CH | CH | =CH— | =CH— | N | N | 1 | 4 | 1 |
| 8 | —CH₃ | —H | —H/—H | —H | —CH₃ | N | S | CH | CH | —CH₂— | —CH— | N | N | 1 | 1 | 1 |
| 9 | —CH₃ | —H | —H/—CH=R⁴ | —CH=R³ | —CH₃ | N | NH | CH | CH | =CH— | =C— | N | N | 1 | 4 | 1 |
| 10 | —CH₃ | —H | —H/—CH₂—R⁴ | —CH₂—R³ | —CH₃ | N | O | CH | CH | —CH₂— | —CH— | N | N | 1 | 4 | 1 |
| 11 | —CH₂—CH₃ | —H | —H/—H | —H | —CH₃ | N | S | CH | CH | —CH₂— | —CH— | N | N | 1 | 4 | 1 |
| 12 | —CH₂—CH₃ | —H | —H/—H | —H | —CH₃ | N | O | CH | CH | =CH— | =CH— | N | N | 1 | 4 | 1 |
| 13 | —CH₂—CH₃ | —H | —H/—H | —H | —CH₃ | N | O | CH | CH | —CH₂— | —CH— | N | N | 1 | 4 | 1 |
| 14 | —CH₂—CH₃ | —H | —H/—H | —H | —CH₃ | N | O | CH | CH | =N— | =C— | N | N | 1 | 4 | 1 |
| 15 | —CH₃ | —H | —H/—H | —H | —CH₃ | N | O | CH | CH | =CH— | =CH— | N | CH | 1 | 4 | 1 |
| 16 | —CH₃ | —H | —H/—H | —H | (pCF₃)Ph | N | O | CH | CH | =CH— | =CH— | N | N | 1 | 4 | 1 |
| 17 | —CH₃ | —H | —H/—H | —H | (pCl)Ph | N | O | CH | CH | =CH— | =C— | N | N | 1 | 4 | 1 |
| 18 | —CH₃ | —H | —H/—H | —H | —CH₃ | N | O | CH | CH | —CH₂— | —CH— | N | N | 1 | 4 | 1 |
| 19 | CH(CH₃)₂ | —H | —H/—H | —H | —CH₃ | N | O | CH | CH | =N— | =C— | N | N | 1 | 4 | 1 |
| 20 | CH(CH₃)₂ | —H | —H/—H | —H | —CH₃ | N | O | CH | CH | =CH— | =CH— | N | N | 1 | 4 | 1 |
| 21 | CH(CH₃)₂ | —H | —H/—H | —H | —CH₃ | N | O | CH | CH | —CH₂— | —CH— | N | N | 1 | 4 | 1 |
| 22 | CH(CH₃)₂ | —H | —H/—H | —H | —CH₃ | N | O | CH | CH | =N— | =C— | N | N | 1 | 4 | 1 |
| 23 | CH(CH₃)₂ | —H | —H/—H | —H | —CH₃ | N | O | CH | CH | =CH— | =CH— | N | N | 1 | 4 | 1 |
| 24 | —OCH₃ | —H | —H/—H | —H | —CH₃ | N | O | CH | CH | =CH— | =C— | N | N | 1 | 4 | 1 |
| 25 | —OCH₃ | —H | —H/—H | —H | —CH₃ | N | O | CH | CH | =CH— | =CH— | N | N | 1 | 4 | 1 |
| 26 | —OCH₃ | —H | —H/—H | —H | —CH₃ | N | O | CH | CH | —CH₂— | —CH— | N | N | 1 | 4 | 1 |
| 27 | —OCH₃ | —H | —H/—H | —H | —CH₃ | N | O | CH | CH | =N— | =C— | N | N | 1 | 4 | 1 |
| 28 | —CH₃ | —Cl | —H/—H | —H | —CH₃ | N | O | CH | CH | =CH— | =CH— | N | N | 1 | 4 | 1 |
| 29 | —CH₃ | —Cl | —H/—H | —H | —CH₃ | N | O | CH | CH | =CH— | =C— | N | N | 1 | 4 | 1 |
| 30 | —CH₃ | —Cl | —H/—H | —H | —CH₃ | N | O | CH | CH | —CH₂— | —CH— | N | N | 1 | 4 | 1 |
| 31 | —CH₃ | —NO₂ | —H/—H | —H | —CH₃ | N | O | CH | CH | =CH— | =CH— | N | N | 1 | 4 | 1 |
| 32 | —CH₃ | —NO₂ | —H/—H | —H | —CH₃ | N | O | CH | CH | =CH— | =C— | N | N | 1 | 4 | 1 |
| 33 | —CH₃ | —NO₂ | —H/—H | —H | —CH₃ | N | O | CH | CH | —CH₂— | —CH— | N | N | 1 | 4 | 1 |
| 34 | —CH₃ | —NH₂ | —H/—H | —H | —CH₃ | N | O | CH | CH | =CH— | =CH— | N | N | 1 | 4 | 1 |
| 35 | —CH₃ | —NH₂ | —H/—H | —H | —CH₃ | N | O | CH | CH | =CH— | =C— | N | N | 1 | 4 | 1 |
| 36 | —CH₃ | —NH₂ | —H/—H | —H | —CH₃ | N | O | CH | CH | —CH₂— | —CH— | N | N | 1 | 4 | 1 |
| 37 | —CH₃ | —H | —H/—H | —CH₃ | —CH₃ | N | O | CH | CH | =CH— | =CH— | N | N | 1 | 4 | 1 |
| 38 | —NH₂ | —H | —H/—H | —H | —CH₃ | N | O | CH | CH | =CH— | =C— | N | N | 1 | 4 | 1 |
| 39 | —NH₂ | —H | —H/—H | —CH₃ | —CH₃ | N | O | CH | CH | =CH— | =CH— | N | N | 1 | 4 | 1 |
| 40 | —NH₂ | —H | —H/—H | —H | —CH₃ | N | O | CH | CH | —CH₂— | —CH— | N | N | 1 | 4 | 1 |
| 41 | —CH=CH—B² | —H | —H/—H | —H | —CH₃ | N | O | —CH=CH—R¹ | CH=CH—R¹ | —CH₂— | =C— | N | N | 1 | 4 | 1 |
| 42 | —CH=CH—B¹ | —H | —H/—H | —H | —CH₃ | N | S | CH | CH | —CH₂— | —CH— | N | N | 1 | 4 | 1 | or a pharmaceutically acceptable salt thereof.

Compounds of the invention include, but are not limited to, 1-(6-methyl-2,3-dihydro-4H-benzo[b][1,4]oxazin-4-yl)-3-(4-methylpiperazin-1-yl)propan-1-one;
1-(6-methyl-2,3-dihydro-4H-benzo[b][1,4]oxazin-4-yl)-2-(4-methylpiperazin-1-yl)ethan-1-one;
6-methyl-4-(3-(4-methylpiperazin-1-yl)propyl)-3,4-dihydro-2H-benzo[b][1,4]oxazine;
6-methyl-4-(2-(4-methylpiperazin-1-yl)ethyl)-3,4-dihydro-2H-benzo[b][1,4]oxazine;
2-(6-methyl-2,3-dihydro-4H-benzo[b][1,4]oxazin-4-yl)-1-(4-methylpiperazin-1-yl)ethan-1-one;
3-(6-methyl-2,3-dihydro-4H-benzo[b][1,4]oxazin-4-yl)-1-(4-methylpiperazin-1-yl)propan-1-one
6-methyl-4-(2-(4-methylpiperazin-1-yl)ethyl)-2H-benzo[b][1,4]oxazin-3(4H)-one;
6-methyl-4-(3-(4-methylpiperazin-1-yl)propyl)-2H-benzo[b][1,4]oxazin-3(4H)-one;
6-methyl-4-(2-(4-methylpiperazin-1-yl)-2-oxoethyl)-2H-benzo[b][1,4]oxazin-3(4H)-one;
And 6-methyl-4-(3-(4-methylpiperazin-1-yl)-3-oxopropyl)-2H-benzo[b][1,4]oxazin-3(4H)-one;

or their tautomers and/or a pharmaceutically acceptable salt thereof.

The following Tables 1 and 1A provide exemplary compounds according to some embodiments of the present invention.

TABLE 1

| Compound Structure | Compound Name |
|---|---|
| A | 1-(6-methyl-2,3-dihydro-4H-benzo[b][1,4]oxazin-4-yl)-3-(4-methylpiperazin-1-yl)propan-1-one |
| B | 1-(6-methyl-2,3-dihydro-4H-benzo[b][1,4]oxazin-4-yl)-2-(4-methylpiperazin-1-yl)ethan-1-one |
| C | 6-methyl-4-(3-(4-methylpiperazin-1-yl)propyl)-3,4-dihydro-2H-benzo[b][1,4]oxazine |

TABLE 1-continued

| Compound Structure | Compound Name |
|---|---|
| D | 6-methyl-4-(2-(4-methylpiperazin-1-yl)ethyl)-3,4-dihydro-2H-benzo[b][1,4]oxazine |
| E | 2-(6-methyl-2,3-dihydro-4H-benzo[b][1,4]oxazin-4-yl)-1-(4-methylpiperazin-1-yl)ethan-1-one |
| F | 3-(6-methyl-2,3-dihydro-4H-benzo[b][1,4]oxazin-4-yl)-1-(4-methylpiperazin-1-yl)propan-1-one |
| G | 6-methyl-4-(2-(4-methylpiperazin-1-yl)ethyl)-2H-benzo[b][1,4]oxazin-3(4H)-one |

TABLE 1-continued

| Compound Structure | Compound Name |
| --- | --- |
| H | 6-methyl-4-(3-(4-methylpiperazin-1-yl)propyl)-2H-benzo[b][1,4]oxazin-3(4H)-one |
| I | 6-methyl-4-(2-(4-methylpiperazin-1-yl)-2-oxoethyl)-2H-benzo[b][1,4]oxazin-3(4H)-one |
| J | 6-methyl-4-(3-(4-methylpiperazin-1-yl)-3-oxopropyl)-2H-benzo[b][1,4]oxazin-3(4H)-one |
| K | 1-(6-methyl-2,3-dihydro-4H-benzo[b][1,4]oxazin-4-yl)-2-(4-phenylpiperazin-1-yl)ethan-1-one |

TABLE 1-continued

| Compound Structure | Compound Name |
|---|---|
| L | 1-(6-methyl-2,3-dihydro-4H-benzo[b][1,4]oxazin-4-yl)-2-(1-methylpiperidin-4-yl)ethan-1-one |
| M (Comparison compound) | 1-(3-(2-chloro-5-oxido-10H-phenothiazin-10-yl)propyl)-4-methylpiperazine 1,4-dioxide |
| N (Comparison compound) | 2-(4-(3-(2-(trifluoromethyl)-10H-phenothiazin-10-yl)propyl)piperazin-1-yl)ethan-1-ol |
| O | 2-(4-cyclohexylpiperazin-1-yl)-1-(6-methyl-2,3-dihydro-1,4-benzoxazin-4-yl)ethanone |

TABLE 1-continued

| Compound Structure | Compound Name |
|---|---|
| P | 1-(6-methyl-2,3-dihydro-1,4-benzoxazin-4-yl)-2-(4-propan-2-ylpiperazin-1-yl)ethanone |
| Q | 1-[4-(2-hydroxyethyl)piperazin-1-yl]-2-(6-methyl-2,3-dihydro-1,4-benzoxazin-4-yl)ethanone |
| R | 1-[4-(2-methoxyethyl)piperazin-1-yl]-2-(6-methyl-2,3-dihydro-1,4-benzoxazin-4-yl)ethanone |
| S | N-[2-[4-[2-(6-methyl-2,3-dihydro-benzoxazin-4-yl)acetyl]piperazin-1-yl]ethyl]methanesulfonamide |

TABLE 1A

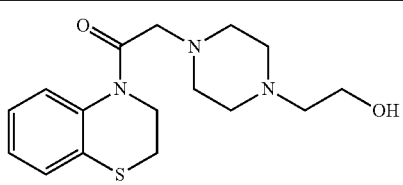 6d

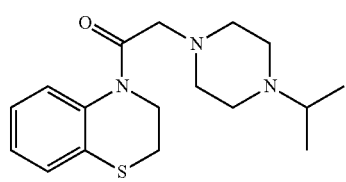 [SMILES: CC(C)N1CCN(CC(=O)N2CCSc3ccccc32)CC1] 6e

TABLE 1A-continued

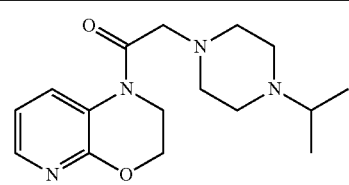 6f

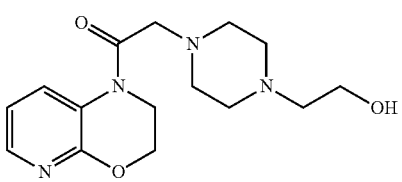 [SMILES: O=C(CN1CCN(CCO)CC1)N1CCOc2ncccc21] 6g

TABLE 1A-continued
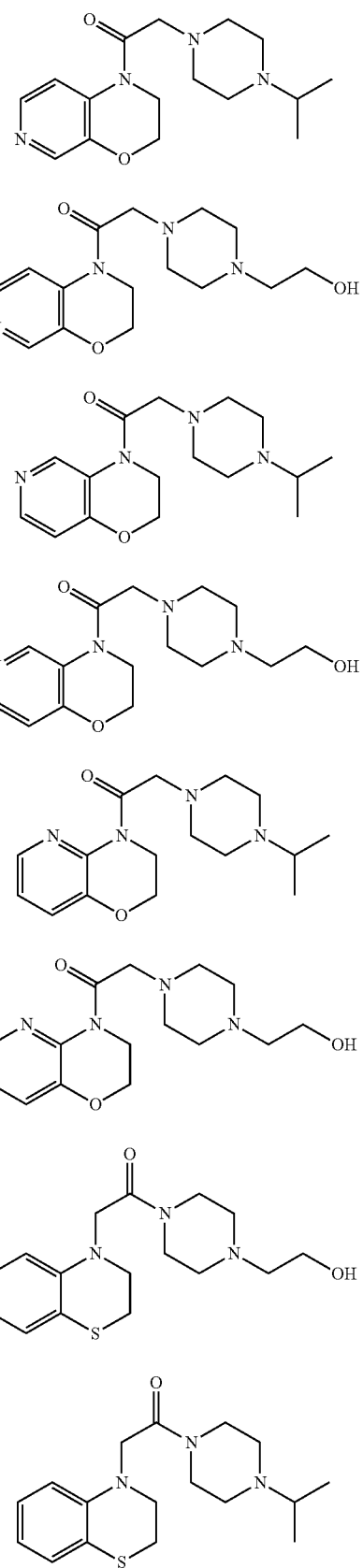
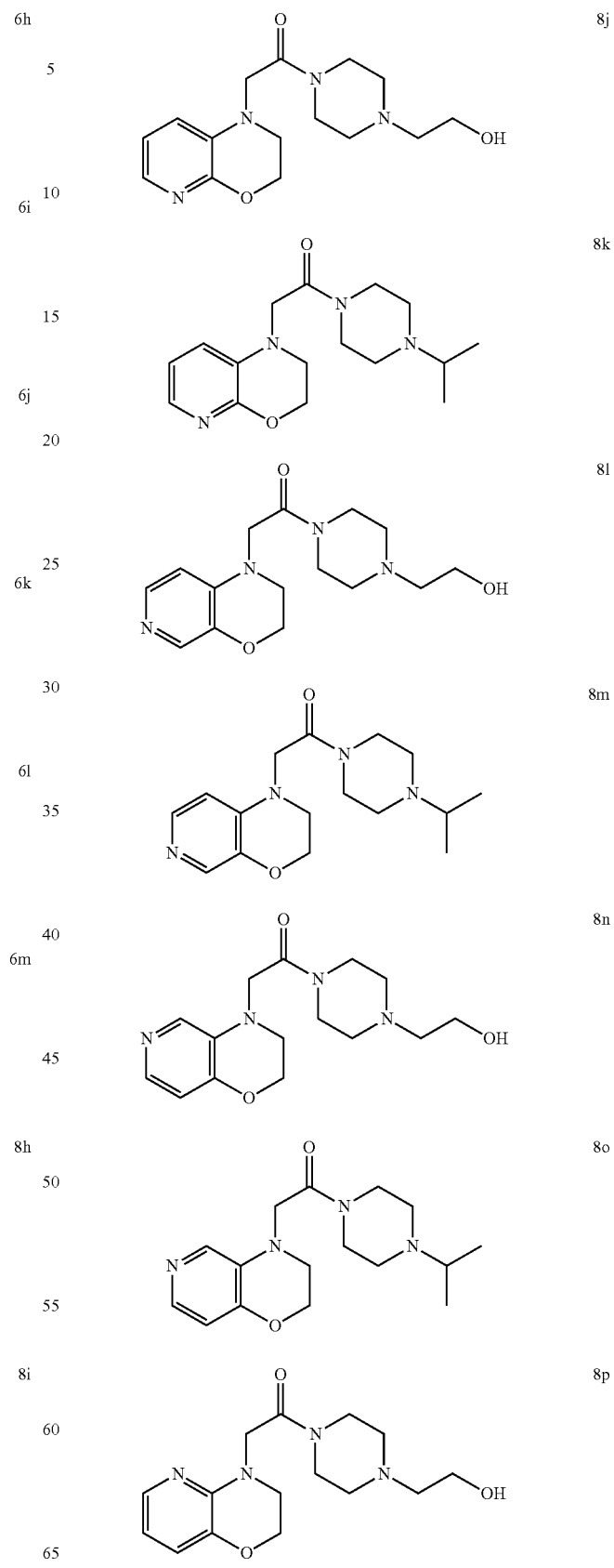

TABLE 1A-continued

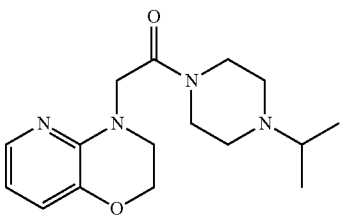 [SMILES: CC(C)N1CCN(C(=O)CN2CCOc3cccnc32)CC1]
17

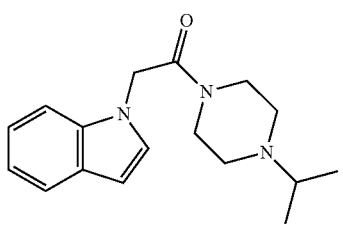 [SMILES: CC(C)N1CCN(C(=O)Cn2ccc3ccccc32)CC1]
17a

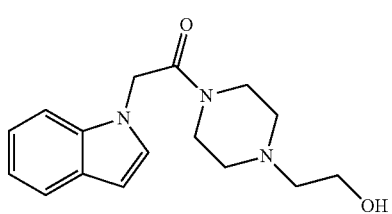 [SMILES: O=C(Cn1ccc2ccccc21)N1CCN(CCO)CC1]
18

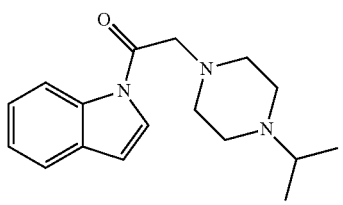 [SMILES: CC(C)N1CCN(CC(=O)n2ccc3ccccc32)CC1]
18a

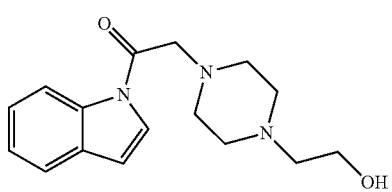 [SMILES: O=C(CN1CCN(CCO)CC1)n1ccc2ccccc21]
6c

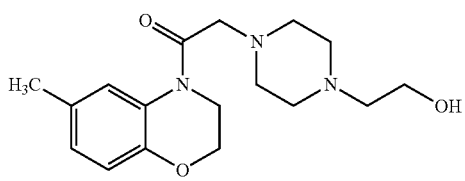 [SMILES: Cc1ccc2c(c1)N(C(=O)CN1CCN(CCO)CC1)CCO2]

3. Compositions and Methods

The compounds represented by formula Ia, Ib, IIa, IIb, IIIa, IIIb, IV, V or VI, or their tautomers and/or pharmaceutically acceptable salts thereof can effectively act as inducers of neuronal autophagy and stimulate the clearance of misfolded proteins and/or protein aggregates in cells, such as neurons, microglia and macrophages. In one aspect of the invention, the invention provides pharmaceutical compositions comprising one or more compounds of formula Ia, Ib, IIa, IIb, IIIa, IIIb, IV, V or VI and a pharmaceutically acceptable excipient. In another aspect of this invention, the invention provides a method for inducing neuronal autophagy and/or a method for treating a disease mediated at least in part by misfolded proteins and/or protein aggregates with an effective amount of one or more compound of formula Ia, Ib, IIa, IIb, IIIa, IIIb, IV, V or VI as provided herein. The compounds of the invention are useful in stimulating neuronal autophagy in the CNS as well as in peripheral immune cells. These compounds are also useful for treating peripheral infections or immune dysfunction.

In one of its method aspects, this invention is directed to a method for inducing neuronal autophagy which method comprises contacting cells (including, but not limited to, neurons, microglia, macrophages, and astrocytes) with an effective amount of one or more compound of Formula Ia, Ib, IIa, IIb, IIIa, IIIb, IV, V or VI as described herein.

In another of its method aspects, this invention is directed to a method for treating a disease mediated at least in part by the accumulation of misfolded proteins and/or protein aggregates which method comprises administering to a patient in need thereof an effective amount of one or more compounds of Formula Ia, Ib, IIa, IIb, IIIa, IIIb, IV, V or VI, or a pharmaceutical composition comprising a pharmaceutically acceptable excipient and one or more compound of Formula Ia, Ib, IIa, IIb, IIIa, IIIb, IV, V or VI as described herein.

Diseases mediated at least in part by the accumulation of misfolded proteins and/or protein aggregates include those selected from the group consisting of Huntington's disease and other polyglutamine disorders such as spinocerebellar ataxias, Alzheimer's disease, Parkinson's disease, frontotemporal dementia, high-pressure neurological syndrome, dystonia, olivopontocerebellar atrophy, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasitic, for example, poliomyelitis, Lyme disease (*Borrelia burgdorferi* infection) and malaria, cancers with cerebral localization, Tourette's syndrome, hepatic encephalopathy, systemic lupus, analgesia and opiate-withdrawal symptoms, feeding behaviour, schizophrenia, chronic anxiety, depressive disorders, disorders of the developing or aged brain, diseases of addiction, diabetes, and complications thereof. The compounds of this invention may also influence synaptogenesis after brain injury. The compounds also may influence memory. The diseases of addiction refer to addictive diseases which adversely affect or alter the neuronal function including by way of example, drug addiction such as alcoholism, nicotine addiction, illicit drug addiction (e.g., heroin, cocaine, marijuana, etc.).

The compounds of this invention are useful in the diagnosis and treatment of a variety of human diseases including neurodegenerative and neurological disorders, consequences of stroke and/or cerebral ischemia, hypoxia, multi-infarct dementia, consequences of trauma and damages to the cerebrum or spinal cord, autoimmune disease, and psychiatric illness. For example, the compounds of the present invention are particularly useful in treating neurodegenerative disorders such as Huntington's disease and other polyglutamine disorders such as spinocerebellar ataxias, Alzheimer's disease, Parkinson's disease, high-pressure neurological syndrome, dystonia, olivopontocerebellar atrophy, frontotemporal dementia, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasitic, for example, poliomyelitis, Lyme disease (Borrelia burgdorferi infection) and malaria, cancers with cerebral localization, Tourette's syndrome, hepatic encephalopathy, systemic lupus, analgesia and opiate-withdrawal symptoms, feeding behaviour, schizophrenia, chronic anxiety, depressive disorders, disorders of the developing or aged brain, diseases of addiction, all peripheral indications such as diabetes, and complications thereof. The compounds of this invention may also influence synaptogenesis after brain injury. The compounds also may influence memory.

Compounds of this invention are shown or contemplated to have improved safety and potency, such as the potency of inducing antophagy at low nanomolar concentrations. Compounds of this invention are shown or contemplated to have potency in HD patient induced pluripotent stem cell derived neurons (i-neurons). In some embodiments, the compounds have little or no neuroleptic activity.

The amount of active compound administered will vary depending upon the disease treated, the mammalian species, and the particular mode of administration, etc. Suitable doses for the compounds of the present invention can be, for example, between 0.1 mg to about 1000 mg, between 0.1 mg to about 500 mg, between 0.1 mg to about 300 mg, between 0.1 mg to about 100 mg, between 1 mg to about 500 mg, between 1 mg to about 300 mg, or between 1 mg to about 100 mg per day. Such doses can be administered once a day or more than once a day, for example 2, 3, 4, 5 or 6 times a day, but preferably 1 or 2 times per day. In some embodiments, the total dosage for a 70 kg adult is in the range of 0.001 to about 15 mg per kg weight of subject per administration or 0.01 to about 1.5 mg per kg weight of subject per administration, and such therapy can extend for a number of days, a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

4. General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

If the compounds of this invention contain one or more chiral centers, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's *Reagents for Organic Synthesis*, Volumes 1-15 (John Wiley, and Sons, 1991), *Rodd's Chemistry of Carbon Compounds*, Volumes 1-5, and Supplementals (Elsevier Science Publishers, 1989), *Organic Reactions*, Volumes 1-40 (John Wiley, and Sons, 1991), *March's Advanced Organic Chemistry*, (John Wiley, and Sons, 5$^{th}$ Edition, 2001), and *Larock's Comprehensive Organic Transformations* (VCH Publishers Inc., 1989).

In one general embodiment, the method involves reacting an appropriate benzoxazine starting material or a related compound with an electrophilic partner such as a haloacyl halide. It is appreciated that the nucleophilic component of the starting material preferentially displaces with the smaller electrophilic component, the haloacyl leaving group whilst retaining the larger electrophilic component, the alkyl halide, in order to further functionalize the molecule in a subsequent synthetic step. In principle, any such dual-functionalized electrophilic partner will work with the starting material. Preferably, but not always allowable, the electrophilic partner possesses dual, complimentary, discriminative and/or chemoselective electrophilic functionalities. Examples of dual-functionalized electrophilic compounds include, but are not limited to: bis-alkyl halides, haloacyl halides, bis-methyl esters, dialdehydes, bis-carboxylic acids, phosgene, bis-epoxides, carbonate esters, and 1,1'-Carbonyldiimidazole (CDI).

In another general embodiment, the method involves reacting an appropriately functionalized benzoxazine or a related compound, as synthesized from above, with a nucleophilic partner such as a nitrogen containing hetero- For example, the compounds of general Formula Ib, IIb and IIIb can be prepared according to Scheme 1:

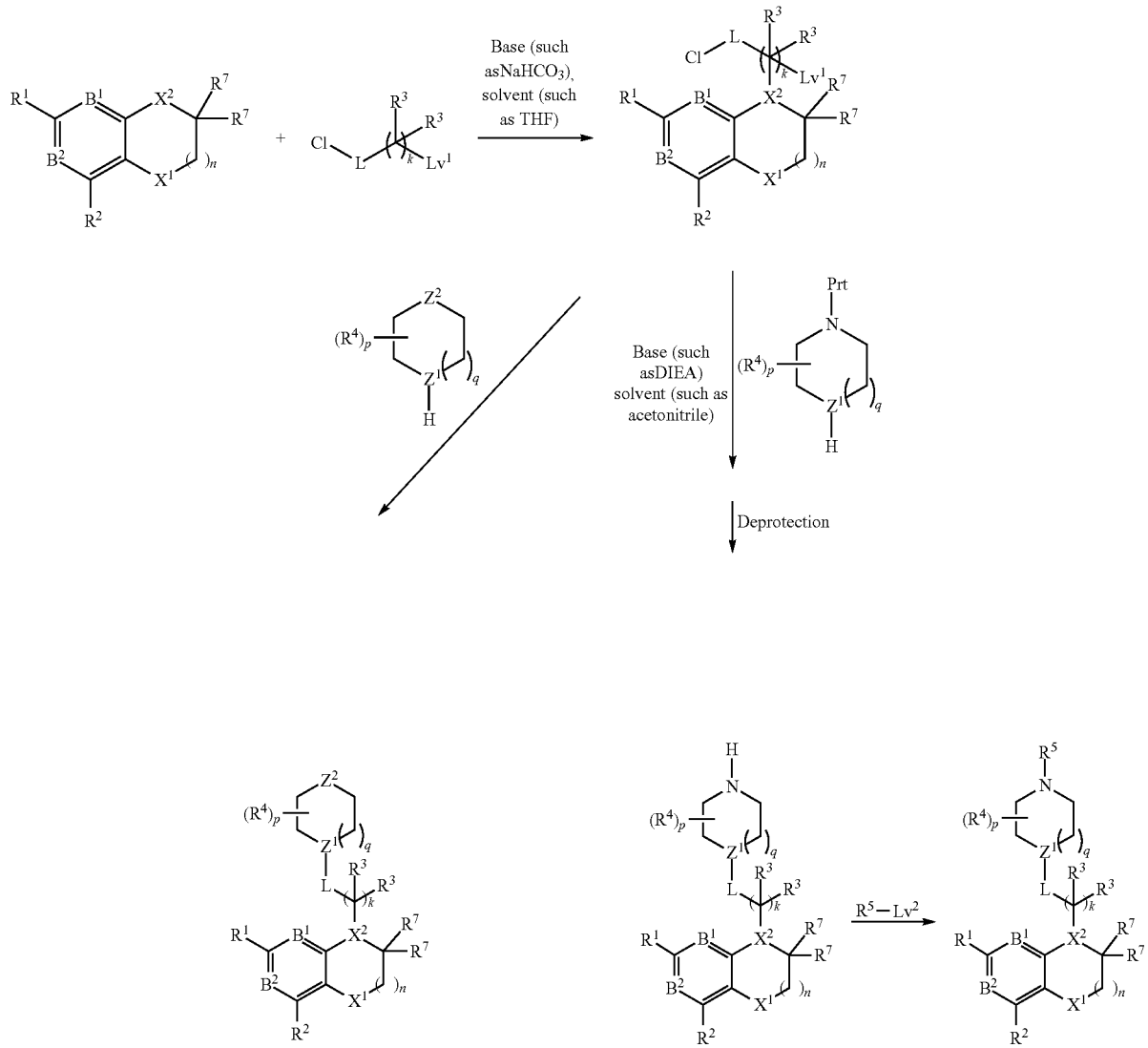

cycle. It is further appreciated that the nucleophilic partner selectively reacts at the electrophilic functionality presently attached to the benzoxazine moiety. Thus, the benzoxazine moiety should not contain any functional groups that might react further with, nor degrade in the reaction conditions with, the nucleophilic partner, or such functional group is properly protected.

In another general embodiment, the method involves reacting an appropriately functionalized benzoxazine or a related compound, as synthesized from above, with an electrophilic partner such as an alkyl halide. It is further appreciated that the electrophilic partner selectively reacts at the nucleophilic, such as the nitrogen atom of the benzoxazine moiety. Thus, the electrophilic partner should not be added under any reaction conditions that might react with any other functionality in the benzoxazine moiety.

wherein $Lv^1$ and $Lv^2$ are proper leaving groups (e.g., $Lv^1$ is Cl and $Lv^2$ is Br), Prt is an amino protecting group or hydrogen, and $R^1$-$R^5$, $R^7$, $B^1$, $B^2$, L, $X^1$, $X^2$, $Z^1$, $Z^2$, k, n, p, and q are as defined herein. Amino protecting groups and their methods of deprotection are known in the art, such as those described in T. W. Greene and P. G. M. Wuts, *Protecting Groups in Organic Synthesis*, Third Edition, Wiley, New York, 1999. When Prt is hydrogen, the deprotection step can be omitted.

In another general embodiment, the method involves reacting an appropriately functionalized benzoxazine or related starting material with an activated alkene or alkyne for a 1,3 cycloaddition reaction.

For example, the compounds of general Formula Ia can be prepared according to Scheme 2:

Scheme 2
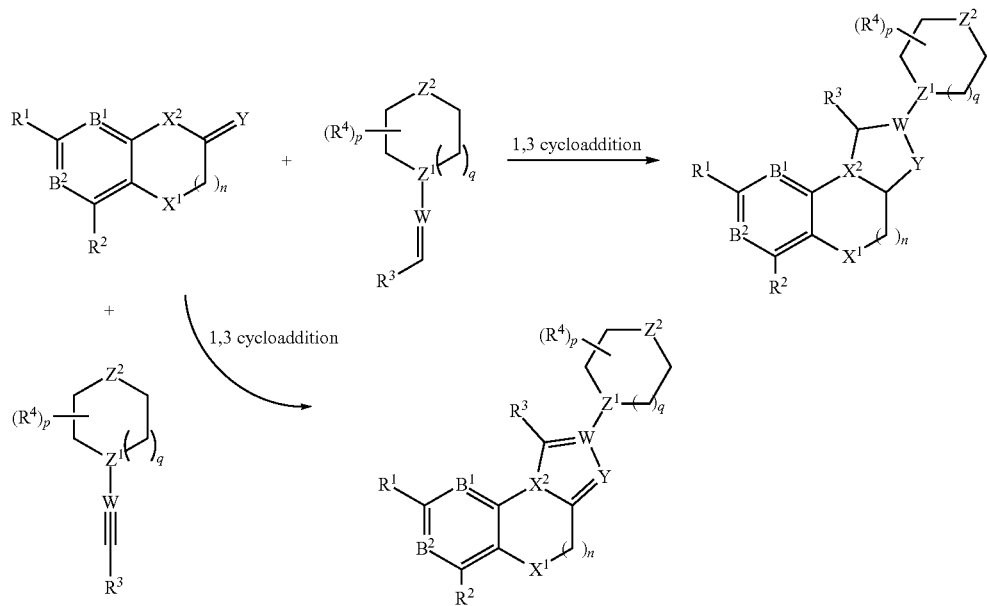
wherein $R^1$-$R^4$, Y, $B^1$, $B^2$, W, $X^1$, $X^2$, $Z^1$, $Z^2$, n, p, and q are as defined herein.
Scheme 3
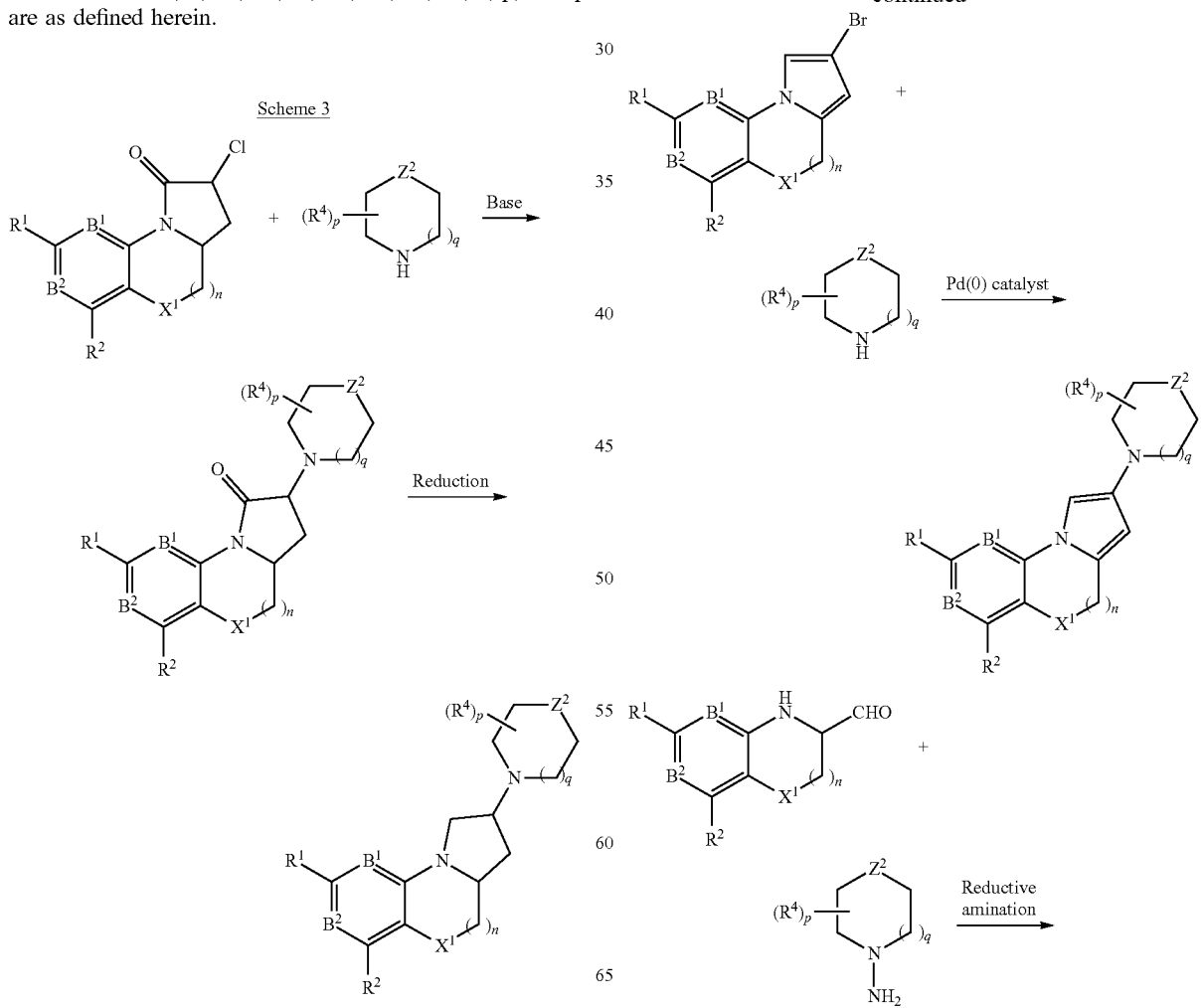

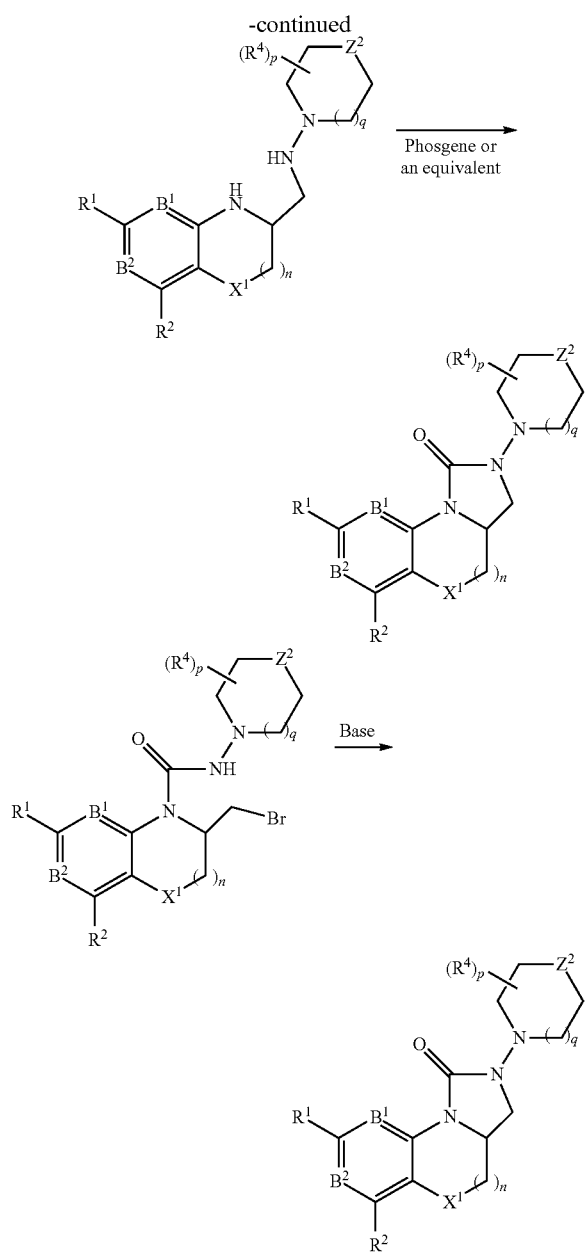

wherein $R^1$, $R^2$, $R^4$, $B^1$, $B^2$, $X^1$, $Z^2$, n, p, and q are as defined herein.

Certain other illustrative and non-limiting processes of making compounds of formula Ia are shown above in Scheme 3. Methods of making the starting materials, and the exact reagents and conditions useful according to this and other schemes are well known to the skilled artisan, or will be apparent to them based on the disclosure provided here. For example, amination of haloheteroaryls such as bromopyrroles using a variety of catalysts are well known to the skilled artisan. Obvious modifications of these methods are also within the skill of the skilled artisan.

5. Administration and Pharmaceutical Composition

The present invention provides novel compounds possessing neuronal autophagy inducing activity and, accordingly, are useful in treating disorders mediated by (or at least in part by) the accumulation of misfolded proteins and/or protein aggregates. Such diseases include, for example, Huntington's disease and other polyglutamine disorders such as spinocerebellar ataxias, Alzheimer's disease, Parkinson's disease, high-pressure neurological syndrome, dystonia, olivopontocerebellar atrophy, frontotemporal dementia, amyotrophic lateral sclerosis, multiple sclerosis, epilepsy, consequences of stroke, cerebral ischemia, hypoxia, multi-infarct dementia, consequences of cerebral trauma or damage, damage to the spinal cord, AIDS-dementia complex, viral or bacterial meningitis, general central nervous system (CNS) infections such as viral, bacterial or parasitic, for example, poliomyelitis, Lyme disease (*Borrelia burgdorferi* infection) and malaria, cancers with cerebral localization, Tourette's syndrome, hepatic encephalopathy, systemic lupus, analgesia and opiate-withdrawal symptoms, feeding behaviour, schizophrenia, chronic anxiety, depressive disorders, disorders of the developing or aged brain, diabetes, and complications thereof.

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, preferably once or twice a day.

An effective amount of such agents can readily be determined by routine experimentation, as can the most effective and convenient route of administration, and the most appropriate formulation. Various formulations and drug delivery systems are available in the art. See, e.g., Gennaro, A. R., ed. (1995) *Remington's Pharmaceutical Sciences*, 18th ed., Mack Publishing Co.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the ED50 with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

This invention is not limited to any particular composition or pharmaceutical carrier, as such may vary. In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semi-solids, powders, sustained release formulations, solutions, suspensions, elixirs, aerosols, or any other appropriate compositions. Another preferred manner for administering compounds of this invention is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of the present invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of the present invention based on the total formulation, with the balance being one or more suitable pharmaceutical excipients. Preferably, the compound is present at a level of about 1-80 wt %. Representative pharmaceutical formulations are described below.

FORMULATION EXAMPLES

The following are representative pharmaceutical formulations containing a compound of formula Ia, Ib, IIa, IIb, IIIa, IIIb, IV, V or VI.

Formulation Example 1—Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Formulation Example 2—Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Formulation Example 3—Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4—Injectable Formulation

The following ingredients are mixed to form an injectable formulation.

| Ingredient | Amount |
| --- | --- |
| compound of this invention | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| Ingredient | Amount |
| --- | --- |
| Compound of the invention | 500 mg |
| Witepsol ® H-15 | balance |

The following synthetic and biological examples are offered to illustrate this invention and are not to be construed in any way as limiting the scope of this invention. Unless otherwise stated, all temperatures are in degrees Celsius.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

In the examples below, the following abbreviations have the following meanings. If an abbreviation is not defined, it has its generally accepted meaning.

aq.=aqueous
$CaCl_2$=calcium chloride
LC-MS=liquid chromatography-mass spectrometry
MS=mass spectrometry
THF=tetrahydrofuran
$NaHCO_3$=sodium bicarbonate
DIEA=diisopropylethylamine
MS=mass spectrometry
NaH=sodium hydride
o/n=overnight
HATU=1-[Bis(dimethylamino)methylene]-1H-1,2,3-triazolo[4,5-b]pyridinium 3-oxide hexafluorophosphate
r.t.=room temperature
LAH=lithium aluminum hydride
DCM=dichloromethane
DMF=dimethylformamide
DMSO=dimethyl sulfoxide
equiv.=equivalent
EtOAc=ethyl acetate
EtOH=ethanol
g=gram
h=hours
HCl=hydrochloric acid
HCHO=formaldehyde
HPLC=high-performance liquid chromatography
HOAc=acetic acid
M=molar
m-CPBA=m-chloroperoxybenzoic acid
MeOH=methanol
mg=milligrams
mL=milliliters
mmol=millimols
mp=melting point
m/z=mass to charge ratio
NaCl=sodium chloride
$Na_2CO_3$=sodium carbonate
NMR=nuclear magnetic resonance
NaOH=sodium hydroxide
$Na_2SO_4$=sodium sulfate
TLC=thin layer chromatography
UV=ultraviolet
wt %=weight percent
µM=micromolar The following are examples of, but are not limited to, starting material used in the synthesis of compounds of the invention. These starting compounds include:

2-chloro-1-(6-methyl-2,3-dihydro-4H-benzo[b][1,4]oxazin-4-yl)ethan-1-one

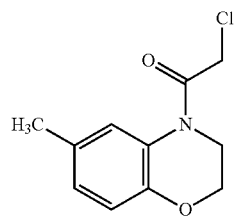

Preparation described in GB 1137796 (1968), which is herein incorporated by reference;

6-methyl-3,4-dihydro-2H-benzo[b][1,4]oxazine

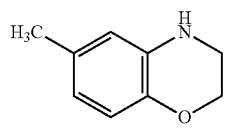

Preparation described in Synthesis (1979) (7), 541, which is herein incorporated by reference;

3,4-dihydro-2H-benzo[b][1,4]oxazine

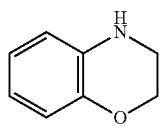

Commercially available 2-(1-methylpiperidin-4-yl)acetyl chloride

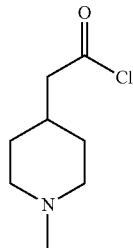

Preparation described in J. Med Chem 31, (6) 1169 (1988) and DE 3204153A1, which is herein incorporated by reference;

2-chloro-1-(2,3-dihydro-4H-benzo[b][1,4]oxazin-4-yl)ethan-1-one

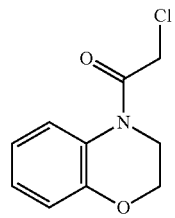 [SMILES: O=C(CCl)N1CCOc2ccccc21]

Preparation described in GB 1137796 (1968), which is herein incorporated by reference;

3-chloro-1-(4-methylpiperazin-1-yl)propan-1-one

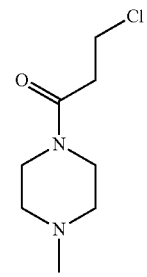

Preparation described in GB 921315 (1963), which is herein incorporated by reference.

Example 1

Preparation of 1-(6-methyl-2,3-dihydro-4H-benzo[b][1,4]oxazin-4-yl)-2-(4-methylpiperazin-1-yl)ethan-1-one

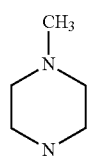

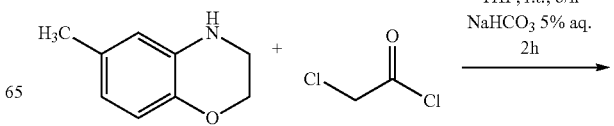

-continued

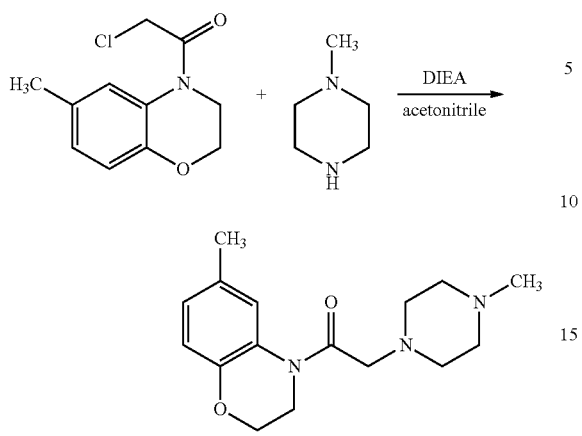

Step 1:

To a solution of 6-methyl-3,4-dihydro-2H-benzo[b][1,4]oxazine (100 mg, 0.67 mmol) in THF (5 mL) was added chloroacetyl chloride (0.083 mL, 1.05 mmol) and the reaction mixture was stirred overnight at room temperature. Then 5% NaHCO$_3$ aqueous solution (4 mL) was added and the reaction mixture was further stirred for 2 h. It was then diluted with water and extracted with ethyl acetate. Combined organic layers were washed with brine, dried with anhydrous Na$_2$SO$_4$, filtered and concentrated to give crude product 2-chloro-1-(6-methyl-2H-benzo[b][1,4]oxazin-4(3H)-yl)ethanone. Crude product was used in next step without purification.

Step 2:

To a solution of crude 2-chloro-1-(6-methyl-2H-benzo[b][1,4]oxazin-4(3H)-yl)ethanone (100 mg, 0.44 mmol) in acetonitrile (1 mL) was added diisopropylethylamine (0.115 mL, 0.66 mmol) and 1-methylpiperazine (0.049 mL, 0.44 mmol). Resulting mixture was stirred for 1 h at room temperature then concentrated in vacuo. The product was purified by HPLC-MS. $C_{16}H_{23}N_3O_2$ 290.2 (M+H)$^+$.

Example 2

Preparation of 1-(2,3-dihydro-4H-benzo[b][1,4]oxazin-4-yl)-2-(4-methylpiperazin-1-yl)ethan-1-one

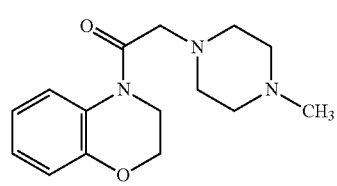 [SMILES: CN1CCN(CC(=O)N2CCOc3ccccc32)CC1]

This compound was prepared using the same procedures described for Example 1, but using 3,4-dihydro-2H-benzo[b][1,4]oxazine in place of 6-methyl-3,4-dihydro-2H-benzo[b][1,4]oxazine. MS. $C_{15}H_{21}N_3O_2$: 276.2 (M+H)$^+$.

Example 3

Preparation of 1-(6-methyl-2,3-dihydro-4H-benzo[b][1,4]oxazin-4-yl)-2-morpholinoethan-1-one

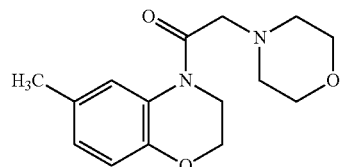

Using the procedure described above in step 2, Example 1, but using morpholine in place of N-methylpiperazine, the title compound was prepared. MS. $C_{15}H_2ON_2O_3$: 277.2 (M+H)$^+$.

Example 4

Preparation of 1-(6-methyl-2,3-dihydro-4H-benzo[b][1,4]oxazin-4-yl)-2-(4-phenylpiperazin-1-yl)ethan-1-one

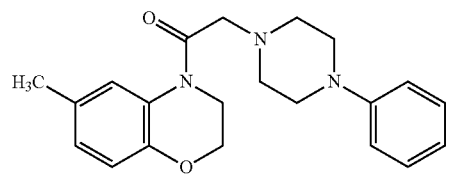 [SMILES: Cc1ccc2c(c1)N(C(=O)CN1CCN(c3ccccc3)CC1)CCO2]

Using the procedure described above in step 2, Example 1, but using N-phenylpiperazine in place of N-methylpiperazine, the title compound was prepared. MS. $C_{21}H_{25}N_3O_2$: 352.2 (M+H)$^+$.

Example 5

Preparation of 1-(6-methyl-2,3-dihydro-4H-benzo[b][1,4]oxazin-4-yl)-2-(piperazin-1-yl)ethan-1-one

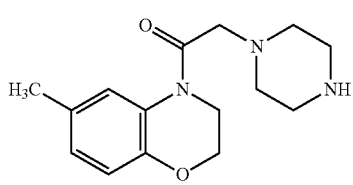 [SMILES: Cc1ccc2c(c1)N(C(=O)CN1CCNCC1)CCO2]

Using the procedure described above in step 2, Example 1, but using excess piperazine in place of N-methylpiperazine, the title compound was prepared. MS. $C_{15}H_{21}N_3O_2$ 276.2 (M+H)$^+$.

Example 6

Preparation of 2-(4-acetylpiperazin-1-yl)-1-(6-methyl-2,3-dihydro-4H-benzo[b]-[1,4]-oxazin-4-yl)ethan-1-one

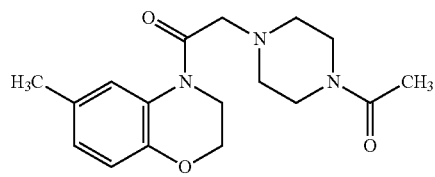 [SMILES: CC(=O)N1CCN(CC(=O)N2CCOc3ccc(C)cc32)CC1]

Using the procedure described above in step 2, Example 1, but using N-acetyl piperazine in place of N-methylpiperazine, the title compound was prepared. MS. $C_{17}H_{23}N_3O_3$ 318.2 $(M+H)^+$.

Example 6a

Preparation of 2-(4-cyclohexylpiperazin-1-yl)-1-(6-methyl-2,3-dihydro-1,4-benzoxazin-4-yl)ethanone

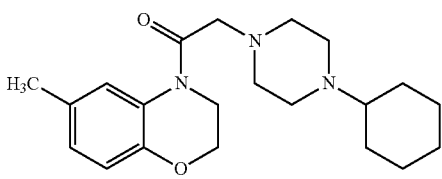 [SMILES: Cc1ccc2c(c1)N(C(=O)CN1CCN(C3CCCCC3)CC1)CCO2]

Using the procedure described above in step 2, Example 1, but using 1-cyclohexylpiperazine in place of N-methylpiperazine, the title compound was prepared. MS. $C_{21}H_{31}N_3O_2$ Exact Mass: 358.2 $(M+H)^+$.

Example 6b

Preparation of 1-(6-methyl-2,3-dihydro-1,4-benzoxazin-4-yl)-2-(4-propan-2-ylpiperazin-1-yl)ethanone

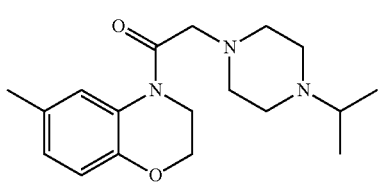 [SMILES: Cc1ccc2c(c1)N(C(=O)CN1CCN(C(C)C)CC1)CCO2]

Using the procedure described above in step 2, Example 1, but using 1-isopropylpiperazine in place of N-methylpiperazine, the title compound was prepared. MS. $C_{18}H_{27}N_3O_2$ Exact Mass: 318.2 $(M+H)^+$.

Example 6c

Preparation of 2-[4-(2-hydroxyethyl)piperazin-1-yl]-1-(6-methyl-2,3-dihydro-1,4-benzoxazin-4-yl)ethanone

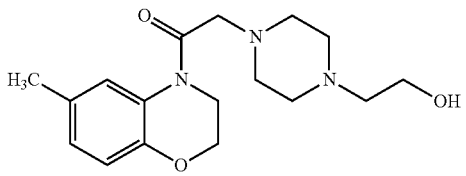 [SMILES: Cc1ccc2c(c1)N(C(=O)CN1CCN(CCO)CC1)CCO2]

Using the procedure described above in step 2, Example 1, but using 2-(piperazin-1-yl)ethan-1-ol in place of N-methylpiperazine, the title compound was prepared. MS. $C_{17}H_{25}N_3O_3$ Exact Mass: 320.2 $(M+H)^+$.

Example 6d

Preparation of 1-(2,3-dihydro-1,4-benzothiazin-4-yl)-2-[4-(2-hydroxyethyl)piperazin-1-yl]ethanone

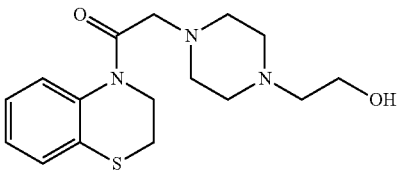 [SMILES: O=C(CN1CCN(CCO)CC1)N1CCSc2ccccc21]

Using the procedure described above in Example 6c, but using 3,4-dihydro-2H-benzo[b][1,4]thiazine in place of 6-methyl-3,4-dihydro-2H-benzo[b][1,4]oxazine, the title compound was prepared. MS. $C_{16}H_{23}N_3O_2S$ Exact Mass: 322.2 $(M+H)^+$.

Example 6e

Preparation of 1-(2,3-dihydro-1,4-benzothiazin-4-yl)-2-(4-propan-2-ylpiperazin-1-yl)ethanone

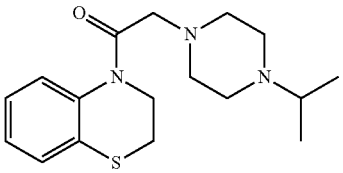 [SMILES: CC(C)N1CCN(CC(=O)N2CCSc3ccccc32)CC1]

Using the procedure described above in Example 6b, but using 3,4-dihydro-2H-benzo[b][1,4]thiazine in place of 6-methyl-3,4-dihydro-2H-benzo[b][1,4]oxazine, the title compound was prepared. MS. $C_{17}H_{25}N_3OS$ Exact Mass: 320.17 $(M+H)^+$.

Example 6f

Preparation of 1-(2,3-dihydropyrido[2,3-b][1,4]ox-azin-1-yl)-2-(4-propan-2-ylpiperazin-1-yl)ethanone

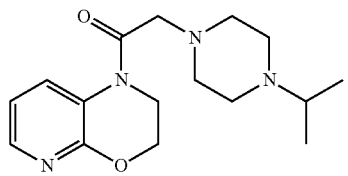 [SMILES: CC(C)N1CCN(CC(=O)N2CCOc3ncccc32)CC1]

Using the procedure described above in Example 6b, but 2,3-dihydro-1H-pyrido[2,3-b][1,4]oxazine (Bioorganic & Medicinal Chemistry Letters (2008), 18(16), 4700-4704) in place of 6-methyl-3,4-dihydro-2H-benzo[b][1,4]oxazine, the title compound was prepared. MS. $C_{16}H_{24}N_4O_2$ Exact Mass: 305.2 (M+H)$^+$.

Example 6g

Preparation of 1-(2,3-dihydropyrido[2,3-b][1,4]ox-azin-1-yl)-2-[4-(2-hydroxyethyl)piperazin-1-yl]etha-none

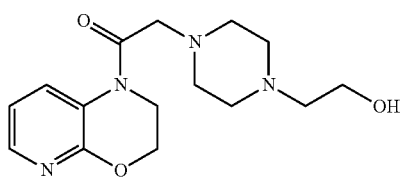 [SMILES: O=C(CN1CCN(CCO)CC1)N1CCOc2ncccc21]

Using the procedure described above in Example 6c, but 2,3-dihydro-1H-pyrido[2,3-b][1,4]oxazine (Bioorganic & Medicinal Chemistry Letters (2008), 18(16), 4700-4704) in place of 6-methyl-3,4-dihydro-2H-benzo[b][1,4]oxazine, the title compound was prepared. MS. $C_{15}H_{22}N_4O_3$ Exact Mass: 307.2 (M+H)$^+$.

Example 6h

Preparation of 1-(2,3-dihydropyrido[3,4-b][1,4]ox-azin-1-yl)-2-(4-propan-2-ylpiperazin-1-yl)ethanone

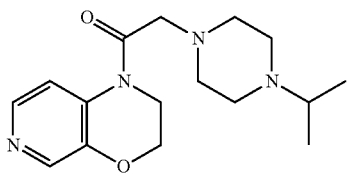 [SMILES: CC(C)N1CCN(CC(=O)N2CCOc3cnccc32)CC1]

Using the procedure described above in Example 6b, but 2,3-dihydro-1H-pyrido[3,4-b][1,4]oxazine (U.S. Pat. No. 5,652,363 A (1997)) in place of 6-methyl-3,4-dihydro-2H-benzo[b][1,4]oxazine, the title compound was prepared. MS. $C_{16}H_{24}N_4O_2$ Exact Mass: 305.2 (M+H)$^+$.

Example 6i

Preparation of 1-(2,3-dihydropyrido[3,4-b][1,4]ox-azin-1-yl)-2-[4-(2-hydroxyethyl)piperazin-1-yl]etha-none

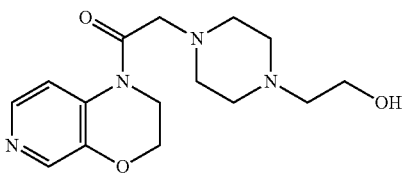 [SMILES: O=C(CN1CCN(CCO)CC1)N1CCOc2cnccc21]

Using the procedure described above in Example 6c, but 2,3-dihydro-1H-pyrido[3,4-b][1,4]oxazine (U.S. Pat. No. 5,652,363 A (1997)) in place of 6-methyl-3,4-dihydro-2H-benzo[b][1,4]oxazine, the title compound was prepared. MS. $C_{15}H_{22}N_4O_3$ Exact Mass: 307.2 (M+H)$^+$.

Example 6j

Preparation of 1-(2,3-dihydropyrido[4,3-b][1,4]ox-azin-4-yl)-2-(4-propan-2-ylpiperazin-1-yl)ethanone

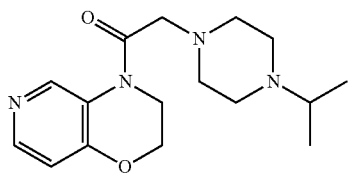 [SMILES: CC(C)N1CCN(CC(=O)N2CCOc3ccncc32)CC1]

Using the procedure described above in Example 6b, but 3,4-dihydro-2H-pyrido[4,3-b][1,4]-oxazine (WO 2009145456 A2) in place of 6-methyl-3,4-dihydro-2H-benzo[b][1,4]oxazine, the title compound was prepared. MS. $C_{16}H_{24}N_4O_2$ Exact Mass: 305.2 (M+H)$^+$.

Example 6k

Preparation of 1-(2,3-dihydropyrido[4,3-b][1,4]ox-azin-4-yl)-2-[4-(2-hydroxyethyl)piperazin-1-yl]etha-none

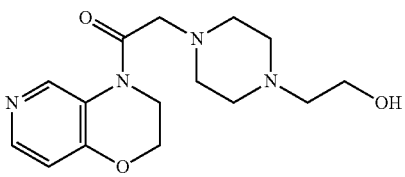 [SMILES: O=C(CN1CCN(CCO)CC1)N1CCOc2ccncc21]

Using the procedure described above in Example 6c, but 3,4-dihydro-2H-pyrido[4,3-b][1,4]-oxazine (WO 2009145456 A2) in place of 6-methyl-3,4-dihydro-2H-benzo[b][1,4]oxazine, the title compound was prepared. MS. $C_{15}H_{22}N_4O_3$ Exact Mass: 307.2 (M+H)$^+$.

Example 61

Preparation of 1-(2,3-dihydropyrido[3,2-b][1,4]ox-azin-4-yl)-2-(4-propan-2-ylpiperazin-1-yl)ethanone

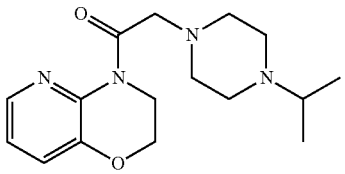 [SMILES: CC(C)N1CCN(CC(=O)N2CCOc3cccnc32)CC1]

Using the procedure described above in Example 6b, but 3,4-dihydro-2H-pyrido[3,2-b][1,4]-oxazine (PCT Int. Appl., 2007139002, 6 Dec. 2007) in place of 6-methyl-3,4-dihydro-2H-benzo[b][1,4]oxazine, the title compound was prepared. MS. $C_{16}H_{24}N_4O_2$ Exact Mass: 305.2 $(M+H)^+$.

Example 6m

Preparation of 1-(2,3-dihydropyrido[3,2-b][1,4]ox-azin-4-yl)-2-[4-(2-hydroxyethyl)piperazin-1-yl]etha-none

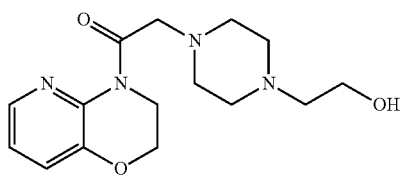 [SMILES: O=C(CN1CCN(CCO)CC1)N1CCOc2cccnc21]

Using the procedure described above in Example 6c, but 3,4-dihydro-2H-pyrido[3,2-b][1,4]-oxazine (PCT Int. Appl., 2007139002, 6 Dec. 2007) in place of 6-methyl-3,4-dihydro-2H-benzo[b][1,4]oxazine, the title compound was prepared. MS. $C_{15}H_{22}N_4O_3$ Exact Mass: 307.2 $(M+H)^+$.

Example 7

Preparation of 6-methyl-4-(2-(4-methylpiperazin-1-yl)ethyl)-2H-benzo[b][1,4]-oxazin-3(4H)-one

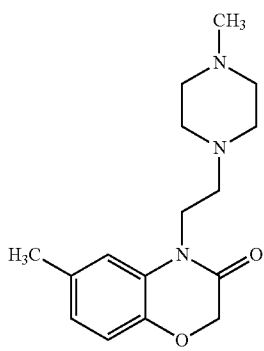

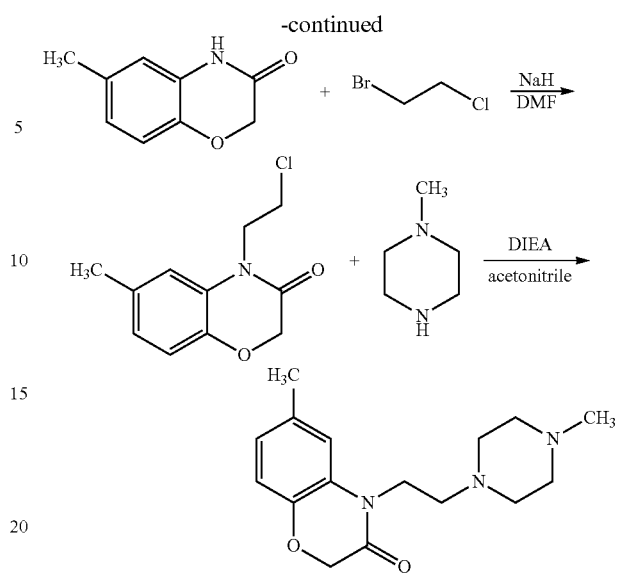

Step 1:

To a solution of 6-methyl-2H-benzo[b][1,4]oxazin-3 (4H)-one (100 mg, 0.6 mmol) in DMF (3 mL) was added NaH (30 mg, 60% suspension in oil, 0.73 mmol) and stirred at room temperature for five minutes. 1-bromo-2-chloroeth-ane (0.332 mL, 3 mmol) was added and the reaction mixture was stirred at room temperature for 3.5 h. Water was added and the reaction mixture was extracted with ethyl acetate. The organic layer was washed with brine, dried with anhydrous $Na_2SO_4$, filtered and concentrated. Flash chromatography yielded 4-(2-chloroethyl)-6-methyl-2H-benzo[b][1,4] oxazin-3 (4H)-one (135 mg, 98%).

Step 2:

A solution of 4-(2-chloroethyl)-6-methyl-2H-benzo[b][1, 4]oxazin-3(4H)-one (30 mg, 0.13 mmol), acetonitrile (0.5 mL), diisopropylethylamine (0.046 mL, 0.26 mmol) and 1-methylpiperazine (0.044 mL, 0.399 mmol) was heated at 80° C. overnight. The reaction mixture was brought to room temperature and then concentrated under reduced pressure. The product was purified by HPLC-MS. $C_{16}H_{23}N_3O_2$ 290.2 $(M+H)^+$.

Example 8

Preparation of 2-(6-methyl-2,3-dihydro-4H-benzo[b][1,4]oxazin-4-yl)-1-(4-methylpiperazin-1-yl)ethan-1-one

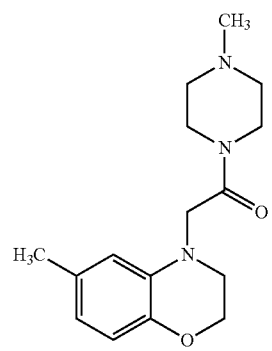

73
-continued

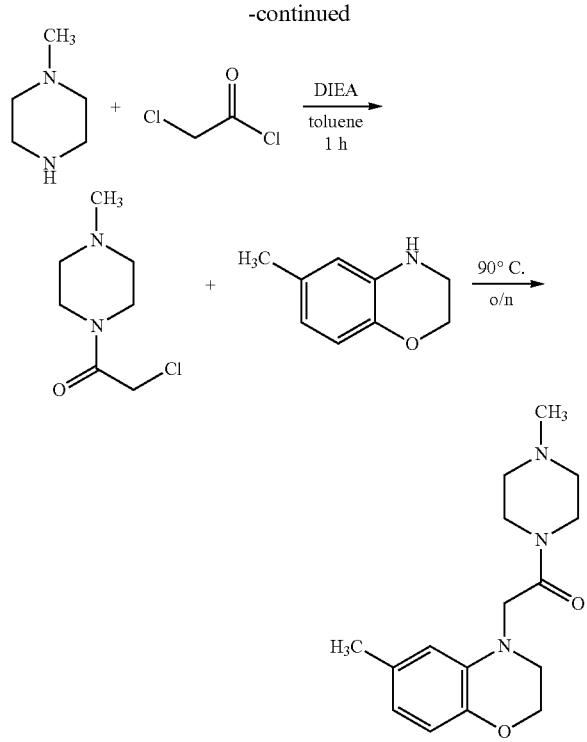

To a solution of 1-methylpiperazine (0.067 mL, 0.6 mmol) and diisopropylethylamine (0.313 mL, 1.8 mmol) in toluene (2 mL) was added chloroacetyl chloride (0.048 mL, 0.6 mmol) and the resulting mixture was stirred at room temperature for 1 h. 6-Methyl-3,4-dihydro-2H-benzo[b][1,4]oxazine (30 mg, 0.21 mmol) was added and the reaction mixture was heated at 90° C. overnight. The reaction mixture was brought to room temperature, water was added and the mixture was extracted with ethyl acetate. The combined organic layers were washed with brine, dried with anhydrous $Na_2SO_4$, filtered and concentrated in vacuo. The product was purified by HPLC-MS. $C_{16}H_{23}N_3O_2$ 290.2 $(M+H)^+$.

Example 8a

Preparation of 1-[4-(2-hydroxyethyl)piperazin-1-yl]-2-(6-methyl-2,3-dihydro-1,4-benzoxazin-4-yl)ethanone

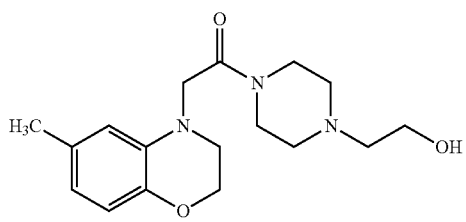 [SMILES: Cc1ccc2c(c1)N(CC(=O)N1CCN(CCO)CC1)CCO2]

Using the procedure described above in Example 8, but using 2-(piperazin-1-yl)ethan-1-ol in place of N-methylpiperazine, the title compound was prepared. MS. $C_{17}H_{25}N_3O_3$ Exact Mass: 320.2 $(M+H)^+$.

Example 8b

Preparation of 1-[4-(2-methoxyethyl)piperazin-1-yl]-2-(6-methyl-2,3-dihydro-1,4-benzoxazin-4-yl)ethanone

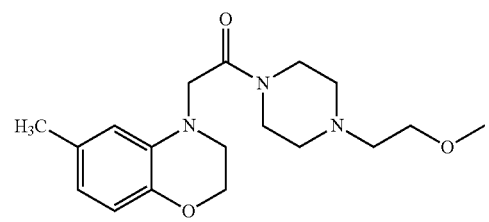

Using the procedure described above in Example 8, but using 1-(2-methoxyethyl)piperazine in place of N-methylpiperazine, the title compound was prepared. MS. $C_{18}H_{27}N_3O_3$ Exact Mass: 334.2 $(M+H)^+$.

Example 8c

Preparation of 1-[4-[2-(dimethylamino)ethyl]piperazin-1-yl]-2-(6-methyl-2,3-dihydro-1,4-benzoxazin-4-yl)ethanone

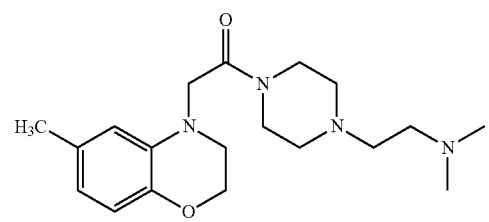

Using the procedure described above in Example 8, but using N,N-dimethyl-2-(piperazin-1-yl)ethan-1-amine in place of N-methylpiperazine, the title compound was prepared. MS. $C_{19}H_{30}N_4O_2$ Exact Mass: 347.2 $(M+H)^+$.

Example 8d

Preparation of 4-[4-[2-(6-methyl-2,3-dihydro-1,4-benzoxazin-4-yl)acetyl]piperazin-1-yl]butanenitrile

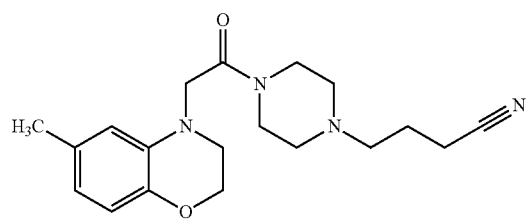 [SMILES: Cc1ccc2c(c1)N(CC(=O)N1CCN(CCCC#N)CC1)CCO2]

Using the procedure described above in Example 8, but using 4-(piperazin-1-yl)butanenitrile in place of N-methylpiperazine, the title compound was prepared. MS. $C_{19}H_{26}N_4O_2$ Exact Mass: 343.2 $(M+H)^+$.

Example 8e

Preparation of N-[2-[4-[2-(6-methyl-2,3-dihydro-1,4-benzoxazin-4-yl)acetyl]piperazin-1-yl]ethyl]acetamide

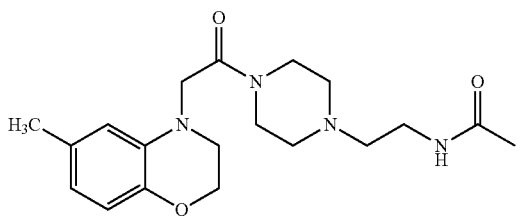 [SMILES: CC(=O)NCCN1CCN(C(=O)CN2CCOc3ccc(C)cc32)CC1]

Using the procedure described above in Example 8, but using N-(2-(piperazin-1-yl)ethyl)-acetamide in place of N-methylpiperazine, the title compound was prepared. MS. $C_{19}H_{28}N_4O_3$ Exact Mass: 361.2 (M+H)$^+$.

Example 8f

Preparation of N-[2-[4-[2-(6-methyl-2,3-dihydro-1,4-benzoxazin-4-yl)acetyl]piperazin-1-yl]ethyl]methanesulfonamide

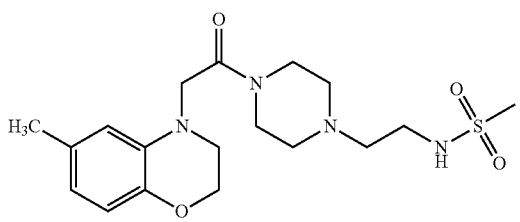

Using the procedure described above in Example 8, but using N-(2-(piperazin-1-yl)ethyl)methanesulfonamide in place of N-methylpiperazine, the title compound was prepared. MS. $C_{18}H_{28}N_4O_4S$ Exact Mass: 397.2 (M+H)$^+$.

Example 8g

Preparation of 2-(6-methyl-2,3-dihydro-1,4-benzoxazin-4-yl)-1-(4-propan-2-ylpiperazin-1-yl)ethanone

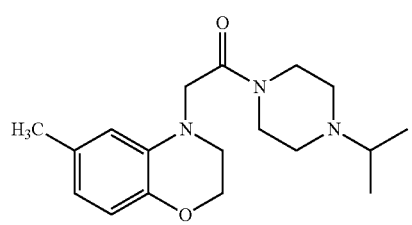 [SMILES: Cc1ccc2c(c1)N(CC(=O)N1CCN(C(C)C)CC1)CCO2]

Using the procedure described above in Example 8, but 1-isopropylpiperazine in place of N-methylpiperazine, the title compound was prepared. MS. $C_{18}H_{27}N_3O_2$ Exact Mass: 318.2 (M+H)$^+$.

Example 8h

Preparation of 2-(2,3-dihydro-1,4-benzothiazin-4-yl)-1-[4-(2-hydroxyethyl)piperazin-1-yl]ethanone

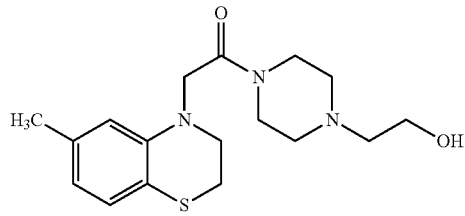

Using the procedure described above in Example 8a, but 3,4-dihydro-2H-benzo[b][1,4]thiazine in place of 6-methyl-3,4-dihydro-2H-benzo[b][1,4]oxazine, the title compound was prepared. MS. $C_{16}H_{23}N_3O_2S$ Exact Mass: 322.2 (M+H)$^+$.

Example 8i

Preparation of 2-(2,3-dihydro-1,4-benzothiazin-4-yl)-1-(4-propan-2-ylpiperazin-1-yl)ethanone

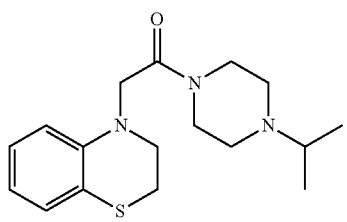 [SMILES: CC(C)N1CCN(C(=O)CN2CCSc3ccccc32)CC1]

Using the procedure described above in Example 8g, but 3,4-dihydro-2H-benzo[b][1,4]thiazine in place of 6-methyl-3,4-dihydro-2H-benzo[b][1,4]oxazine, the title compound was prepared. MS. $C_{17}H_{25}N_3OS$ Exact Mass: 320.2 (M+H)$^+$.

Example 8j

Preparation of 2-(2,3-dihydropyrido[2,3-b][1,4]oxazin-1-yl)-1-[4-(2-hydroxyethyl)piperazin-1-yl]ethanone

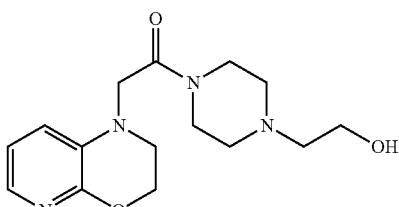

Using the procedure described above in Example 8a, but 2,3-dihydro-1H-pyrido[2,3-b][1,4]oxazine (Bioorganic & Medicinal Chemistry Letters (2008), 18(16), 4700-4704) in place of 6-methyl-3,4-dihydro-2H-benzo[b][1,4]oxazine, the title compound was prepared. MS. $C_{15}H_{22}N_4O_3$ Exact Mass: 307.2 (M+H)$^+$.

Example 8k

Preparation of 2-(2,3-dihydropyrido[2,3-b][1,4]oxazin-1-yl)-1-(4-propan-2-ylpiperazin-1-yl)ethanone

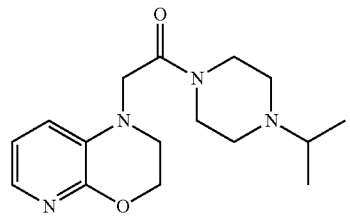 [SMILES: CC(C)N1CCN(C(=O)CN2CCOc3ncccc32)CC1]

Using the procedure described above in Example 8g, but 2,3-dihydro-1H-pyrido[2,3-b][1,4]-oxazine in place of 6-methyl-3,4-dihydro-2H-benzo[b][1,4]oxazine, the title compound was prepared. MS. $C_{16}H_{24}N_4O_2$ Exact Mass: 305.2 $(M+H)^+$.

Example 8l

Preparation of 2-(2,3-dihydropyrido[3,4-b][1,4]oxazin-1-yl)-1-[4-(2-hydroxyethyl)piperazin-1-yl]ethanone

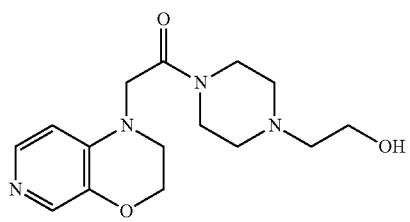 [SMILES: O=C(CN1CCOc2cnccc21)N1CCN(CCO)CC1]

Using the procedure described above in Example 8a, but 2,3-dihydro-1H-pyrido[3,4-b][1,4]oxazine (U.S. Pat. No. 5,652,363 A (1997)) in place of 6-methyl-3,4-dihydro-2H-benzo[b][1,4]oxazine, the title compound was prepared. MS. $C_{15}H_{22}N_4O_3$ Exact Mass: 307.2 $(M+H)^+$.

Example 8m

Preparation of 2-(2,3-dihydropyrido[3,4-b][1,4]oxazin-1-yl)-1-(4-propan-2-ylpiperazin-1-yl)ethanone

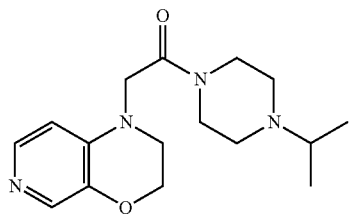

Using the procedure described above in Example 8g, but 2,3-dihydro-1H-pyrido[3,4-b][1,4]oxazine (U.S. Pat. No. 5,652,363 A (1997)) in place of 6-methyl-3,4-dihydro-2H-benzo[b][1,4]oxazine, the title compound was prepared. MS. $C_{16}H_{24}N_4O_2$ Exact Mass: 305.2 $(M+H)^+$.

Example 8n

Preparation of 2-(2,3-dihydropyrido[4,3-b][1,4]oxazin-4-yl)-1-[4-(2-hydroxyethyl)piperazin-1-yl]ethanone

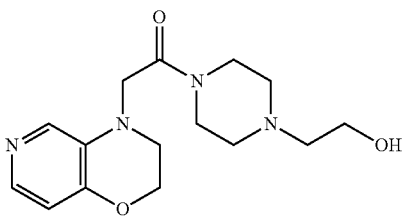 [SMILES: O=C(CN1CCOc2ccncc21)N1CCN(CCO)CC1]

Using the procedure described above in Example 8a, but 3,4-dihydro-2H-pyrido[4,3-b][1,4]oxazine (WO 2009145456 A2) in place of 6-methyl-3,4-dihydro-2H-benzo[b][1,4]-oxazine, the title compound was prepared. MS. $C_{15}H_{22}N_4O_3$ Exact Mass: 307.2 $(M+H)^+$.

Example 8o

Preparation of 2-(2,3-dihydropyrido[4,3-b][1,4]oxazin-4-yl)-1-(4-propan-2-ylpiperazin-1-yl)ethanone

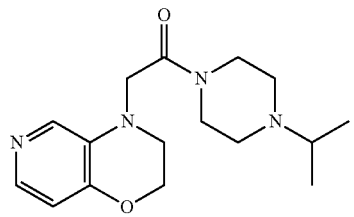

Using the procedure described above in Example 8g, but 3,4-dihydro-2H-pyrido[4,3-b][1,4]oxazine (WO 2009145456 A2) in place of 6-methyl-3,4-dihydro-2H-benzo[b][1,4]-oxazine, the title compound was prepared. MS. $C_{16}H_{24}N_4O_2$ Exact Mass: 305.2 $(M+H)^+$.

Example 8p

Preparation of 2-(2,3-dihydro-4H-pyrido[3,2-b][1,4]oxazin-4-yl)-1-(4-(2-hydroxyethyl)-piperazin-1-yl)ethan-1-one

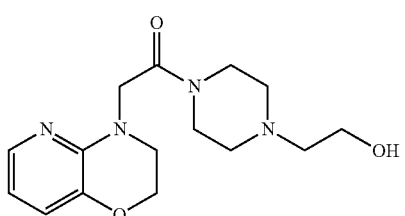

Using the procedure described above in Example 8a, but 3,4-dihydro-2H-pyrido[3,2-b][1,4]-oxazine (PCT Int. Appl., 2007139002, 6 Dec. 2007) in place of 6-methyl-3,4-dihydro-2H-benzo[b][1,4]oxazine, the title compound was prepared. MS. $C_{15}H_{22}N_4O_3$ Exact Mass: 307.2 $(M+H)^+$.

Example 8q

Preparation of 2-(2,3-dihydropyrido[3,2-b][1,4]oxazin-4-yl)-1-(4-propan-2-ylpiperazin-1-yl)ethanone

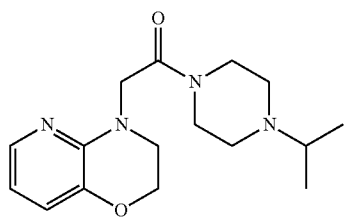 [SMILES: CC(C)N1CCN(C(=O)CN2CCOc3cccnc32)CC1]

Using the procedure described above in Example 8g, but 3,4-dihydro-2H-pyrido[3,2-b][1,4]-oxazine (PCT Int. Appl., 2007139002, 6 Dec. 2007) in place of 6-methyl-3,4-dihydro-2H-benzo[b][1,4]oxazine, the title compound was prepared. MS. $C_{16}H_{24}N_4O_2$ Exact Mass: 305.2 $(M+H)^+$.

Example 9

Preparation of 6-methyl-4-(2-(4-methylpiperazin-1-yl)-2-oxoethyl)-2H-benzo[b]-[1,4]oxazin-3(4H)-one

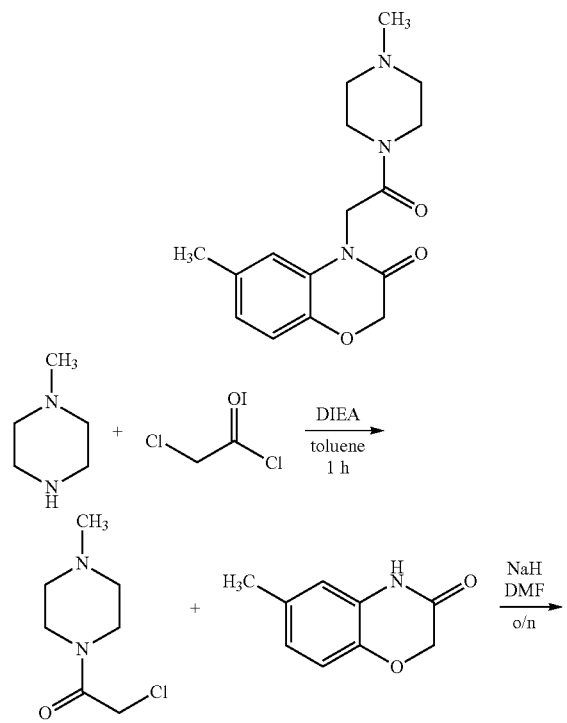

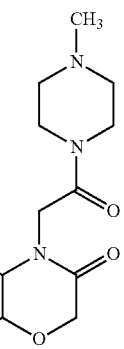

To a solution of 1-methylpiperazine (0.148 mL, 1.34 mmol) and diisopropylethylamine (0.35 mL, 2 mmol) in toluene (2 mL) was added chloroacetyl chloride (0.106 mL, 1.34 mmol) and the resulting mixture was stirred at r.t. for 1 h. This solution was then transferred to a solution containing 6-methyl-2H-benzo[b][1,4]oxazin-3(4H)-one (100 mg, 0.64 mmol) and NaH (77 mg, 60% suspension in oil, 1.92 mmol) in DMF (2 mL) and stirred overnight at room temperature. The reaction mixture was quenched with water and extracted with ethyl acetate. The combined organic layers were washed with brine, dried with anhydrous $Na_2SO_4$, filtered and concentrated in vacuo. The product was purified by HPLC-MS. $C_{16}H_{21}N_3O_3$ 304.2 $(M+H)^+$.

Example 10

Preparation of 6-methyl-4-(2-(4-methylpiperazin-1-yl)ethyl)-3,4-dihydro-2H-benzo[b][1,4]oxazine

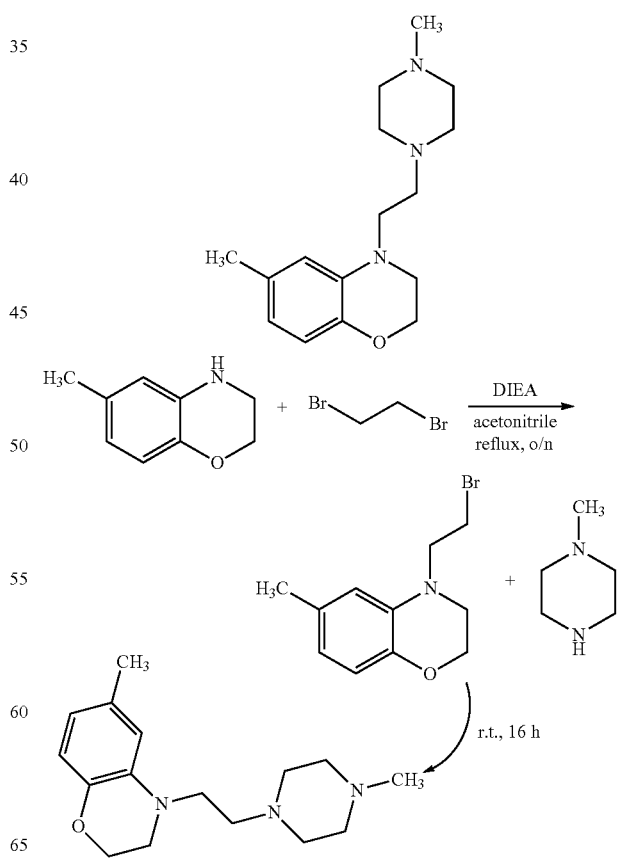

A solution of 6-methyl-3,4-dihydro-2H-benzo[b][1,4]oxazine (50 mg, 0.33 mmol), acetonitrile (5 mL), diisopropylethylamine (0.29 mL, 1.67 mmol), 1,2-dibromoethane (0.113 mL, 1.3 mmol) was heated at 80° C. overnight. The reaction mixture was brought to room temperature and 1-methylpiperazine (0.4 mL, 3.6 mmol) was added. The reaction mixture was stirred for 16 h at room temperature and then concentrated under reduced pressure. The product was purified by HPLC-MS. $C_{16}H_{25}N_3O$ 276.20 $(M+H)^+$.

Example 11

Preparation of 6-methyl-4-(3-(4-methylpiperazin-1-yl)propyl)-2H-benzo[b][1,4]-oxazin-3(4H)-one

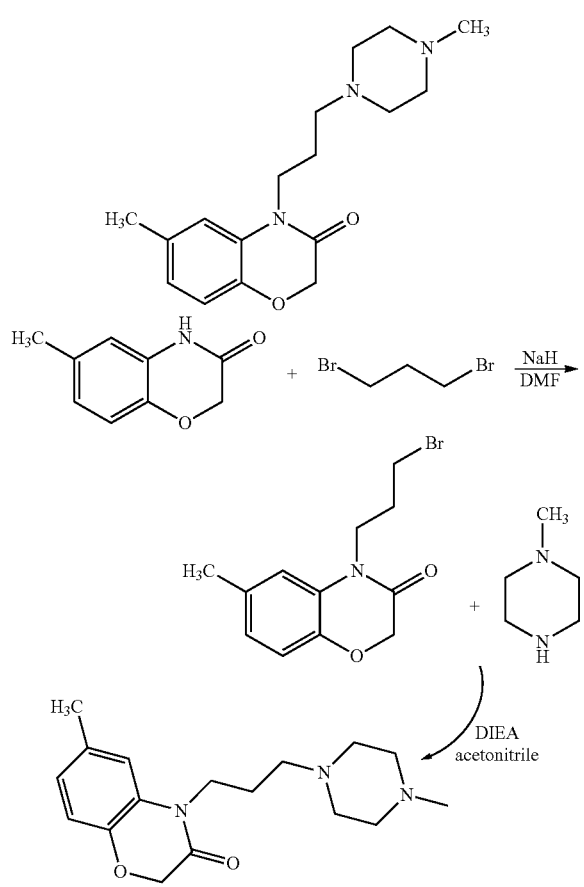

Step 1:
To a solution of 6-methyl-2H-benzo[b][1,4]oxazin-3(4H)-one (100 mg, 0.6 mmol) in DMF (3 mL) was added NaH (28 mg, 60% suspension in oil, 0.73 mmol) and stirred at room temperature for five minutes. 1,3-dibromopropane (0.3 mL, 3 mmol) was added and the reaction mixture was stirred at room temperature for 3 h. Water was added and the reaction mixture was extracted with ethyl acetate. The organic layer was washed with brine, dried with anhydrous $Na_2SO_4$, filtered and concentrated. Flash chromatography yielded 4-(3-bromopropyl)-6-methyl-2H-benzo[b][1,4]oxazin-3(4H)-one (125 mg, 72%).

Step 2:
A solution of 4-(3-bromopropyl)-6-methyl-2H-benzo[b][1,4]oxazin-3(4H)-one (85 mg, 0.3 mmol), acetonitrile (4 mL), diisopropylethylamine (1.149 mL, 6.6 mmol) and 1-methylpiperazine (0.732 mL, 6.6 mmol) was heated at 80° C. for 3 h. The reaction mixture was brought to room temperature and then concentrated under reduced pressure. Product was purified by HPLC-MS. $C_{17}H_{25}N_3O_2$ 304.2 $(M+H)^+$.

Example 12

Preparation of 3-(6-methyl-2,3-dihydro-4H-benzo[b][1,4]oxazin-4-yl)-1-(4-methylpiperazin-1-yl)propan-1-one

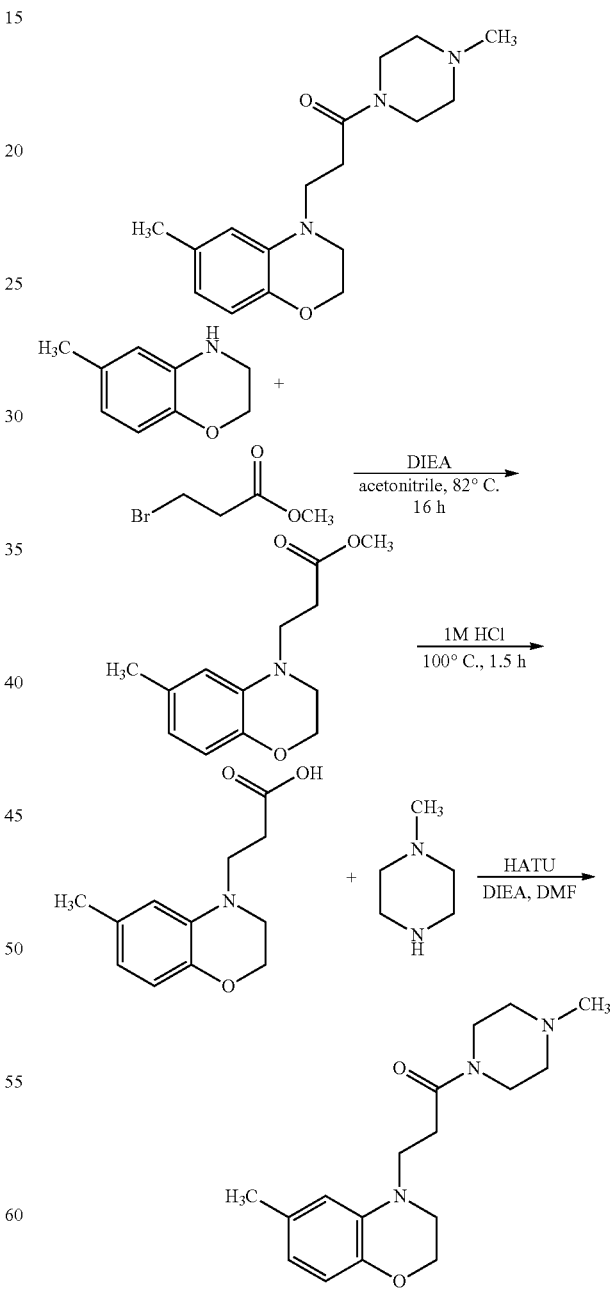

Step 1:
A solution of 6-methyl-3,4-dihydro-2H-benzo[b][1,4]oxazine (200 mg, 1.3 mmol), diisopropylethylamine (0.325 mL, 1.86 mmol) and methyl-3-bromo-propionate (0.3 mL, 2.74 mmol) in acetonitrile (2 mL) was heated at 82° C. for 16 h. Reaction mixture was brought to room temperature, water was added and extracted with ethyl acetate. Combined organic layers were washed with brine, dried with anhydrous Na$_2$SO$_4$, filtered and concentrated in vacuo to give crude methyl 3-(6-methyl-2H-benzo[b][1,4]oxazin-4(3H)-yl)propanoate which was used in next without purification.

Step 2:

1M HCl (3 mL) was added to methyl 3-(6-methyl-2H-benzo[b][1,4]oxazin-4(3H)-yl)propanoate (88 mg) and the mixture was heated at 100° C. for 1.5 h. Reaction mixture was then brought to room temperature, diluted with water and extracted with ethyl acetate. The organic layer was washed with brine, dried with anhydrous Na$_2$SO$_4$ filtered and concentrated to give corresponding acid (50 mg).

Step 3:

To a solution of the acid (50 mg) in DMF (1 mL) was added 1-methylpiperazine (0.038 mL, 0.339 mmol), 1-[bis(dimethylamino)methylene]-1H-1,2,3-triazolo[4,5-b]pyridinium 3-oxide hexafluorophosphate (HATU) (172 mg, 0.452 mmol) and diisopropylethylamine (0.2 mL, 1.13 mmol). The resulting mixture was stirred at room temperature for 1.5 h. Reaction mixture was then purified by HPLC to obtain product title product. MS. C$_{17}$H$_{25}$N$_3$O$_2$ 304.2 (M+H)$^+$.

Example 13

Preparation of 6-methyl-4-(3-(4-methylpiperazin-1-yl)-3-oxopropyl)-2H-benzo[b][1,4]oxazin-3(4H)-one

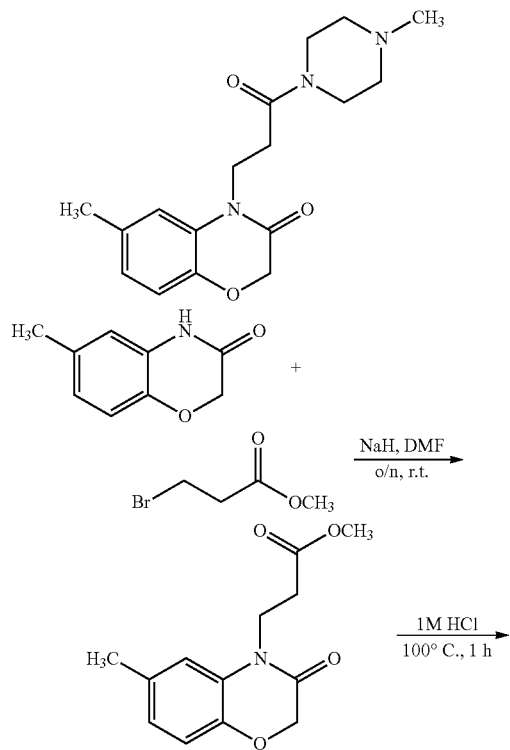

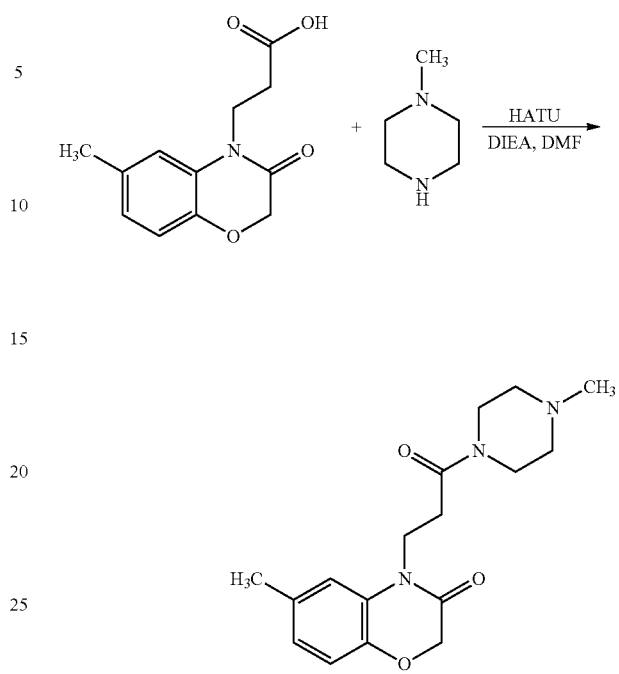

Step 1:

To a solution of 6-methyl-2H-benzo[b][1,4]oxazin-3(4H)-one (100 mg, 0.64 mmol), in DMF (2 mL) was added NaH (77 mg, 60% suspension in oil, 1.92 mmol) and the resulting mixture was stirred for 10 min at room temperature. Methyl-3-bromo-propionate (0.139 mL, 1.28 mmol) was added and stirred overnight. Reaction mixture was quenched with water and extracted with ethyl acetate. The combined organic layers were washed with brine, dried with anhydrous Na$_2$SO$_4$, filtered and concentrated in vacuo to give crude methyl 3-(6-methyl-3-oxo-2H-benzo[b][1,4]oxazin-4(3H)-yl)propanoate, which was used in the next step without purification.

Step 2:

Crude methyl 3-(6-methyl-3-oxo-2H-benzo[b][1,4]oxazin-4(3H)-yl)propanoate was added to 1N HCl (4 mL) and heated at 100° C. for 1 h. Product precipitated out upon cooling the reaction mixture to r.t. Precipitates were filtered, washed with ice/H2O and dried under vacuum to give 3-(6-methyl-3-oxo-2H-benzo[b][1,4]oxazin-4(3H)-yl)propanoic acid (109 mg, 76% over 2 steps).

Step 3:

To a solution of 3-(6-methyl-3-oxo-2H-benzo[b][1,4]oxazin-4(3H)-yl)propanoic acid (60 mg, 0.25 mmol) in DMF (2 mL) was added 1-methylpiperazine (0.043 mL, 0.382 mmol), HATU (194 mg, 0.51 mmol) and diisopropylethylamine (0.22 mL, 1.27 mmol). The resulting mixture was stirred at room temperature overnight. The reaction mixture was then purified by HPLC to obtain the title product. MS. C$_{17}$H$_{23}$N$_3$O$_3$ 318.2 (M+H)$^+$.

Example 14

Preparation of 6-methyl-4-(3-(4-methylpiperazin-1-yl)propyl)-3,4-dihydro-2H-benzo[b][1,4]oxazine

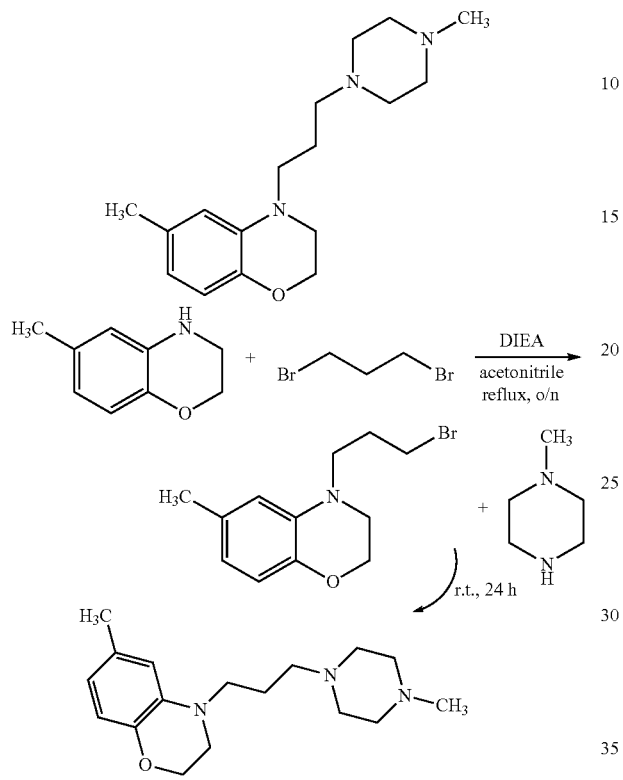

A solution of 6-methyl-3,4-dihydro-2H-benzo[b][1,4]oxazine (50 mg, 0.33 mmol), acetonitrile (3 mL), diisopropylethylamine (0.29 mL, 1.67 mmol), 1,3-dibromopropane (0.134 mL, 1.3 mmol) was heated at 80° C. overnight. Reaction mixture was brought to room temperature and 1-methylpiperazine (0.4 mL, 3.6 mmol) was added. The reaction mixture was stirred for 24 h at room temperature and then concentrated under reduced pressure. The product was purified by HPLC-MS. $C_{17}H_{27}N_3O$ 290.2 $(M+H)^+$.

Example 15

Preparation 1-(6-methyl-2,3-dihydro-4H-benzo[b][1,4]oxazin-4-yl)-3-(4-methylpiperazin-1-yl)propan-1-one

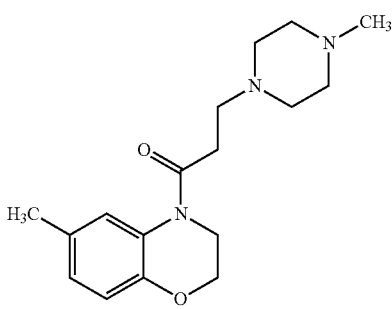

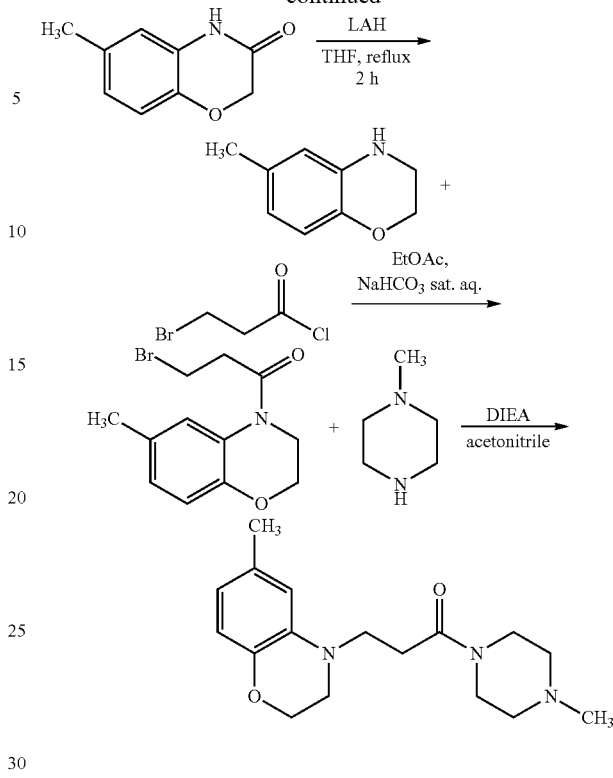

Step 1:

To a solution of 6-methyl-2H-benzo[b][1,4]oxazin-3(4H)-one (2.5 g, 15.3 mmol) in THF (75 mL) was added LAH (1.16 g, 30.6 mmol) in small portions under nitrogen. Reaction mixture was gradually warmed up and refluxed for 2 h. It was then brought to room temperature and then quenched by addition of 15% NaOH (aq.) solution. 5 mL water added and the reaction mixture was filtered to remove solids and rinsed with ethyl acetate 10 mL. Filtrate was diluted with water and extracted with ethyl acetate. Combined organic layers were washed with brine, dried with anhydrous MgSO$_4$, filtered and concentrated. Product was purified by flash chromatography to give 2.13 g (93%) of 6-methyl-3,4-dihydro-2H-benzo[b][1,4]oxazine.

Step 2:

To a solution of 6-methyl-3,4-dihydro-2H-benzo[b][1,4]oxazine (100 mg, 0.67 mmol) in ethyl acetate (2 mL) and saturated aqueous NaHCO$_3$ (1.5 mL) was added 3-bromopropionyl chloride (0.2 mL, 2 mmol) drop wise. After 30 minutes the organic layer was separated and the aq. layer was extracted back with ethyl acetate. Combined organic layers were washed with brine, dried with anhydrous Na$_2$SO$_4$, filtered and concentrated to give crude product 3-bromo-1-(6-methyl-2,3-dihydro-4H-benzo[b][1,4]oxazin-4-yl)propan-1-one (180 mg).

Step 3:

To a solution of crude 3-bromo-1-(6-methyl-2,3-dihydro-4H-benzo[b][1,4]oxazin-4-yl)propan-1-one (100 mg, 0.35 mmol) in acetonitrile (1 mL) was added diisopropylethylamine (0.091 mL, 0.52 mmol) and 1-methylpiperazine (0.039 mL, 0.35 mmol). Resulting mixture was stirred for 2 h at room temperature then concentrated in vacuo. The title product was purified by HPLC. MS. $C_{17}H_{25}N_3O_2$ 304.2 $(M+H)^+$.

Example 16

Preparation of 1-(6-methyl-2,3-dihydro-4H-benzo[b][1,4]oxazin-4-yl)-2-(1-methylpiperidin-4-yl)ethan-1-one

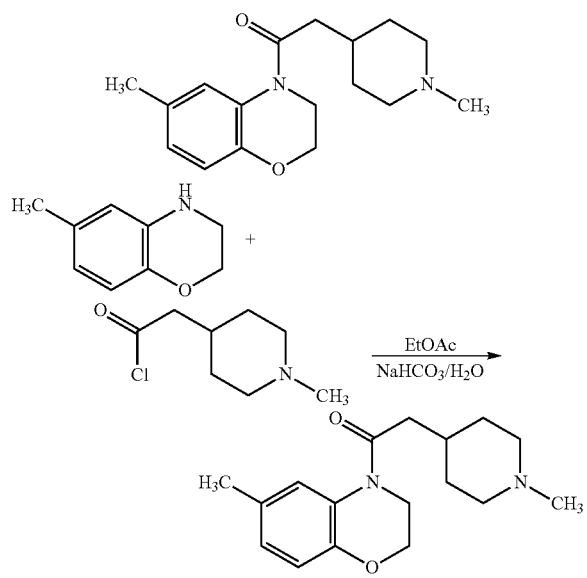

To a solution of 6-methyl-3,4-dihydro-2H-benzo[b][1,4]oxazine (100 mg, 0.67 mmol) in ethyl acetate (2 mL) and saturated aqueous NaHCO$_3$ (1.5 mL) was added 2-(1-methylpiperidin-4-yl)acetyl chloride (175 mg, 1 mmol) (Ger. Offen. (1983), DE 3204153 A1) and the mixture was stirred for 2 h. The organic layer was separated and the aq. layer was extracted back with ethyl acetate. Combined organic layers were washed with brine, dried with anhydrous Na$_2$SO$_4$, filtered and concentrated to give the title compound which was purified by HPLC-MS. C$_{17}$H$_{24}$N$_2$O$_2$ 289.2 (M+H)$^+$.

Example 17

Preparation of 2-(1H-indol-1-yl)-1-(4-isopropylpiperazin-1-yl)ethan-1-one

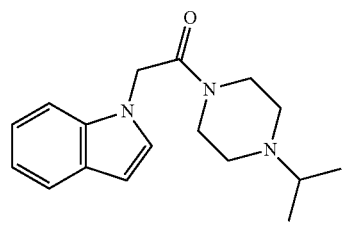 [SMILES: CC(C)N1CCN(C(=O)Cn2ccc3ccccc32)CC1]

Step 1: Preparation of ethyl 2-(1H-indol-1-yl)acetate

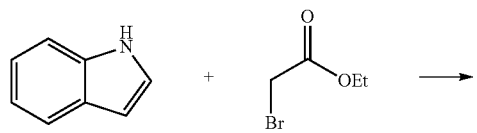

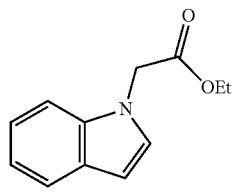

Indole (0.468 g, 4 mmol) was dissolved in anhydrous DMF (16 mL) and cesium carbonate (2.6 g, 8 mmol) was added followed by ethyl bromoacetate (1.33 mL, 12 mmol) and potassium iodide (0.066 g, 0.4 mmol). The mixture was heated to 160 degrees for 20 minutes and then cooled. Partition of the reaction mixture between water and ethyl acetate, followed by washing with dilute sulfuric acid, water and brine afforded a crude product (1.07 g) after drying and evaporation of the solvent which was purified by flash chromatography to afford the pure ethyl 2-(1H-indol-1-yl)acetate (LC/MS=204.1 [M+H]$^+$).

Step 2: Preparation of 2-(1H-indol-1-yl)acetic acid

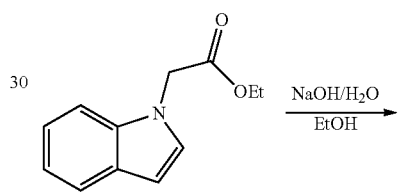

Ethyl 2-(1H-indol-1-yl)acetate (2.03 g, 10 mmol) was dissolved in ethanol (40 mL) and treated with aqueous sodium hydroxide (1N, 50 mL) and stirred at room temperature for 1.5 h. The reaction was rendered slightly acidic with dilute HCl and the mixture concentrated under reduced pressure. Extraction of the residue with ethyl acetate, followed by washing with brine afforded after removal of the solvent, pure 2-(1H-indol-1-yl)acetic acid (1.6 g, 87%), (LC/MS=176.3 [M+H]$^+$).

Step 3: Preparation of 2-(1H-indol-1-yl)-1-(4-isopropylpiperazin-1-yl)ethan-1-one -continued

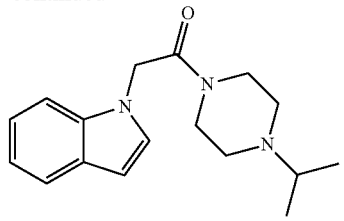

A mixture of 2-(1H-indol-1-yl)acetic acid (0.200 g, 1.14 mmol), EDC (0.450 g, 2.39 mmol), and N-hydroxysuccinimide (0.288 g, 2.51 mmol) was stirred in anhydrous DMF (2 mL) while 1-isopropylpiperazine (0.306, 2.39 mmol) in DMF (1 mL) was added. The mixture was stirred overnight at room temperature. The mixture was partitioned between ethyl acetate and water and the organic layer washed with water followed by brine. Removal of the solvent afforded the crude product which was purified by flash chromatography to afford the title product, 2-(1H-indol-1-yl)-1-(4-isopropylpiperazin-1-yl)ethan-1-one (LC/MS=286.4 [M+H]⁺).

Example 17a

Preparation of 1-(4-(2-hydroxyethyl)piperazin-1-yl)-2-(1H-indol-1-yl)ethan-1-one

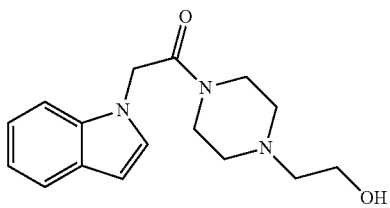 [SMILES: O=C(Cn1ccc2ccccc21)N1CCN(CCO)CC1]

Using a similar procedure as described above in example 17, except for using 2-(piperazin-1-yl)ethan-1-ol in place of 1-isopropylpiperazine afforded 1-(4-(2-hydroxyethyl)piperazin-1-yl)-2-(1H-indol-1-yl)ethan-1-one (LC/MS=288.1 [M+H]⁺).

Example 18

Preparation of 1-(1H-indol-1-yl)-2-(4-isopropylpiperazin-1-yl)ethan-1-one

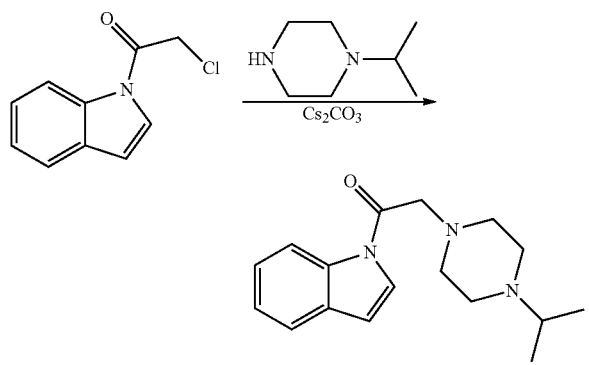

A solution of 2-chloro-1-(1H-indol-1-yl)ethan-1-one (J. Heterocyclic Chem. (2007), 44(5), 1213) (0.193 g, 1 mmol) in anhydrous DMF (2 mL) was treated with cesium carbonate (0.652 g, 2 mmol) and 1-isopropylpiperazine (0.256 g, 2 mmol). The mixture was stirred at 50 degrees for 45 m and then the cooled reaction mixture was partitioned between ethyl acetate and water, washed with brine and then evaporated to dryness. The residue was purified by flash chromatography to afford the pure 1-(1H-indol-1-yl)-2-(4-isopropylpiperazin-1-yl)ethan-1-one (LC/MS=286.2 [M+H]⁺).

Example 18a

Preparation of 2-(4-(2-hydroxyethyl)piperazin-1-yl)-1-(1H-indol-1-yl)ethan-1-one

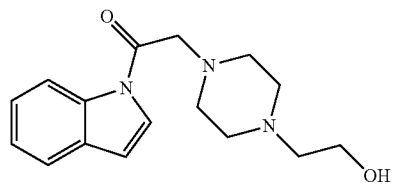 [SMILES: O=C(CN1CCN(CCO)CC1)n1ccc2ccccc21]

Using the previous procedure, substituting 2-(piperazin-1-yl)ethan-1-ol for 1-isopropylpiperazine afforded 2-(4-(2-hydroxyethyl)piperazin-1-yl)-1-(1H-indol-1-yl)ethan-1-one after flash chromatography (LC/MS=288.2 [M+H]⁺).

Example 19

Preparation of 1-(3-(2-chloro-5-oxido-10H-phenothiazin-10-yl)propyl)-4-methylpiperazine 1,4-dioxide

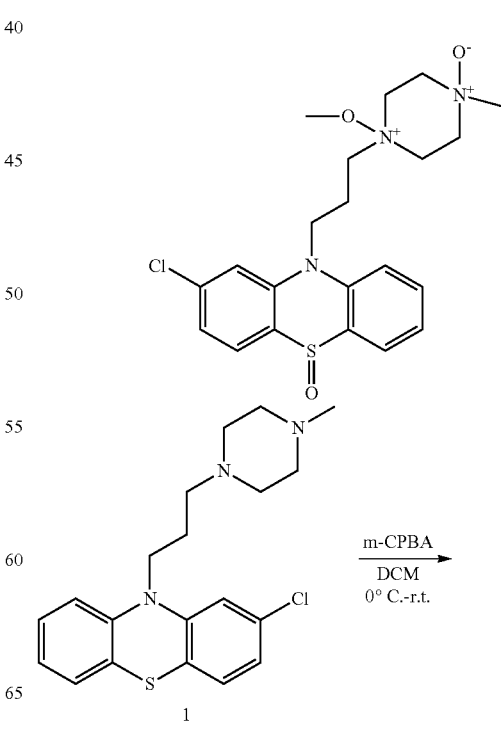

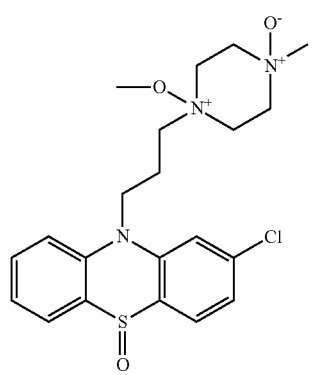

To a suspension of prochlorperazine dimaleate salt 1 (40 mg, 0.066 mmol) in DCM (2 mL) was added m-CPBA (22 mg, 0.13 mmol) at 0° C. Reaction mixture was brought to room temperature after 30 minutes and stirred for further 6 h then concentrated to dryness and triturated with diethyl ether three times. The solid residue was purified by HPLC to obtain the title product. MS. $C_{20}H_{24}ClN_3O_3S$ 422.1 (M+H)+

Example 20

Preparation of 2-chloro-10-(3-(4-methylpiperazin-1-yl)propyl)-10H-phenothiazine 5,5-dioxide

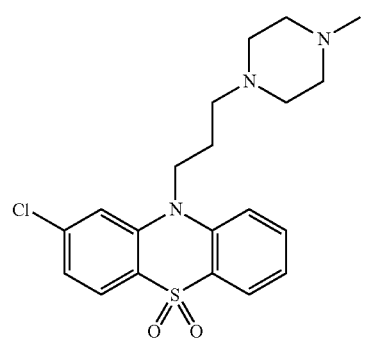

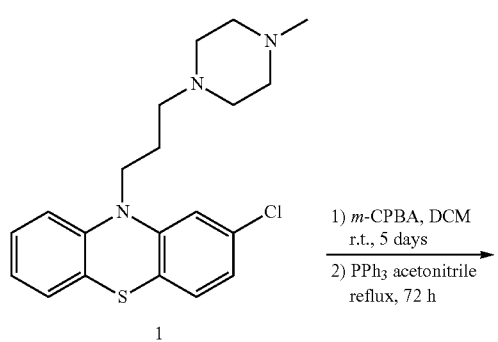

1) m-CPBA, DCM r.t., 5 days
2) PPh3 acetonitrile reflux, 72 h

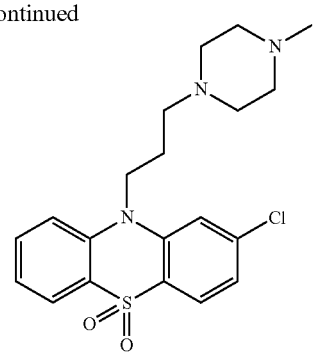

1 (100 mg, 0.165 mmol) in 4 mL DCM was added 10 equiv. m-CPBA (276 mg, 1.6 mmol) and stirred for 5 days at room temperature Reaction mix was concentrated to dryness and triturated with diethyl ether three times. Resulting residue gave a mixture of products corresponding to the addition of three and four oxygen atoms. A portion of this crude mixture (86 mg) was dissolved in acetonitrile (4 mL), added triphenylphosphine (257 mg, 0.98 mmol) and refluxed for 72 h. Reaction mixture was concentrated and the product was purified by thick layer chromatography. Ms. $C_{20}H_{24}ClN_3O_2S$ 406.1 (M+H)+

Example 21

Neuron Autophagy Assay

The compounds in accordance with the present invention have high activities as inducers of neuronal autophagy.

The induction of neuronal autophagy herein was measured by the conversion of photoconvertible reporter in a flux LC3 assay, as described in Tsvetkov et al., Nature Chemical Biology, 9:586-592 (2013), which is incorporated herein by reference.

mApple, kindly provided by Kurt Thorn of the Nikon microscopy core at UCSFR, was cloned into the pGW1 vector. pGW1-GFP and pGW1-Htt[ex1]-Q97-GFP were transfected according to normal protocols.

Cell cultures included striata, cortices, and hippocampi from rat embryos or newborn (postnatal day 0) mice were dissected, dissociated, and plated on 96-well tissue culture plates coated with poly-D-lysine and laminin. Cells were cultured for 4 days in neurobasal medium with L-glutamine and B-27 before use.

Rat neurons were transfected with plasmids using lipofectamine, treated overnight with vehicle (DMSO) or 5, 10, 50, 200, 500, and 1000 nM of exemplifying compounds and imaged everyday, once a day, for 7 days. Compounds A, B, C, D, E, F, G and I in Table 1 were active at less than 50 nM, and Compound M showed a P value of $1.06*10^{-2}$ at 200 nM as compared with DMSO control. Kolmogrov-Smirnov statistics test was used to calculate P values. See Table 2.

TABLE 2

| Compound | Dose | P Value |
| --- | --- | --- |
| D | 5 nM | 1.07E−13 |
| A | 5 nM | 2.63E−11 |
| G | 5 nM | 8.41E−09 |
| C | 5 nM | 1.98E−08 |
| B | 5 nM | 1.91E−06 |
| I | 5 nM | 1.97E−06 |
| F | 10 nM | 3.86E−12 |

TABLE 2-continued

| Compound | Dose | P Value |
|---|---|---|
| E | 10 nM | 1.28E-09 |
| M | 200 nM | 1.06E-02 |

Example 22

Neuronal Death Assay

The compounds were tested in a primary rodent neuron cellular model of HD. In this disease model, neurons from the striatum, the site of severe pathology in HD, are transfected with full-length or N-terminal fragments of wild-type Htt or mHtt. The model recapitulates cellular and molecular features seen in HD, including mHtt-dependent neurodegeneration. To use the model in drug discovery, striatal neurons are co-transfected with fluorescently tagged mHtt and marker proteins and examined longitudinally using an automated fluorescent microscopy system (U.S. Pat. No. 7,139,415, incorporated by reference in its entirety). Neurons that express mHtt are periodically imaged, and the loss of fluorescence of the marker protein corresponds to cell death. Importantly, the automated system monitors how mHtt affects neuronal survival by following single cells longitudinally, distinguishing transfected neurons from non-transfected cells. Neurodegeneration is quantified by the difference in survival time between neuronal cells expressing mHtt and neuronal cells expressing wild-type Htt; drugs that increase neuronal survival in neurons expressing mHtt are neuroprotective. Hazard functions are determined by Cox proportional hazards (CPH) analysis to create hazard ratios that are the estimated instantaneous risk of death of individual cells, independent of population size.

Exemplifying compounds were tested for protecting neurons from mHtt toxicity. For this survival assay, primary neurons were transfected with a construct expressing exon 1 of mHtt protein containing 97 poly-glutamines and a fluorescent reporter to track the neurons. Neurons were imaged for 7 days using automated fluorescent robotic microscopy and analyzed for survival. Fluphenazine (Compound N) at 100 nM was used as positive control. DMSO was used as negative control. Compounds D, E, L, K, O, P, Q, R and S were shown to be active at nM concentrations. See Tables 3-5.

TABLE 3

| Compound | Dose | Hazard Ratio | P Value |
|---|---|---|---|
| D | 10 nM | 0.91611 | 0.034002 |
| E | 50 nM | 0.895216 | 0.00691 |
| L | 200 nM | 0.914285 | 0.0273 |
| K | 200 nM | 0.920887 | 0.044 |
| N | 100 nM | 0.85532 | 0.000174 |
| EGFP/DMSO | — | 0.47801 | <2E-16 |

TABLE 4

| Compound | Dose | Hazard Ratio | P Value |
|---|---|---|---|
| Q | 50 nM | 0.5709 | 0.00296 |
| O | 50 nM | 0.5747 | 0.00374 |
| S | 50 nM | 0.6953 | 0.04409 |
| R | 50 nM | 0.7345 | 0.08295 |
| P | 50 nM | 0.7384 | 0.09139 |

TABLE 4-continued

| Compound | Dose | Hazard Ratio | P Value |
|---|---|---|---|
| N | 100 nM | 0.7018 | 0.04985 |
| EGFP/DMSO | — | 0.3269 | 7.99E-08 |

TABLE 5

| Compound | Dose | Hazard Ratio | P Value |
|---|---|---|---|
| Q | 10 nM | 0.55803 | 0.00436 |
| P | 10 nM | 0.62754 | 0.02199 |
| R | 10 nM | 0.70357 | 0.06936 |
| N | 100 nM | 0.52726 | 0.00385 |
| EGFP/DMSO | — | 0.35366 | 6.20E-07 |

Compound K was also tested for protecting i-neurons from mHtt toxicity. These iPSCs were derived from a Huntington's disease patient carrying 60 CAG repeats. Induced PSC-neurons were treated with either DMSO or K at 50 nM. Neurons were imaged at day 4 to day 9. Compound K reduced the hazard ratio as compared to neurons treated with DMSO (p<0.5). See Table 6.

TABLE 6

| Compound | Dose | Hazard Ratio | P Value |
|---|---|---|---|
| K | 50 nM | 0.7683 | 0.0378 |
| DMSO | — | 1 | — |

From the foregoing it will be appreciated that, although specific embodiments of the invention have been described herein for purposes of illustration, various modifications may be made without deviating from the spirit and scope of the invention.

What is claimed is:

1. A compound of formula V or VI:

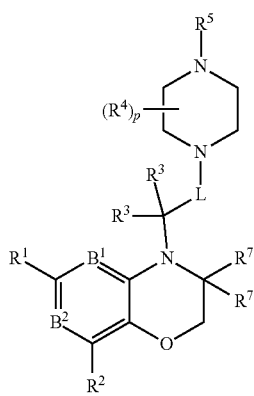

V

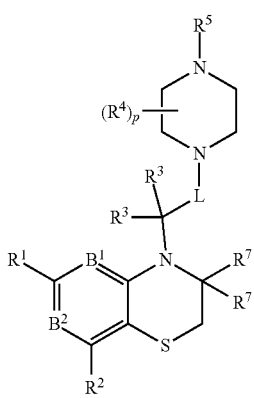

wherein:

$B^1$ and $B^2$ are $CR^2$;

L is selected from the group consisting of a covalent bond, $CR^6_2$, $C(O)$—$(CR^6_2)_m$, $C(S)$—$(CR^6_2)_m$, $O$—$(CR^6_2)_m$, $S$—$(CR^6_2)_m$, $SO$—$(CR^6_2)_m$, $SO_2$—$(CR^6_2)_m$, and $NR^6$—$(CR^6_2)_m$;

the variables m and p independently are 0, 1, 2, 3, 4, 5, 6, or 7;

$R^1$ is $C_1$ to $C_6$ alkyl, $C_1$ to $C_6$ haloalkyl, $C_1$ to $C_6$ alkoxy, $C_1$ to $C_6$ haloalkoxy, cyano, or nitro;

$R^2$ is hydrogen, $C_1$ to $C_6$ alkyl, $C_1$ to $C_6$ haloalkyl, $C_1$ to $C_6$ alkoxy, $C_1$ to $C_6$ haloalkoxy, halo, cyano, or nitro;

$R^3$ are independently hydrogen or $C_1$ to $C_6$ alkyl; or two $R^3$ together with the carbon attached thereto form C=O;

$R^4$ are independently $C_1$ to $C_6$ alkyl; or two $R^4$ together with the carbon attached thereto form C=O;

$R^5$ is hydrogen, $C_1$ to $C_6$ alkyl, substituted $C_1$ to $C_6$ alkyl, cycloalkyl, aryl, or acyl;

each $R^6$ independently is selected from the group consisting of hydrogen, halogen, alkyl, substituted alkyl, cycloalkyl, substituted cycloalkyl, alkenyl, substituted alkenyl, alkoxy, substituted alkoxy, alkynyl, substituted alkynyl, amino, substituted amino, aminosulfinyl substituted aminosulfinyl, aminosulfonyl, substituted aminosulfonyl, sulfinyl, sulfonyl, sulfonyloxy, substituted sulfonyloxy, aminosulfonyloxy, aminosulfinyloxy, aminosulfonylamino, acylamino, aminocarbonyloxy, aminocarbonylamino, aminothiocarbonylamino, amidino, substituted amidino, aminocarbonylamino, aminothiocarbonylamino, acyloxy, aryl, substituted aryl, heteroaryl, substituted heteroaryl, cyano, nitro, carboxyl, carboxyl ester, (carboxyl ester)amino, (carboxyl ester)oxy, hydroxyl, acyl, formyl, aminocarbonyl, substituted aminocarbonyl, and substituted aminothiocarbonyl, or two $R^6$ join together to form a ring selected from the group consisting of $C_3$-$C_7$ cycloalkyl, $C_3$-$C_7$ heterocycloalkyl, and substituted $C_3$-$C_7$ heterocycloalkyl;

$R^7$ are independently hydrogen or $C_1$ to $C_6$ alkyl;

or a tautomer and/or a pharmaceutically acceptable salt thereof.

2. The compound of claim 1 selected from the group consisting of:

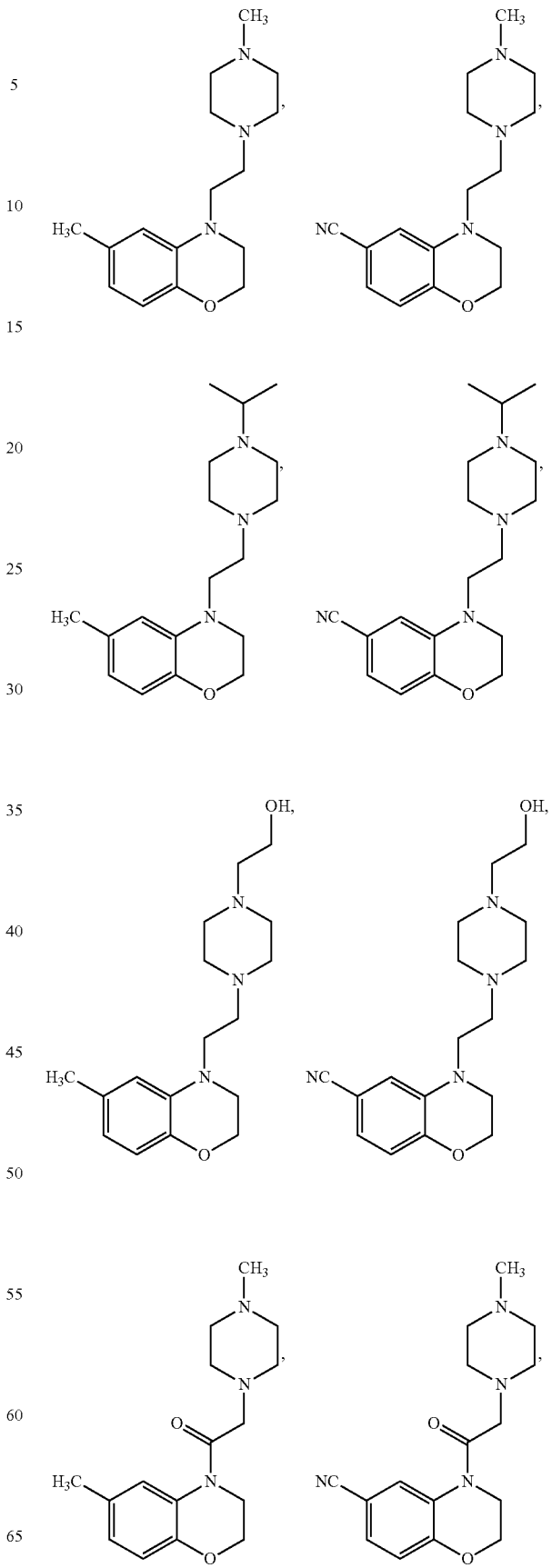

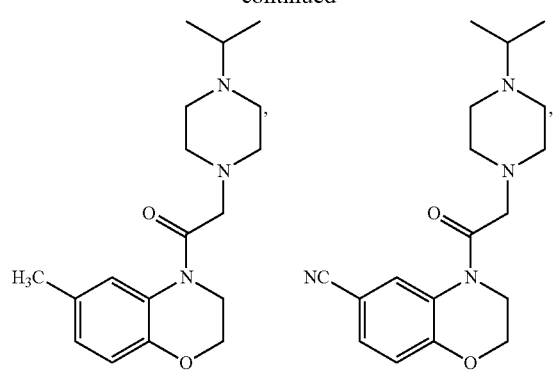
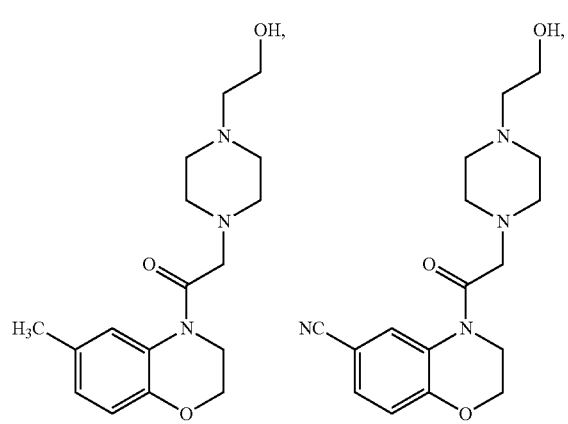
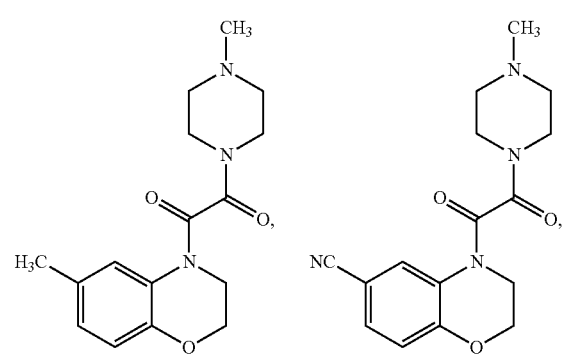
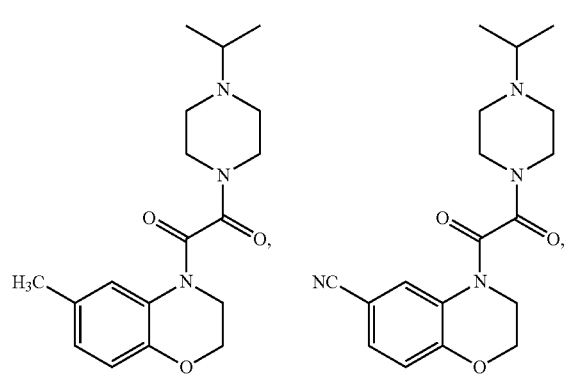
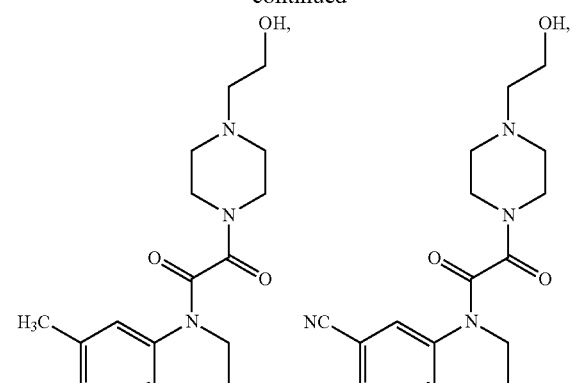
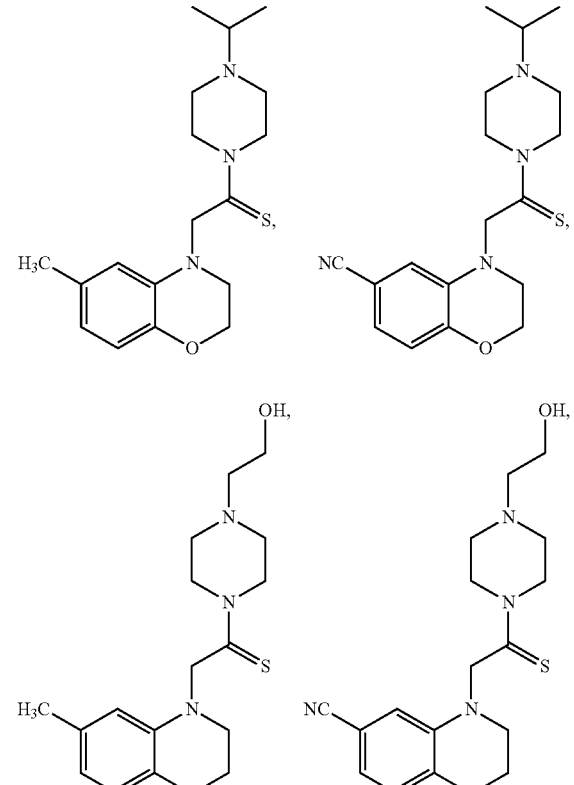

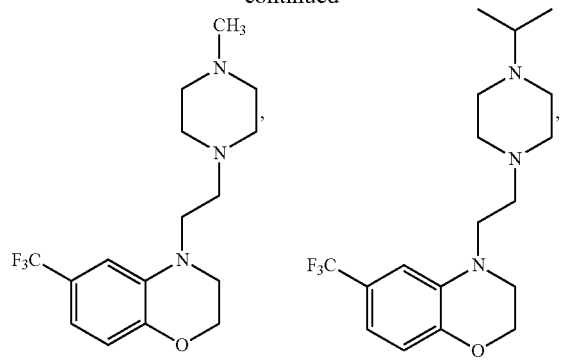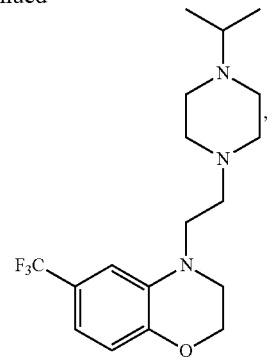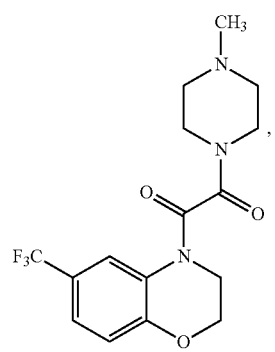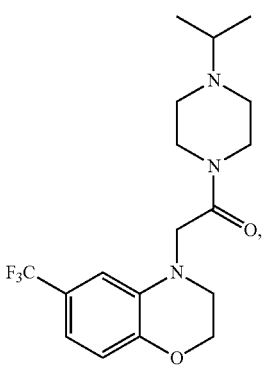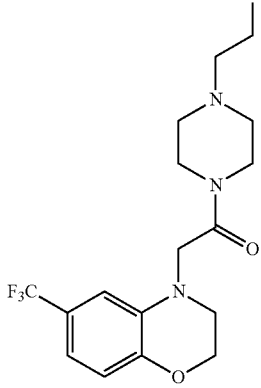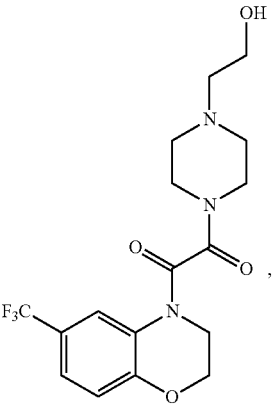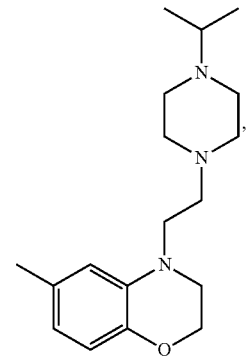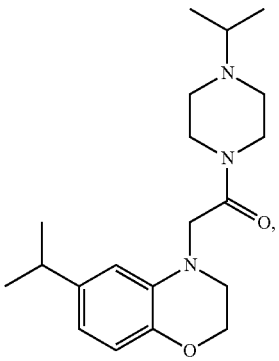

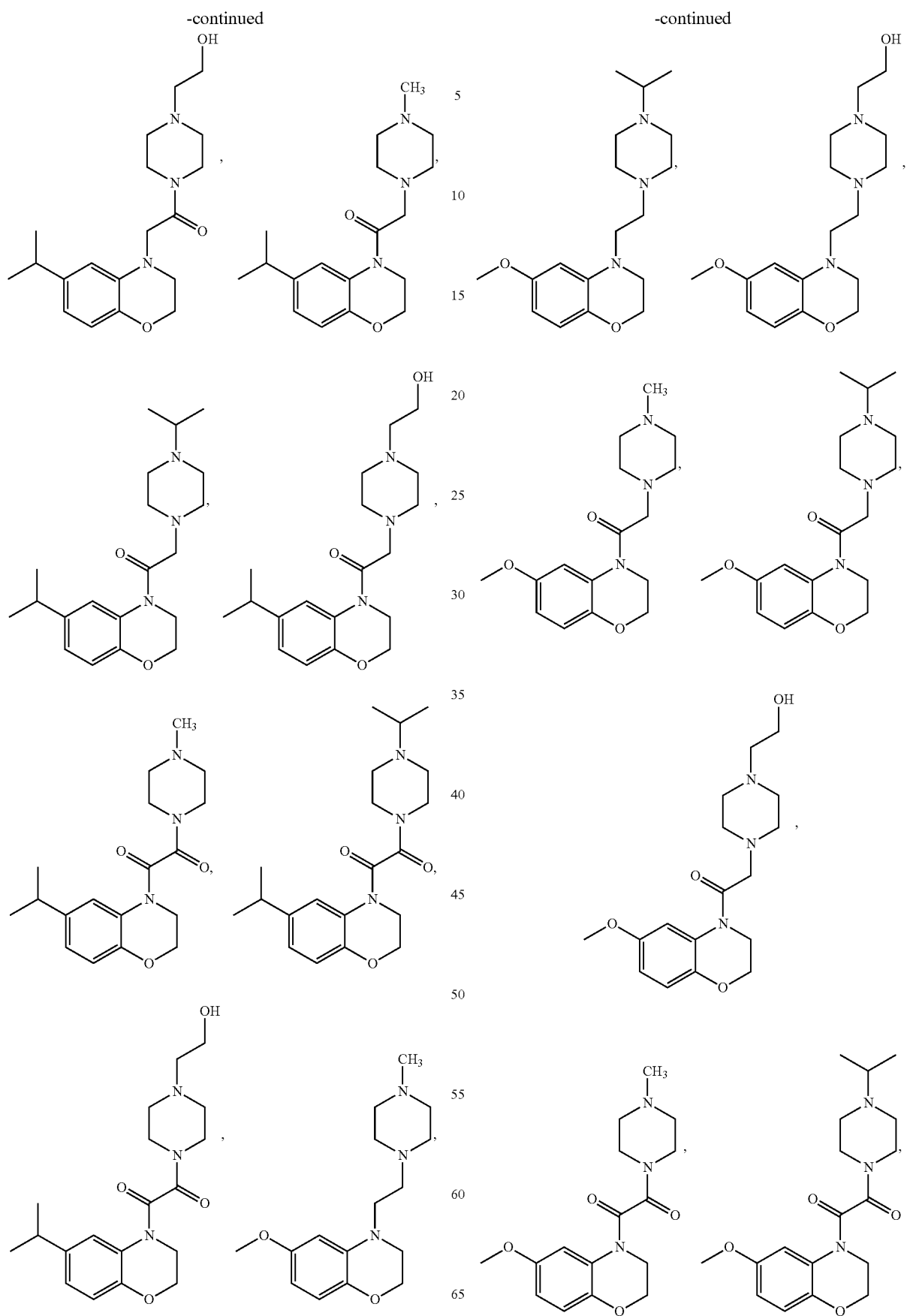

-continued

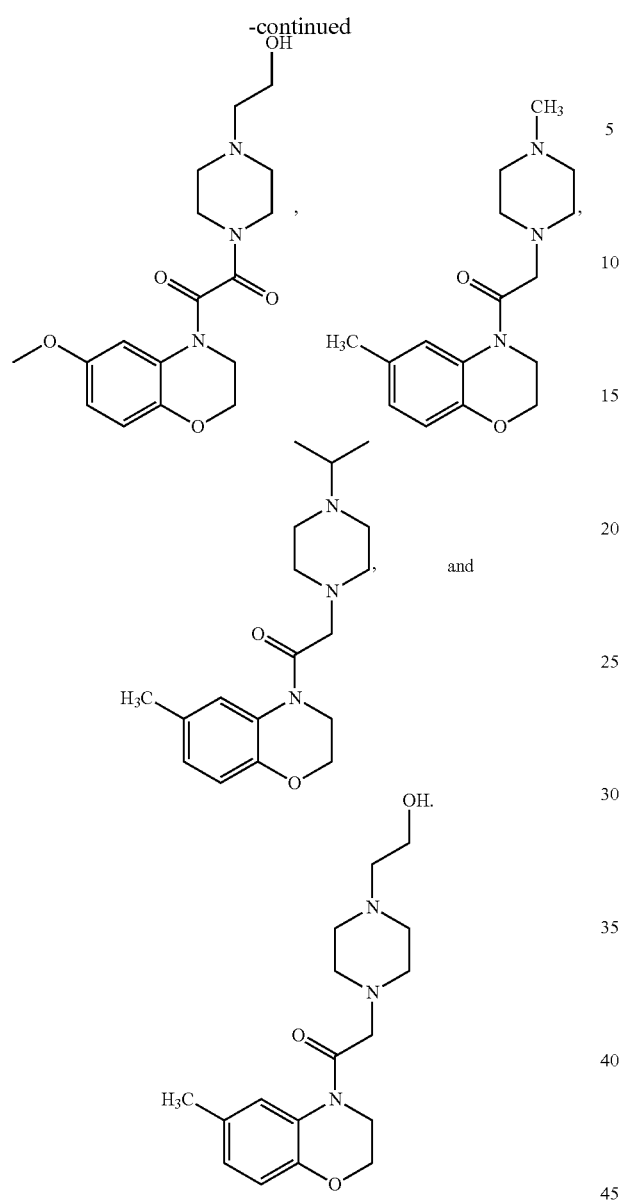

3. The compound according to claim 1 and selected from the group consisting of
- 1-(6-methyl-2,3-dihydro-4H-benzo[b][1,4]oxazin-4-yl)-2-(4-methylpiperazin-1-yl)ethan-1-one,
- 1-(6-methyl-2,3-dihydro-4H-benzo[b][1,4]oxazin-4-yl)-2-(4-phenylpiperazin-1-yl)ethan-1-one,
- 1-(6-methyl-2,3-dihydro-4H-benzo[b][1,4]oxazin-4-yl)-2-(piperazin-1-yl)ethan-1-one,
- 2-(4-acetylpiperazin-1-yl)-1-(6-methyl-2,3-dihydro-4H-benzo[b][1,4]oxazin-4-yl)ethan-1-one,
- 2-(6-methyl-2,3-dihydro-4H-benzo[b][1,4]oxazin-4-yl)-1-(4-methylpiperazin-1-yl)ethan-1-one,
- 6-methyl-4-(2-(4-methylpiperazin-1-yl)ethyl)-3,4-dihydro-2H-benzo[b][1,4]oxazine,
- 2-(4-cyclohexylpiperazin-1-yl)-1-(6-methyl-2,3-dihydro-1,4-benzoxazin-4-yl)ethanone,
- 1-(6-methyl-2,3-dihydro-1,4-benzoxazin-4-yl)-2-(4-propan-2-ylpiperazin-1-yl)ethanone,
- 1-[4-(2-hydroxyethyl)piperazin-1-yl]-2-(6-methyl-2,3-dihydro-1,4-benzoxazin-4-yl)ethanone,
- 1-[4-(2-methoxyethyl)piperazin-1-yl]-2-(6-methyl-2,3-dihydro-1,4-benzoxazin-4-yl)ethanone,
- N-[2-[4-[2-(6-methyl-2,3-dihydro-1,4-benzoxazin-4-yl)acetyl]piperazin-1-yl]ethyl]methanesulfonamide, or their tautomers and/or a pharmaceutically acceptable salt thereof.

4. A compound selected from the group consisting of

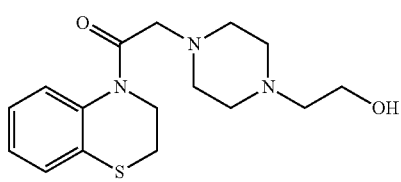

6d

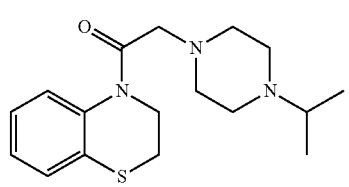

6e

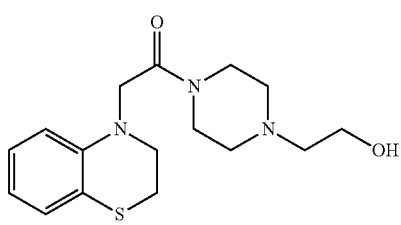

8h

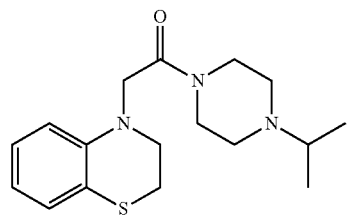

8i

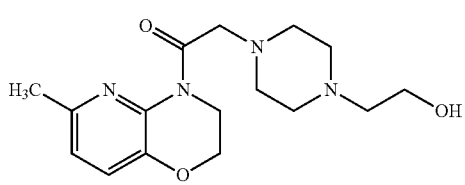

6c

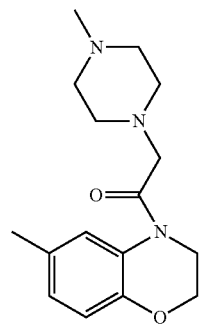

B

105
-continued

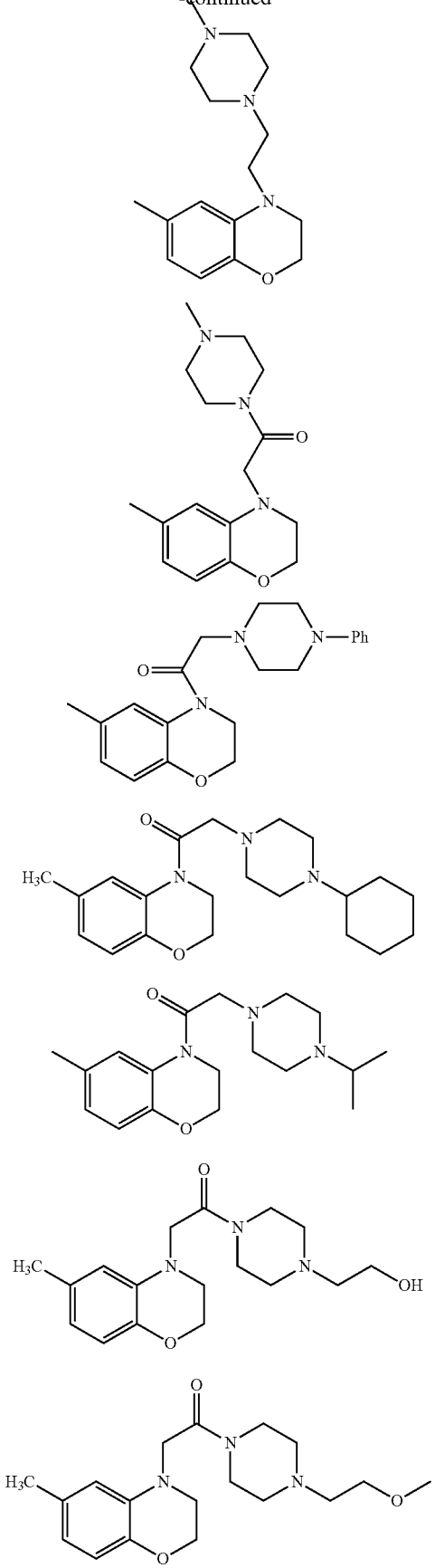

106
-continued

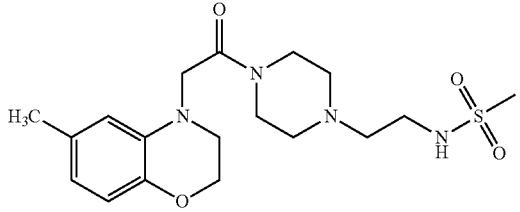

or their tautomers and/or a pharmaceutically acceptable salt thereof.

5. A pharmaceutical composition comprising a compound of claim 1 and a pharmaceutically acceptable excipient.

6. A method for inducing neuronal autophagy which method comprises contacting a cell with an effective amount of a compound of claim 1, wherein the cell is selected from the group consisting of a neuron, microglia, macrophages, and astrocytes.

7. A method for treating a disease which method comprises administering to a patient an effective amount of a compound of claim 1, wherein the disease is selected from the group consisting of Huntington's disease, spinocerebellar ataxias, Alzheimer's disease, Parkinson's disease, frontotemporal dementia, high-pressure neurological syndrome, dystonia, olivopontocerebellar atrophy, amyotrophic lateral sclerosis, multiple sclerosis, epilepsy, stroke, cerebral ischemia, hypoxia, multi-infarct dementia, cerebral trauma or damage, damage to the spinal cord, AIDS-dementia complex, viral or bacterial meningitis, poliomyelitis, Lyme disease, malaria, cancers with cerebral localization, Tourette's syndrome, hepatic encephalopathy, systemic lupus, analgesia, opiate-withdrawal symptoms, feeding behavior, schizophrenia, chronic anxiety, depressive disorders, disorders of the developing or aged brain alcoholism, nicotine addiction, illicit drug addiction, and type 2 diabetes.

8. A method for treating Huntington's disease, wherein the method comprises administering to a patient an effective amount of a compound of claim 1.

9. The compound of claim 1 of formula V:

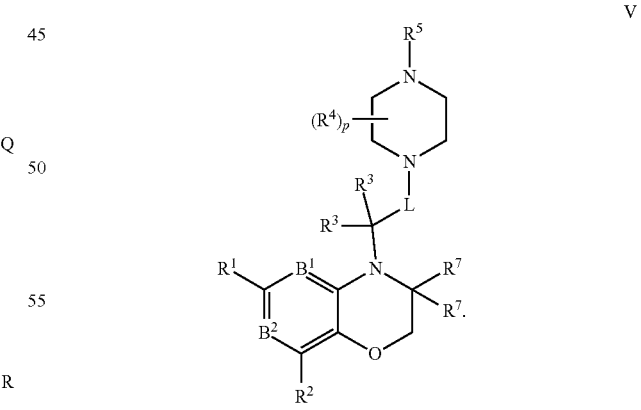

10. The compound of claim 9 wherein $R^7$ is hydrogen.
11. The compound of claim 9 wherein L is $CR^6{}_2$ or $C(O)-(CR^6{}_2)_m$.
12. The compound of claim 9 wherein L is $CR^6{}_2$ or $C(O)$.
13. A pharmaceutical composition comprising a compound of claim 9 and a pharmaceutically acceptable excipient.

14. A method for inducing neuronal autophagy which method comprises contacting a cell with an effective amount of a compound of claim 9, wherein the cell is selected from the group consisting of a neuron, microglia, macrophages, and astrocytes.

15. A method for treating a disease which method comprises administering to a patient an effective amount of a compound of claim 9, wherein the disease is selected from the group consisting of Huntington's disease, spinocerebellar ataxias, Alzheimer's disease, Parkinson's disease, frontotemporal dementia, high-pressure neurological syndrome, dystonia, olivopontocerebellar atrophy, amyotrophic lateral sclerosis, multiple sclerosis, epilepsy, stroke, cerebral ischemia, hypoxia, multi-infarct dementia, cerebral trauma or damage, damage to the spinal cord, AIDS-dementia complex, viral or bacterial meningitis, poliomyelitis, Lyme disease, malaria, cancers with cerebral localization, Tourette's syndrome, hepatic encephalopathy, systemic lupus, analgesia, opiate-withdrawal symptoms, feeding behavior, schizophrenia, chronic anxiety, depressive disorders, disorders of the developing or aged brain alcoholism, nicotine addiction, illicit drug addiction, and type 2 diabetes.

16. A method for treating Huntington's disease, wherein the method comprises administering to a patient an effective amount of a compound of claim 9.

\* \* \* \* \*

UNITED STATES PATENT AND TRADEMARK OFFICE
CERTIFICATE OF CORRECTION

PATENT NO. : 10,087,151 B2
APPLICATION NO. : 15/110082
DATED : October 2, 2018
INVENTOR(S) : Andrey S. Tsvetkov et al.

Page 1 of 1

It is certified that error appears in the above-identified patent and that said Letters Patent is hereby corrected as shown below:

In the Claims

In Claim 4, please replace the following structure at Column 104, Line 50:

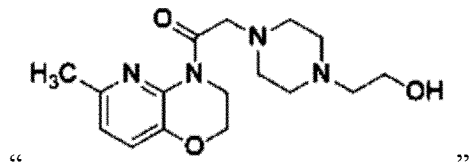

"                                    "

With:

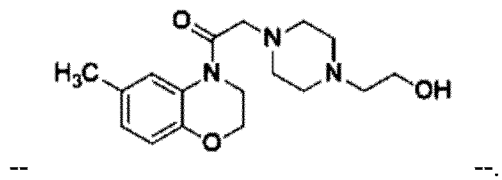

--                                   --.

Signed and Sealed this
Twelfth Day of March, 2019

Andrei Iancu
*Director of the United States Patent and Trademark Office*